(12) United States Patent
Mallery et al.

(10) Patent No.: US 10,758,619 B2
(45) Date of Patent: Sep. 1, 2020

(54) CONTROLLED RELEASE MUCOADHESIVE SYSTEMS

(75) Inventors: Susan R. Mallery, Columbus, OH (US); Peter E. Larsen, Powell, OH (US); Gary D. Stoner, Worthington, OH (US); Steven P. Schwendeman, Superior Township, MI (US); Kashappa-Goud Desai, Ann Arbor, MI (US)

(73) Assignees: THE OHIO STATE UNIVERSITY, Columbus, OH (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 754 days.

(21) Appl. No.: 13/885,436

(22) PCT Filed: Nov. 15, 2011

(86) PCT No.: PCT/US2011/060838
§ 371 (c)(1),
(2), (4) Date: Nov. 8, 2013

(87) PCT Pub. No.: WO2012/068147
PCT Pub. Date: May 24, 2012

(65) Prior Publication Data
US 2014/0056949 A1 Feb. 27, 2014

Related U.S. Application Data

(60) Provisional application No. 61/413,982, filed on Nov. 15, 2010.

(51) Int. Cl.
| | | |
|---|---|---|
| *A61K 47/10* | (2017.01) | |
| *A61K 9/00* | (2006.01) | |
| *A61K 31/07* | (2006.01) | |
| *A61K 9/70* | (2006.01) | |
| *A61K 47/32* | (2006.01) | |
| *A61K 47/24* | (2006.01) | |
| *A61K 47/28* | (2006.01) | |

(52) U.S. Cl.
CPC .............. *A61K 47/10* (2013.01); *A61K 9/006* (2013.01); *A61K 9/0056* (2013.01); *A61K 9/7007* (2013.01); *A61K 31/07* (2013.01); *A61K 47/24* (2013.01); *A61K 47/28* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 4,172,124 A | 10/1979 | Koprowski et al. | |
| 4,196,265 A | 4/1980 | Koprowski et al. | |
| 4,608,337 A | 8/1986 | Croce | |
| 4,665,098 A | 5/1987 | Gibbs et al. | |
| 4,693,975 A | 9/1987 | Kozbor et al. | |
| 4,701,409 A | 10/1987 | Croce | |
| 4,876,092 A | 10/1989 | Mizobuchi et al. | |
| 5,015,568 A | 5/1991 | Tsujimoto et al. | |
| 5,149,628 A | 9/1992 | Croce | |
| 5,198,338 A | 3/1993 | Croce | |
| 5,202,429 A | 4/1993 | Tsujimoto et al. | |
| 5,459,251 A | 10/1995 | Tsujimoto et al. | |
| 5,464,870 A | 11/1995 | Veronesi et al. | |
| 5,506,106 A | 4/1996 | Croce et al. | |
| 5,506,344 A | 4/1996 | Tsujimoto et al. | |
| 5,523,393 A | 6/1996 | Tsujimoto et al. | |
| 5,567,586 A | 10/1996 | Croce | |
| 5,595,869 A | 1/1997 | Tsujimoto et al. | |
| 5,629,019 A * | 5/1997 | Lee ...................... | A61K 9/0014 424/449 |
| 5,633,135 A | 5/1997 | Croce et al. | |
| 5,633,136 A | 5/1997 | Croce et al. | |
| 5,674,682 A | 10/1997 | Croce et al. | |
| 5,688,649 A | 11/1997 | Croce et al. | |
| 5,695,944 A | 12/1997 | Croce et al. | |
| 5,928,884 A | 7/1999 | Croce et al. | |
| 5,939,258 A | 8/1999 | Croce et al. | |
| 5,985,598 A | 11/1999 | Russo et al. | |
| 6,040,140 A | 3/2000 | Croce et al. | |
| 6,130,201 A | 10/2000 | Croce et al. | |
| 6,187,536 B1 | 2/2001 | Weinberg et al. | |
| 6,242,212 B1 | 6/2001 | Croce et al. | |
| 6,255,293 B1 | 7/2001 | Kimchi | |
| 6,258,541 B1 | 7/2001 | Chapkin et al. | |
| 6,368,831 B1 | 4/2002 | Maurer et al. | |
| 6,562,363 B1 * | 5/2003 | Mantelle .............. | A61K 9/0014 424/434 |
| 6,774,217 B1 | 8/2004 | Croce et al. | |

(Continued)

FOREIGN PATENT DOCUMENTS

| | | |
|---|---|---|
| AU | 2007-243475 B2 | 5/2013 |
| CA | 2533701 A1 | 2/2005 |

(Continued)

OTHER PUBLICATIONS

Australian Exam Rpt. No. 3, 2007205257, dated Jan. 9, 2013.
Australian Examination Report No. 2, 2007227423, dated Mar. 1, 2013.
Australian Office Action, Application No. 2007227423 dated Apr. 13, 2012.
Australian Office Action, Application No. 2006291165 dated Feb. 13, 2012.

(Continued)

*Primary Examiner* — Monica A Shin
(74) *Attorney, Agent, or Firm* — Marshall, Gerstein & Borun LLP

(57) ABSTRACT

Formulations for chemoprevention of oral cancer and precancerous lesions, and for methods for preparing the formulations are described.

30 Claims, 10 Drawing Sheets

(56) References Cited

U.S. PATENT DOCUMENTS

| | | |
|---|---|---|
| 6,924,414 B2 | 8/2005 | Croce et al. |
| 7,060,811 B2 | 6/2006 | Aldaz et al. |
| 7,141,417 B1 | 11/2006 | Croce et al. |
| 7,169,813 B2 | 1/2007 | Formelli |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,455,995 B2 | 11/2008 | Tanner et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,785,621 B2 | 8/2010 | Maurer et al. |
| 7,790,905 B2 | 9/2010 | Tawa et al. |
| 7,811,759 B2 | 10/2010 | Han |
| 7,888,010 B2 | 2/2011 | Brown et al. |
| 7,919,245 B2 | 4/2011 | Brown et al. |
| 8,084,199 B2 | 12/2011 | Croce et al. |
| 8,088,822 B2 | 1/2012 | Zhang et al. |
| 8,361,710 B2 | 1/2013 | Croce et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2003/0143646 A1 | 7/2003 | Laskey et al. |
| 2003/0206958 A1 | 11/2003 | Cattaneo et al. |
| 2004/0028721 A1* | 2/2004 | Colombo ............ A61K 9/0009 424/443 |
| 2004/0033254 A1* | 2/2004 | Song ................ A61K 9/7053 424/449 |
| 2004/0033502 A1 | 2/2004 | Williams et al. |
| 2004/0078834 A1 | 4/2004 | Croce |
| 2004/0151774 A1* | 8/2004 | Pauletti ............ A61K 9/0034 424/486 |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0013247 A1 | 1/2005 | Sipola et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0106216 A1 | 5/2005 | Maurer et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0116321 A1 | 6/2006 | Robbins et al. |
| 2006/0121085 A1 | 6/2006 | Warren et al. |
| 2006/0127895 A1 | 6/2006 | Sabapathy |
| 2006/0134639 A1 | 6/2006 | Huffel et al. |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0199233 A1 | 9/2006 | Dahlberg et al. |
| 2006/0247448 A1 | 11/2006 | Boivin et al. |
| 2006/0292616 A1 | 12/2006 | Neely et al. |
| 2007/0015841 A1 | 1/2007 | Tawa et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0092882 A1 | 4/2007 | Wang et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212410 A1* | 9/2007 | Kanios ............... A61K 9/7061 424/457 |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2007/0299043 A1 | 12/2007 | Hunter et al. |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023149 A1 | 1/2009 | Knudsen et al. |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0220589 A1 | 9/2009 | Trieu et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0239818 A1 | 9/2009 | Cheng |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004320 A1 | 1/2010 | Elmen et al. |
| 2010/0004322 A1 | 1/2010 | Croce |
| 2010/0021734 A1 | 1/2010 | Uemoto et al. |
| 2010/0048681 A1 | 2/2010 | Croce |
| 2010/0099200 A1 | 4/2010 | Nazabal et al. |

(56) References Cited

U.S. PATENT DOCUMENTS

| | | |
|---|---|---|
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0151480 A1 | 6/2010 | Taylor et al. |
| 2010/0173319 A1 | 7/2010 | Croce et al. |
| 2010/0179213 A1 | 7/2010 | Patrawala et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0285471 A1 | 11/2010 | Croce et al. |
| 2010/0298410 A1 | 11/2010 | Obad et al. |
| 2010/0305188 A1 | 12/2010 | Nakano et al. |
| 2010/0317610 A1 | 12/2010 | Croce |
| 2011/0003704 A1 | 1/2011 | Skog et al. |
| 2011/0021601 A1 | 1/2011 | Park et al. |
| 2011/0054006 A1 | 3/2011 | Slack et al. |
| 2011/0054009 A1 | 3/2011 | Croce et al. |
| 2011/0107440 A1 | 5/2011 | Pivarcsi et al. |
| 2011/0136124 A1 | 6/2011 | Roa et al. |
| 2011/0152267 A1 | 6/2011 | Maurer et al. |
| 2011/0166200 A1 | 7/2011 | Zhang |
| 2011/0251150 A2 | 10/2011 | Bennett et al. |
| 2011/0275534 A1 | 11/2011 | Cohn et al. |

FOREIGN PATENT DOCUMENTS

| | | | |
|---|---|---|---|
| CA | 2587189 A1 | 12/2006 | |
| CN | 101623277 A | 1/2010 | |
| CN | 101215560 B | 9/2010 | |
| CN | 1282422 A | 1/2011 | |
| EP | 1296650 B1 | 3/2005 | |
| EP | 1662259 A1 | 5/2006 | |
| EP | 1676914 A1 | 7/2006 | |
| EP | 2170304 B1 | 12/2010 | |
| EP | 2354246 A1 | 8/2011 | |
| EP | 2487240 A1 | 8/2012 | |
| FR | 2877350 A1 | 5/2006 | |
| JP | 62-178513 | 8/1987 | |
| JP | 2003-55201 | 2/2003 | |
| JP | 2005-503827 A | 2/2005 | |
| JP | 2005-517452 A | 6/2005 | |
| JP | 2008-086201 A | 4/2008 | |
| JP | 5395439 B2 | 1/2014 | |
| WO | 1990/15156 A1 | 12/1990 | |
| WO | 1991/00364 A1 | 1/1991 | |
| WO | 1991/07424 A1 | 5/1991 | |
| WO | 1993/12136 A1 | 6/1993 | |
| WO | 1994/10343 A1 | 5/1994 | |
| WO | 1994/24308 A1 | 10/1994 | |
| WO | 1994/26930 A1 | 11/1994 | |
| WO | 1996/13514 A1 | 5/1996 | |
| WO | 1996/35124 A1 | 11/1996 | |
| WO | 1997/29119 A1 | 8/1997 | |
| WO | 1998/09510 A1 | 3/1998 | |
| WO | 2000/03685 A2 | 1/2000 | |
| WO | 2000/50565 A2 | 8/2000 | |
| WO | 2000/55169 A1 | 9/2000 | |
| WO | 2000/076524 A1 | 12/2000 | |
| WO | 2001/07914 A1 | 2/2001 | |
| WO | 2001007914 A1 | 2/2001 | |
| WO | 2001/44466 A1 | 6/2001 | |
| WO | 2001/68666 A1 | 9/2001 | |
| WO | 2001/77343 A1 | 10/2001 | |
| WO | 2001/87958 A2 | 11/2001 | |
| WO | 02/058689 | 8/2002 | |
| WO | 2002/064171 A1 | 8/2002 | |
| WO | 2002/064172 A2 | 8/2002 | |
| WO | 2003/029459 A2 | 4/2003 | |
| WO | 2003/078662 A1 | 9/2003 | |
| WO | 2003/092370 A1 | 11/2003 | |
| WO | 2004/033659 A2 | 4/2004 | |
| WO | 2004/043387 A2 | 5/2004 | |
| WO | WO-2004052347 | * 6/2004 | ............... A61K 9/00 |
| WO | 2004/079013 A1 | 9/2004 | |
| WO | 2004/098377 A2 | 11/2004 | |
| WO | 2005/009342 | 2/2005 | |
| WO | 2005/013901 A3 | 2/2005 | |
| WO | 2005/017711 A2 | 2/2005 | |
| WO | 2005/020795 A2 | 3/2005 | |
| WO | 2005/053698 | 6/2005 | |
| WO | 2005/060661 A2 | 7/2005 | |
| WO | 2005-192484 A | 7/2005 | |
| WO | 2005/078139 A2 | 8/2005 | |
| WO | 2005/079397 A2 | 9/2005 | |
| WO | 2005/080601 A2 | 9/2005 | |
| WO | 2005/094263 A2 | 10/2005 | |
| WO | 2005-296014 A | 10/2005 | |
| WO | 2005/103298 A2 | 11/2005 | |
| WO | 2005/111211 A2 | 11/2005 | |
| WO | 2005/118806 A2 | 12/2005 | |
| WO | 2006/133022 A2 | 12/2005 | |
| WO | 2006/105486 A2 | 10/2006 | |
| WO | 2006/108718 A1 | 10/2006 | |
| WO | 2006/19266 A2 | 11/2006 | |
| WO | 2006/119365 A3 | 11/2006 | |
| WO | 2006/137941 A2 | 12/2006 | |
| WO | 2007/016548 A2 | 2/2007 | |
| WO | 2007/033023 A2 | 3/2007 | |
| WO | 2007/044413 A2 | 4/2007 | |
| WO | 2007/081680 A2 | 7/2007 | |
| WO | 2007/081720 A2 | 7/2007 | |
| WO | 2007/081740 A2 | 7/2007 | |
| WO | 2007/084486 A2 | 7/2007 | |
| WO | 2007/109236 A2 | 9/2007 | |
| WO | 2007/112097 A2 | 10/2007 | |
| WO | 2007/112754 A2 | 10/2007 | |
| WO | 2007/115134 A2 | 10/2007 | |
| WO | 2007115134 A1 | 10/2007 | |
| WO | 2007/127190 A2 | 11/2007 | |
| WO | WO-2007136636 | * 11/2007 | ............. A61K 31/44 |
| WO | 2008/008430 A2 | 1/2008 | |
| WO | 2008/029295 A2 | 3/2008 | |
| WO | 2008/036168 A2 | 3/2008 | |
| WO | 2008/036776 A2 | 3/2008 | |
| WO | 2008/054828 A2 | 5/2008 | |
| WO | 2008/064519 A1 | 6/2008 | |
| WO | 2008/070082 A2 | 6/2008 | |
| WO | 2008/073915 A2 | 6/2008 | |
| WO | 2008/073920 A2 | 6/2008 | |
| WO | 2008/094545 A2 | 8/2008 | |
| WO | 2008/097277 A2 | 8/2008 | |
| WO | 2008/120815 | 10/2008 | |
| WO | 2008/136971 A1 | 11/2008 | |
| WO | 2008/153987 A2 | 12/2008 | |
| WO | 2008/157319 A1 | 12/2008 | |
| WO | 2009/018303 A2 | 2/2009 | |
| WO | 2009/020905 A2 | 2/2009 | |
| WO | 2009/026487 A1 | 2/2009 | |
| WO | 2009/033140 A1 | 3/2009 | |
| WO | 2009/036236 A1 | 3/2009 | |
| WO | 2009/049129 A1 | 4/2009 | |
| WO | 2009/055773 A2 | 4/2009 | |
| WO | 2009/064590 A2 | 5/2009 | |
| WO | 2009/070653 A1 | 6/2009 | |
| WO | 2009/100029 A1 | 8/2009 | |
| WO | 2009/103353 A1 | 9/2009 | |
| WO | 2009/108856 A2 | 9/2009 | |
| WO | 2009/108860 A2 | 9/2009 | |
| WO | 2009/108866 A2 | 9/2009 | |
| WO | 2009/152300 A1 | 12/2009 | |
| WO | 2010/019694 A1 | 2/2010 | |
| WO | 2010/059779 A1 | 5/2010 | |
| WO | 2010/065156 A1 | 6/2010 | |
| WO | 2010/099161 A1 | 9/2010 | |
| WO | 2011/057304 A2 | 5/2011 | |

(56) References Cited

FOREIGN PATENT DOCUMENTS

| WO | 2011/059776 A2 | 5/2011 |
|---|---|---|
| WO | 2011/063382 A1 | 5/2011 |
| WO | 2011059776 A1 | 5/2011 |
| WO | 2011/119553 A2 | 9/2011 |
| WO | 2011/163116 A3 | 12/2011 |
| WO | 2012/019053 A2 | 2/2012 |
| WO | 2012/065049 A2 | 5/2012 |
| WO | 2012/068147 A1 | 5/2012 |
| WO | 2012068147 A1 | 5/2012 |
| WO | 2012/097047 A1 | 7/2012 |
| WO | 2012/122239 A1 | 9/2012 |

OTHER PUBLICATIONS

Australian Office Action, Application No. 2007205234 dated Jun. 17, 2011.
Australian Office Action, Application No. 2007205257 dated Oct. 24, 2011.
Australian Office Action, Application No. 2007272947 dated May 21, 2012.
Australian Office Action Application No. 2008282318 dated Feb. 7, 2013.
Australian Office Action, Application No. 2007205163 dated Mar. 28, 2013.
Australian Office Action Application No. 2007205257 dated Feb. 26, 2013.
Australian Office Action, Application No. 2007314212 dated Apr. 29, 2013.
Australian Office Action, Application No. 2008262252 dated Feb. 15, 2013.
Australian Office Action, Report No. 2, Application No. 2008248319 dated Apr. 9, 2013.
Australian Office Action, Application No. 2007205163 dated Nov. 15, 2012.
Australian Office Action, Application No. 2006291165 dated Sep. 12, 2012.
Australian Office Action, Application No. 2007205257 dated Jul. 16, 2012.
Australian Office Action, Application No. 2008266014 dated Jul. 6, 2012.
Australian Office Action, Application No. 2007314212 dated Aug. 28, 2012.
Australian Office Action, Application No. 2006291165 dated Jan. 7, 2013.
Australian Office Action, Application No. 2007346101 dated Jun. 21, 2012.
Australian Office Action, Application No. 2008248319 dated Jul. 12, 2012.
Australian Patent Examination Report No. 2, Application No. 2008288806, dated Mar. 25, 2014.
Australian Patent Examination Report No. 1, Appln. No. 2009219197, dated Sep. 19, 2013.
Australian Patent Examination Rpt., No. 1., 2008316577 dated Feb. 11, 2013.
Australian Patent Examination Report No. 2, Appln. No. 2007346101, dated May 24, 2013.
Australian Patent Examination Report No. 1, Appln. No. 2008283997 dated Aug. 20, 2007.
Australian Patent Examination Report No. 1, Appln. No. 2008310704, dated Jun. 24, 2013.
Australian Patent Examination Report No. 2, Application No. 2008282318 , dated Nov. 19, 2013.
Australian Patent Examination Report No. 1, Application No. 2009281969, dated Jan. 16, 2014.
Canadian Intellectual Property Office, Requisition by the Examiner, Application No. 2,657,030, dated Jan. 13, 2014.
Canadian Intellectual Property Office, Requisition by the Examiner, Application No. 2,667,617, dated Jan. 2, 2014.
Canadian Intellectual Property Office, Requisition by the Examiner, Application 2,621,441 dated Apr. 8, 2013.
Canadian Intellectual Property Office, Requisition by the Examiner, Application No. 2,635,616, dated Feb. 21, 2011.
Canadian Intellectual Property Office, Requisition by the Examiner, Application No. 2,646,051, dated Feb. 25, 2011.
Canadian Office Action, Application No. 2,617,581, dated Feb. 1, 2011.
Canadian Office Action, Application No. 2,617,581, dated Apr. 2, 2012.
Canadian Office Action, Application No. 2,621,441, dated Feb. 1, 2011.
Canadian Office Action, Application No. 2,635,616, dated Feb. 27, 2012.
Chinese 1st Office Action, Appln. No. 201110319534.7, dated Jun. 8, 2013.
Chinese 1st Office Action, Appln. No. 200880025276.8, dated Nov. 23, 2011.
Chinese 1st Office Action, Appln. No. 201210312507.1, dated Jul. 29, 2013.
Chinese 1st Office Action, Appln. No. 200980112966.1, dated Sep. 20, 2012.
Chinese 1st Office Action Appln. No. 201080059339.9 dated Aug. 26, 2013.
Chinese 1st Office Action, Appln. No. 200880108689.2, dated Feb. 13, 2012.
Chinese 1st Office Action, Application No. 200780018496.3 dated Mar. 22, 2011.
Chinese 1st Office Action, Appln. No. 200780005791.5, dated Mar. 24, 2011.
Chinese 1st Office Action, Appln. No. 200880112581.0, dated Aug. 13, 2012.
Chinese 1st Office Action, Application No. 200780023093.8 dated Dec. 27, 2010.
Chinese 1st Office Action, Appln. No. 200980135456.6, dated Nov. 13, 2012.
Chinese 1st Office Action, Appln. No. 200980114564.5, dated Dec. 19, 2013.
Chinese 1st Office Action, Appln. No. 200980155340.9 dated Jan. 21, 2013.
Chinese 1st Office Action, Appln. No. 200980126520.4, dated Dec. 4, 2012.
Chinese 1st Office Action, Appln. No. 200980113258, dated Mar. 13, 2013.
Chinese 2nd OA—EnglishTrans, Appln. No. 200880112581.0, dated May 10, 2013.
Chinese 2nd Office Action Appln. No. 200980126520.4 dated Aug. 14, 2013.
Chinese 2nd Office Action, Application No. 200780018496.3 dated Mar. 1, 2012.
Chinese 2nd Office Action, Appln. No. 200980135456.6 dated Aug. 1, 2013.
Chinese 2nd Office Action, Appln. No. 200880103023.8 dated Jun. 20, 2013.
Chinese 2nd Office Action, Appln. No. 200980155340.9, dated Aug. 26, 2013.
Chinese 2nd Office Action Application No. 200980111708.1 dated May 20, 2013.
Chinese 2nd Office Action, Appln. No. 200880003736.7 dated Nov. 5, 2012.
Chinese 2nd Office Action, Appln. No. 200780005791.5, dated May 3, 2012.
Chinese 2nd Office Action, Application No. 200780023093.8 dated Dec. 9, 2011.
Chinese 2nd Office Action, Appln. No. 200880119206.9, dated Feb. 1, 2013.
Chinese 2nd Office Action, Application No. 200780005821.2 dated Apr. 1, 2012.
Chinese 2nd Office Action, Appln. No. 200980112966.1, dated May 9, 2013.
Chinese 2nd Office Action Appln. No. 200880025276.8 dated Aug. 1, 2012.
Chinese 2nd Office Action, Application No. 200780040146.7 dated Dec. 31, 2011.

(56) References Cited

OTHER PUBLICATIONS

Chinese 3rd Office Action, Application No. 200880116343.7 dated Apr. 8, 2013.
Chinese 3rd Office Action, Application No. 200780040146.7 dated Apr. 25, 2012.
Chinese 3rd Office Action, Appln. No. 200880116343.7, dated Apr. 8, 2013.
Chinese 3rd Office Action, Application No. 200780023093.8 dated Jul. 2, 2012.
Chinese 3rd Office Action, Application No. 200880003736.7 dated Apr. 12, 2013.
Chinese 3rd Office Action, Appln. No. 200880108689.2, dated Apr. 1, 2013.
Chinese 3rd Office Action, Application No. 200780005821.2 dated Nov. 5, 2012.
Chinese 3rd Office Action, Appln. No. 200880119206.9 dated Aug. 12, 2013.
Chinese 3rd Office Action, Application No. 200980111708.1, dated Nov. 4, 2013.
Chinese 3rd OfficeAction, Appln. No. 200780005791.5, dated Dec. 5, 2012.
Chinese 4th Office Action, Application No. 200780023093.8 dated Jan. 14, 2013.
Chinese 4th Office Action Appln. No. 200880116343.7 dated Jul. 10, 2013.
Chinese 4th Office Action Application No. 200780005821.2 dated May 13, 2013.
Chinese 4th Office Action, Application No. 200780040146.7 dated Nov. 23, 2012.
Chinese 5th Office Action, Application No. 200780040146.7 dated Apr. 16, 2013.
Chinese Fourth Office Action, dated Nov. 19, 2013, Appln. No. 200880022612.3
Chinese Notification of the Second Office Action, Application No. 201080059339.9, dated Apr. 9, 2014.
Chinese Notification of the First Office Action, Appln. No. 201210380806.9, dated Nov. 5, 2013.
Chinese Notification of Third Office Action, Application No. 200980112966.1, dated Dec. 4, 2013.
Chinese Office Action, Application No. 200880108625.2 dated Aug. 21, 2012.
Chinese Office Action, Application No. 200880112585.9 dated May 24, 2012.
Chinese Office Action Application No. 200880108625.2 dated Feb. 13, 2012.
Chinese Office Action, Application No. 200780033066.9 dated Jun. 26, 2012.
Chinese Office Action, Application No. 200780040146.7 dated May 25, 2011.
Chinese Office Action, Application No. 200680036598.3 dated Feb. 24, 2011.
Chinese Office Action, Application No. 200880116343.7 dated Jan. 31, 2012.
Chinese Office Action 1st Application No. 200780033066.9 dated Sep. 18, 2011.
Chinese Office Action 3rd Application No. 200780033066.9 dated Dec. 17, 2012.
Chinese Office Action Application No. 200880022612.3 dated May 17, 2013.
Chinese Office Action, Application No. 200780005821.2 dated Jan. 26, 2011.
Chinese Office Action, 1st Application No. 200880022612.3 dated Apr. 24, 2012.
Chinese Office Action, Application No. 200880108689.2 dated Sep. 12, 2012.
Chinese Office Action, Application No. 200780018496.3 dated Sep. 5, 2012.
Chinese Office Action, Application No. 200880119206 dated May 3, 2012.
Chinese Office Action, Application No. 200980111708.1 dated Aug. 27, 2012.
Chinese Office Action, Application No. 200880108625.2 dated Jan. 5, 2013.
Chinese Office Action, Application No. 200680039776.8 dated Jun. 30, 2011.
Chinese Office Action, Application No. 200980112966.1 dated Sep. 20, 2012.
Chinese Office Action, Application No. 200880112585.9 dated Jan. 27, 2013.
Chinese Office Action, Application No. 200880022612.3 dated Oct. 29, 2012.
Chinese Office Action, Application No. 200880116343.7 dated Oct. 22, 2012.
Chinese Office Action, Application No. 200780018496.3 dated Apr. 8, 2011.
Chinese Office Action, Application No. 200880103023.8 dated Oct. 9, 2012.
Chinese Rejection Decision Appln. No. 200780033066.9 dated Jun. 13, 2013.
Chinese Third Office Action, Application No. 200980135456.6, dated Feb. 8, 2014.
Chinese Third Office Action, Application No. 200980126520.4, dated Feb. 18, 2014.
Communication Concerning Office Action Received from Japanese Patent Office dated Dec. 12, 2012, Japanese Patent Application No. 2008-549555.
Communication Concerning Office Action Received from Japanese Patent Office dated Jan. 31, 2013, Japanese Patent Application No. 2009-535366.
Communication Concerning Office Action Received from Japanese Patent Office dated Dec. 12, 2012, Japanese Patent Application No. 2009-548281.
Communication Concerning Office Action Received from Japanese Patent Office dated Jan. 30, 2012, Japanese Patent Application No. 2008-531200.
Communication Concerning Office Action Received from Japanese Patent Office dated Dec. 11, 2012, Japanese Patent Application No. 2008-549532.
Communication Pursuant to Article 94-3 EPC, Appln. No. 08768266.2 dated Nov. 29, 2012.
EP Communication Appln. No. 11170608.1 dated May 3, 2012.
EP Communication Appln. No. 09715356.3 dated Jul. 10, 2013.
EP Communication Appln. No. 08782609.5 dated Jun. 24, 2011.
EP Communication Appln. No. 12154350.8 dated Jan. 25, 2013.
EP Communication Appn. No. 08782609.5 dated May 24, 2012.
EP Communication Appln, No. 12154343.3 dated Jul. 10, 2012.
EP Communication Appln. No. 08796821.0 dated Jul. 19, 2013.
EP Communication Pursuant to Article 94-3, Appln. No. 12165734.0 dated Aug. 14, 2013.
EP Communication Pursuant to Article 94-3, Appln. No. 11151771.0, dated Jan. 3, 2013.
EP Communication Pursuant to Article 94(3), Application No. 12179592.6, dated May 12, 2014.
EP Communication Pursuant to Article 94-3, Appln. No. 13175161.2, dated Sep. 24, 2013.
EP Communication Pursuant to Article 94-3, Appln. No. 11151769.4, dated Jan. 3, 2013.
EP Communication Pursuant to Article 94-3, Appln. No. 12154350.8 dated Aug. 21, 2013.
EP Communication Pursuant to Article 94-3, Appln. No. 12154307.8 dated Feb. 20, 2013.
EP Communication Pursuant to Article 94-3, Appln. No. 12185438.4 dated Sep. 18, 2013.
EP Communication Pursuant to Article 94(3) EPC, Application No. 12179595.9, dated May 12, 2014.
EP Communication Pursuant to Article 94-3, Appln. No. 12165748.0, dated Sep. 17, 2013.
EP Communication, 09713926.5 dated Jul. 30, 2012.
EP Communication, Application No. 12154347.4 dated Oct. 9, 2013.
EP Communication, Application No. 12154246.8, dated Nov. 22, 2013.

(56) References Cited

OTHER PUBLICATIONS

EP Communication, Application No. 12154298.9, dated Nov. 22, 2013.
EP Communication, Application No. 13159600.9, dated Sep. 19, 2013.
EP Communication, Application No. 12154342.5, dated Mar. 20, 2014.
EP Communication, Application No. 11840508.3, filed Mar. 19, 2014.
EP Communication, Application No. 12154343.3, dated Mar. 21, 2014.
EP Communication, Application No. 12165734.0 dated Apr. 29, 2014.
EP Communication, Application No. 12165740.7, dated Apr. 28, 2014.
EP Communication, Application No. 12165638.3, dated Apr. 2, 2014.
EP Communication, Application No. 10832355.1, dated May 13, 2014.
EP Communication, Appln. No. 12154304.5, dated Feb. 25, 2013.
EP Communication, Appln. No. 08768266.2 dated Jul. 29, 2010.
EP Communication, Appln. No. 07867402.5 dated Dec. 11, 2009.
EP Examination Report 08770974.7 dated Feb. 25, 2013.
EP Examination Report, Application No. 12154346.6 dated Jun. 27, 2013.
EP Examination Report, Application No. 09715064.3 dated Nov. 5, 2012.
EP Extended Srch Rpt., 12185446.7 dated Mar. 28, 2013.
EP Invitation Pursuant to Article 94(3) and Rule 71(1) EPC, Appln. No. 12154354.0, dated Oct. 23, 2013.
EP Sch Rpt., Appln. No. 12154315.1, dated Jul. 20, 2012.
EP Search Report Appln, No. 12154307.8, dated Jun. 26, 2012.
EP Search Report, 12154300.3, dated Jan. 7, 2013.
EP Search Report, Application No. 11196261.9 dated Feb. 28, 2012.
EP Search Report, Application No. 11196264-3 dated Feb. 28, 2012.
EP Search Report, Application No. 12165636.7 dated Sep. 25, 2012.
EP Search Report, Application No. 12165748.0 dated Aug. 23, 2012.
EP Search Report, Application No. 11196250.2 dated Apr. 24, 2012.
EP Search Report, Application No. 11196253.6 dated Apr. 24, 2012.
EP Search Report, Application No. 12154329.2 dated Sep. 19, 2012.
EP Search Report, Application No. 12154322.7 dated Aug. 29, 2012.
EP Search Report, Application No. 12154327.6 dated Sep. 19, 2012.
EP Search Report, Application No. 12154350.8 dated Sep. 27, 2012.
EP Search Report, Application No. 12154347.4 dated Sep. 27, 2012.
EP Search Report, Application No. 12154326.8 dated Sep. 6, 2012.
EP Search Report, Application No. 12154304.5 dated Jun. 26, 2012.
EP Search Report, Application No. 12154332.6 dated Sep. 21, 2012.
EP Search Report, Application No. 12165740.7 dated Aug. 27, 2012.
EP Search Report, Application No. 11196256.9 dated Feb. 28, 2012.
EP Search Report, Application No. 11196254.4 dated Feb. 28, 2012.
EP Search Report, Application No. 12154342.5 dated Jul. 6, 2012.
EP Search Report, Application No. 12154334.2 dated Sep. 21, 2012.
EP Search Report, Application No. 11196190.0 dated Apr. 24, 2012.
EP Search Report, Application No. 12154301.1 dated Aug. 22, 2012.
EP Search Report, Application No. 12154300.3 dated Aug. 20, 2012.
EP Search Report, Application No. 11196265.0 dated Mar. 5, 2012.
EP Search Report, Application No. 12165734.0 dated Aug. 27, 2012.
EP Search Report, Application No. 09830750.7 dated Aug. 27, 2012.
EP Search Report, Application No. 08782609.5 dated Oct. 28, 2010.
EP Search Report, Application No. 12154341.7 dated Aug. 9, 2013.
EP Search Report, Application No. 09807241.6 dated Dec. 6, 2012.
EP Search Report, Application No. 09715356.3 dated Jul. 12, 2012.
EP Search Report, Application No. 12154352.4 dated Oct. 12, 2012.
EP Search Report, Application No. 12154353.2 dated Oct. 15, 2012.
EP Search Report, Application No. 12154351.6 dated Oct. 15, 2012.
EP Search Report, Application No. 12154341.7 dated Oct. 25, 2012.
EP Search Report, Application No. 12154321.9 dated Jul. 20, 2012.
EP Search Report, Application No. 12165638.3 dated Sep. 28, 2012.
EP Search Report, Application No. 12154354.0 dated Oct. 12, 2012.
EP Search Report, Application No. 12154346.6 dated Oct. 23, 2012.
EP Search Report, Application No. 12154298.9 dated Jun. 4, 2012.
EP Search Report, Application No. 12154345.8 dated Sep. 19, 2012.
EP Search Report, Application No. 12154348.2 dated Oct. 9, 2012.
EP Search Report, Application No. 12154344.1 dated Sep. 19, 2012.
EP Search Report, Application No. 12154339.1 dated Oct. 9, 2012.
EP Search Report, Application No. 11196262.7 dated Feb. 28, 2012.
EP Search Report, Application No. 12154337.5 dated Oct. 9, 2012.
EP Search Report, Application No. 12165638.3 dated Jun. 12, 2012.
EP Search Report, Application No. 12154349.0 dated Sep. 27, 2012.
EP Search Report, Application No. 12165636.7 dated Jun. 8, 2012.
European Communication Pursuant to Article 94(3) EPC, Application No. 07717903.4 dated Aug. 16, 2011.
European Communication Pursuant to Article 94(3) EPC, Application No. 08796821.0, dated Jan. 7, 2013.
European Communication Pursuant to Article 94(3)EPC, Application No. 06814375.9 dated Oct. 14, 2011.
European Communication Pursuant to Article 94(3) EPC, Application No. 08799295.4, dated Nov. 18, 2011.
European Communication Pursuant to Article 94(3) EPC, Application No. 07716208.9 dated Sep. 27, 2010.
European Communication, Application No. 07776079.1, dated Sep. 6, 2011.
European Communication Pursuant to Article 94(3) EPC, Application No. 07716208.9 dated Apr. 20, 2010.
European Communication Pursuant to Article 94(3) EPC, Application No. 07717903.4 dated Jan. 29, 2010.
European Communication Pursuant to Article 94(3) EPC, Application No. 08767439.6, dated Feb. 12, 2011.
European Communication Pursuant to Article 94(3) EPC, Application No. 09830750.7, dated Apr. 18, 2013.
European Communication Pursuant to Article 94(3) EPC, Application No. 07716208.9 dated Sep. 13, 2012.
European Communication Pursuant to Article 94(3) EPC, Application No. 06800599.0 dated Nov. 25, 2011.
European Communication Pursuant to Article 94-3 Appln. No. 08799295.4 dated Dec. 10, 2012.
European Communication Pursuant to Article 94(3) EPC, Application No. 07867402.5, dated Jan. 5, 2011.
European Communication Pursuant to Article 94(3) EPC, Application No. 07810382.7, dated Dec. 8, 2010.
European Communication Pursuant to Article 94(3) EPC, Application No. 08768266.2, dated Apr. 18, 2011.
European Communication Pursuant to Article 94(3) EPC, Application No. 07716208.9, dated Sep. 13, 2011.
European Communication Pursuant to Article 94(3) EPC, Application No. 08841700.1, dated Jun. 1, 2012.
European Communication Pursuant to Article 94(3) EPC, Application No. 07867402.5, dated Apr. 10, 2012.
European Communication Pursuant to Article 94(3) EPC, Application No. 07717903.4, dated Apr. 25, 2012.
European Communication, Application No. 09715064.3, dated Feb. 12, 2014.
European Communication Pursuant to Article 94(3) EPC, Application No. 08767439.9, dated Mar. 15, 2011.
European Examination Rpt., 11196265.0, dated Feb. 22, 2013.
European Patent Application, EP 1795203 A2, Croce et al., Application No. 06010581.4, filed Feb. 7, 1997, published Jun. 13, 2007.
European Patent Application, EP 2 481 806 A3, Croce, Filed Apr. 29, 2008, published Oct. 31, 2012.
European Seach Report, Application No. 11151749.6, dated Feb. 8, 2011.
European Seach Report, Application No. 09714868.8 dated Aug. 1, 2011.
European Search Reoprt, Application No. 08841700.1, dated Jan. 4, 2011.

(56) References Cited

OTHER PUBLICATIONS

European Search Report, Application No. 07717903.4 dated Oct. 23, 2009.
European Search Report, Application No. 08799295.4-2402, PCT/US2008/075565, dated Nov. 9, 2010.
European Search Report, Application No. 08768266.2 dated Jul. 1, 2010.
European Search Report, Application No. 07867402.5 dated Mar. 16, 2010.
European Search Report, Application No. 07810382.7 dated Sep. 14, 2009.
European Search Report, Application No. 06825457.2 dated Sep. 16, 2009.
European Search Report, Application No. 06800599.0 dated Oct. 19, 2009.
European Search Report, Application No. 08798444.9-2402, PCT/US2008/073964, dated Dec. 16, 2010.
European Search Report, Application No. 07753450.1 dated Jan. 12, 2009.
European Search Report, Application No. 09713926.5 dated Jul. 21, 2011.
European Search Report, Application No. 08770974.4, dated Oct. 21, 2011.
European Search Report, Application No. 08713330.2, dated Jul. 22, 2011.
European Search Report, Application No. 11151772-8, dated Feb. 8, 2011.
European Search Report, Application No. 07872618.9 dated Jul. 5, 2010.
European Search Report, Application No. 11151769-4, dated Feb. 8, 2011.
European Search Report, Application No. 07717734.3 dated Nov. 9, 2009.
European Search Report, Application No. 08841700.1 dated Jun. 2, 2010.
European Search Report, Application No. 08796821.0 dated Aug. 4, 2010.
European Search Report, Application No. 06814375.9 dated Oct. 8, 2009.
European Search Report, Application No. 08767439.6 dated May 12, 2010.
European Search Report, Application No. 12185440.0 dated Apr. 12, 2013.
European Search Report, Application No. 07716208.9 dated Nov. 10, 2009.
European Search Report, Application No. 11151771-0, dated Feb. 8, 2011.
European Srch Rpt. 08838376.5 dated Mar. 4, 2011.
European Srch Rpt., 09763590.8 dated Aug. 29, 2011.
European Supplementary Search Report, Application No. 09715064.3 dated May 24, 2011.
Ext. Srch Rpt., Appln. No. 12154246.8 dated Jun. 4, 2012.
Extended EP Search Report Appl. No. 12185438.4 dated Mar. 28, 2013.
Extended EP Search Rpt., Appln. No. 12154353.2 dated Jan. 31, 2013.
Extended EP Search Report 12179592.6 dated Jan. 21, 2013.
Extended EP Search Report Appl. No. 12179595.9 dated Jan. 23, 2013.
Extended EP Srch Rpt., Appln. No. 12154354.0 dated Jan. 28, 2013.
Extended EP Srch Rpt., Appln. No. 12154301.1, dated Jan. 11, 2013.
Extended EP Srch Rpt., Appln. No. 12165748.0.
Extended EP Srch Rpt., Appln. No. 12154352.4, dated Jan. 28, 2013.
Extended EP Srch Rpt., Appln. No. 12165734.0 dated Jan. 11, 2013.
Extended EP Srch Rpt., Appln. No. 12165740.7 dated Jan. 11, 2013.
Extended EP Srch Rpt., Appln. No. 12154351.6 dated Jan. 31, 2013.
Extented EP Search Rpt., Appln. No. 12154349.0 dated Jan. 25, 2013.
Japanese Notification of Reasons for Rejection, Application No. 2010-548904, dated Apr. 1, 2014.
Japanese Notification of Reasons for Rejection 2010529072 dated Jul. 30, 2013.
Japanese Notification of Reasons for Rejection 2010522058 dated Aug. 13, 2013.
Japanese Notification of Reasons for Rejection, 2010548904, dated Sep. 2, 2013.
Japanese Notification Reasons for Rejection 2010-519269 dated Jul. 12, 2013.
Japanese Notification of Reasons for Rejection, 2010548907 dated Sep. 2, 2013.
Japanese Notification of Reasons for Rejection, Application No. 2010-511218, dated Mar. 13, 2014.
Japanese Notification of Reasons for Rejection, Appln. No. 2010-548899, dated Oct. 8, 2013.
Japanese Notification of Reasons for Rejection, Application No. 2011-523144, dated Feb. 6, 2014.
Japanese Notification of Reasons for Rejection, dated Sep. 27, 2013, Appln. No. 2008-549532.
Japanese Notification of Reasons for Rejection, Application No. 2010-506300, dated Mar. 12, 2014.
Japanese Notification of Reasons for Rejection, 2009-519525 dated Jul. 9, 2012.
Japanese Notification of Reasons for Rejection 2009548281 dated Sep. 3, 2013.
Japanese Notification Reasons for Rejection 2009-529212 dated Jul. 19, 2013.
Japanese Notification of ReasonsFor Rejection 2010-524221 dated Jun. 19, 2013.
Japanese Notification Reason for Rejection—EnglishTrans, 2010-512377 dated Jun. 4, 2013.
Japanese Notification of Reasons for Rejection 2009-519525 dated Nov. 1, 2012.
Japanese Office Action dated Feb. 24, 2012, Japanese Patent Application No. 2008-549532.
Japanese Office Action, Application No. 2010-511218 dated Jun. 3, 2013.
Japanese Office Action, Application No. 2008-525107 dated Oct. 19, 2012.
Japanese Office Action dated Jan. 4, 2012, Japanese Patent Application No. 2008-5251070.
Japanese Office Action dated Feb. 22, 2012, Japanese Patent Application No. 2008-549549.
Japanese Office Action, Application No. 2010-506300 dated Apr. 16, 2013.
Japanese Office Action, Application No. 2009-529212 dated Oct. 17, 2012.
Japanese Office Action, Application No. 2009-535366 dated Dec. 21, 2012.
Japanese Office Action 2008-525107 dated Jan. 4, 2011.
Japanese Office Action, Application No. 2009-501495 dated Jul. 27, 2012.
Japanese Office Action dated Feb. 24, 2012, Japanese Patent Application No. 2008-549555.
JP Notification of Reasons for Rejection, Application No. 2012-183280, filed Jan. 3, 2007.
JP Notification of Reasons for Rejection, Appln. No. 2011539528, dated Oct. 25, 2013.
Notice of Allowance and Fees Due in U.S. Appl. No. 12/160,064, filed Jul. 3, 2008, dated Nov. 20, 2009.
Office Action issued in U.S. Appl. No. 12/160,061, filed Jul. 3, 2008, dated Apr. 24, 2009.
Office Action issued in U.S. Appl. No. 12/293,471, filed Oct. 9, 2008, dated Jun. 8, 2010.
Office Action issued in U.S. Appl. No. 12/373,358, filed Feb. 11, 2009, dated Aug. 20, 2010.
Office Action issued in U.S. Appl. No. 12/160,061, filed Jul. 3, 2008, dated Mar. 12, 2010.
Office Action issued in U.S. Appl. No. 12/160,034, filed Jul. 3, 2008, dated Jun. 7, 2010.
Office Action issued in U.S. Appl. No. 12/083,067, filed Jun. 20, 2008, dated Jul. 8, 2010.

(56) References Cited

OTHER PUBLICATIONS

Office Action issued in U.S. Appl. No. 12/160,061, filed Jul. 3, 2008, dated Oct. 30, 2009.
Office Action issued in U.S. Appl. No. 12/442,018, filed Mar. 27, 2009, dated Apr. 15, 2010.
Office Action issued in U.S. Appl. No. 12/160,064, filed Jul. 3, 2008, dated Aug. 10, 2009.
PCT International Preliminary Report on Patentability, PCT/US2008/071532 filed Jul. 30, 2008, dated Feb. 2, 2010.
PCT International Preliminary Report on Patentability, PCT/US2008/066870 filed Jun. 13, 2008, dated Dec. 17, 2009.
PCT International Preliminary Report on Patentability, PCT/US2008/005503 filed Apr. 29, 2008, dated Nov. 3, 2009.
PCT International Preliminary Report on Patentability, PCT/US2006/035100 filed Sep. 11, 2006, dated Mar. 18, 2008.
PCT International Preliminary Report on Patentability, PCT/US2009/038214 filed Mar. 25, 2009, dated Jun. 16, 2011.
PCT International Preliminary Report on Patentability, PCT/US2009/065072 filed Nov. 19, 2009, dated Jun. 3, 2011.
PCT International Preliminary Report on Patentability, PCT/US2006/029889 filed Jul. 31, 2006, dated Feb. 5, 2008.
PCT International Preliminary Report on Patentability, PCT/US2009/035463 filed Feb. 27, 2009, dated Aug. 31, 2010.
PCT International Preliminary Report on Patentability, PCT/US2009/035482 filed Feb. 27, 2009, dated Aug. 31, 2010.
PCT International Preliminary Report on Patentability, PCT/US2010/057758 filed Nov. 23, 2010, dated Jun. 7, 2012.
PCT International Preliminary Report on Patentability, PCT/US2007/015892 filed Jul. 12, 2007, dated Jan. 13, 2009.
PCT International Preliminary Report on Patentability, PCT/US2008/001157 filed Jan. 29, 2008, dated Aug. 4, 2009.
PCT International Preliminary Report on Patentability, PCT/US2007/000103 filed Jan. 3, 2007, dated Jul. 8, 2008.
PCT International Preliminary Report on Patentability, PCT/US2008/075565 filed Sep. 8, 2008, dated Mar. 9, 2010.
PCT International Preliminary Report on Patentability, PCT/US2007/000159 filed Jan. 3, 2007, dated Jul. 8, 2008.
PCT International Preliminary Report on Patentability, Application No. PCT/US2011/060838, filed Nov. 15, 2011.
PCT International Preliminary Report on Patentability, PCT/US2007/000024 filed Jan. 3, 2007, dated Jul. 8, 2008.
PCT International Preliminary Report on Patentability, PCT/US2007/009910 filed Apr. 24, 2007, dated Oct. 28, 2008.
PCT International Preliminary Report on Patentability, PCT/US2007/020215 filed Sep. 17, 2007, dated Mar. 24, 2009.
PCT International Preliminary Report on Patentability, PCT/US2007/023660 filed Nov. 1, 2007, dated May 5, 2009.
PCT International Preliminary Report on Patentability, PCT/US2008/007196 filed Jun. 9, 2008, dated Dec. 11, 2009.
PCT International Preliminary Report on Patentability, PCT/US2008/072081 filed Aug. 4, 2008, dated Feb. 9, 2010.
PCT International Preliminary Report on Patentability, PCT/US2009/035470 filed Feb. 27, 2009, dated Aug. 31, 2010.
PCT International Preliminary Report on Patentability, PCT/US2011/034451 filed Apr. 29, 2011, dated Nov. 15, 2012.
PCT International Preliminary Report on Patentability, PCT/US2007/006824 filed Mar. 19, 2007, dated Sep. 23, 2008.
PCT International Preliminary Report on Patentability, PCT/US2006/038824 filed Oct. 4, 2006, dated Apr. 9, 2008.
PCT International Preliminary Report on Patentability, PCT/US2010/025173 filed Feb. 24, 2010, dated Sep. 9, 2011.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2008/073964 filed Aug. 22, 2008, dated Feb. 24, 2010.
PCT International Search Report and the Written Opinion, PCT/US2008/07196 filed Jun. 9, 2008, dated Nov. 19, 2008.
PCT International Search Report and the Written Opinion, PCT/US2008/05503 filed Apr. 29, 2008, dated Sep. 25, 2008.
PCT International Search Report and the Written Opinion, PCT/US2007/09910 filed Apr. 24, 2007, dated Feb. 13, 2008.
PCT International Search Report and the Written Opinion, PCT/US2007/006824 filed Mar. 19, 2007, dated May 14, 2008.
PCT International Search Report and the Written Opinion, PCT/US2012/28016 filed Mar. 7, 2012, dated Aug. 3, 2012.
PCT International Search Report and the Written Opinion, PCT/US2012/020911 filed Jan. 11, 2012, dated Apr. 25, 2012.
PCT International Search Report and the Written Opinion, PCT/US2007/00159 filed Jan. 3, 2007, dated Apr. 11, 2008.
PCT International Search Report and the Written Opinion, PCT/US2007/00103 filed Jan. 3, 2007, dated Dec. 3, 2007.
PCT International Search Report and the Written Opinion, PCT/US2006/29889 filed Jul. 31, 2006, dated Jul. 10, 2007.
PCT International Search Report and the Written Opinion, PCT/US2008/01157 filed Jan. 29, 2008, dated Aug. 7, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2007/15892 filed Jul. 12, 2007, dated Sep. 30, 2008.
PCT International Search Report and the Written Opinion, PCT/US2009/53586 filed Aug. 12, 2009, dated Oct. 28, 2009.
PCT International Search Report and the Written Opinion, PCT/US2008/71532 filed Jul. 30, 2008, dated Apr. 17, 2009.
PCT International Search Report and the Written Opinion, PCT/US2007/006824 filed Mar. 19, 2007, dated Mar. 3, 2008.
PCT International Search Report and the Written Opinion, PCT/US2007/00024 filed Jan. 3, 2007, dated Nov. 5, 2007.
PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007.
PCT International Search Report and the Written Opinion, PCT/US2008/84821 filed Nov. 26, 2008, dated Feb. 17, 2009.
PCT International Search Report and the Written Opinion, PCT/US2009/46999 filed Jun. 11, 2009, dated Nov. 23, 2009.
PCT International Search Report and the Written Opinion, PCT/US2009/35458 filed Feb. 27, 2009, dated Jul. 28, 2009.
PCT International Search Report and the Written Opinion, PCT/US2012/060225 filed Oct. 15, 2012, dated Jan. 7, 2013.
PCT International Search Report and the Written Opinion, PCT/US2009/38214 filed Mar. 25, 2009, dated Aug. 14, 2009.
PCT International Search Report and the Written Opinion, PCT/US2009/35482 filed Feb. 27, 2009, dated Jul. 17, 2009.
PCT International Search Report and the Written Opinion, PCT/US2009/35470 filed Feb. 27, 2009, dated Jun. 16, 2009.
PCT International Search Report and the Written Opinion, PCT/US2008/73964 filed Aug. 22, 2008, dated Dec. 24, 2008.
PCT International Search Report and the Written Opinion, Application No. PCT/US11/60838, filed Nov. 15, 2011.
PCT International Search Report and the Written Opinion, PCT/US2008/81294 filed Oct. 27, 2008, dated Mar. 26, 2009.
PCT International Search Report and the Written Opinion, PCT/US2008/79482 filed Oct. 10, 2008, dated Dec. 22, 2008.
PCT International Search Report and the Written Opinion, PCT/US2008/72081 filed Aug. 4, 2008, dated Jan. 14, 2009.
PCT International Search Report and the Written Opinion, PCT/US2009/35463 filed Feb. 27, 2009, dated Aug. 13, 2009.
PCT International Search Report and the Written Opinion, PCT/US2008/66870 filed Jun. 13, 2008, dated Nov. 10, 2008.
PCT International Search Report and the Written Opinion, PCT/US2008/75565 filed Sep. 8, 2008, dated Dec. 9, 2008.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.

(56) References Cited

OTHER PUBLICATIONS

PCT Intr Srch Rpt., Written Opinion, PCT/US12/62853, dated Mar. 14, 2013.
PCT Invitation to Pay Additional Fees, PCT/US2012/028016 filed Mar. 7, 2012, dated May 29, 2012.
PCT Search Report and Written Opinion, PCT/US13/22492, dated May 20, 2013.
PCT Search Report and Written Opinion PCT/US2012/68736, dated Apr. 8, 2013.
PCT Search Report and Written Opinion PCT/US2012/67651, dated May 13, 2013.
PCT Srch Rpt. Wrtn. Opin, PCT-US12-69484, dated Apr. 29, 2013.
PCT Srch Rpt., Written Opinion, PCT/US11/29348, dated Jun. 3, 2011.
PCT Srch Rpt., Wrtn Opin, PCT/US11/41046, dated Mar. 5, 2012.
PCT Srch Rpt., Wrtn Opin PCT/US12/62853 dated Mar. 14, 2013.
PCT Srch Rpt., Wrtn Opin PCT/US13/538930 dated Feb. 10, 2012.
PCT Written Opinion PCT/US13/538930 dated May 23, 2013.
Ahmad, A. et al., "Distant Metastases of Nasopharyngeal Carcinoma: A Study of 256 Male Patients," Journal of Surgical Oncology, 1986, pp. 194-197, vol. 33.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Akahoshi, M. et al., "Myeloproliferative Disorders Terminating in Acute Megakaryoblastic Leukemia with Chromosome 3q26 Abnormality," Cancer, 1987, pp. 2654-2661, vol. 60.
Akao, Y. et al., "let-7 MicroRNA Functions as a Potential Growth Suppressor in Human Colon Cancer Cells," Biol. Pharm. Bull., May 2006, pp. 903-906, vol. 29, No. 5.
Alberts, B. et al., Molecular Biology of The Cell, 3rd Edition, 1994, p. 465.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Ambros, MicroRNA Pathways in Flies and Worms: Growth, Death, Fat, Stress, and Timing, Nature, 2004, vol. 431, pp. 350-355.
Ambros, V. et al., "A Uniform System for MicroRNA Annotation," RNA, 2003, pp. 277-279, vol. 9.
Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.
Aqeilan, R. I. et al., "Targeted Deletion of WWOX Reveals a Tumor Suppressor Function," PNAS, Mar. 2007, pp. 3949-3954, vol. 104, No. 10.
Arata, et al., Cdk2-dependent and -independent Pathways in E2F-mediated S Phase Induction, J. Biol. Chem, 2000.
Asangani, IA,, et al., MicroRNA-21 (miR-21) post-transcriptionally downregulates tumor suppressor Pdcd4 and stimulates invasion, intravasation and metastasis in colorectal cancer, Oncogene, 2008, vol. 27, pp. 2128-2136.
Attwooll, et al., The E2F family: specific functions and overlapping interests, EMBO, 2004.
Baira, E. et al., "Ultraconserved Elements: Genomics, Function and Disease," RNA Biology, Jul. 2008, pp. 132-134, vol. 5, No. 3.
Bakkus, M. et al., "MicroRNA Expression Analysis in Multiple Myeloma Plasma Cells and Cell Lines by a Quantitative Real-Time PCR Approach," Blood, 2007, p. 729A, vol. 110, No. 11, Abstract.
Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.
Bao, B. et al. Anti-Tumor Activity of a Novel Compound, PLOS One, 2011, vol. 6, Issue 3, pp. 1-12.
Barad, O. et al., "MicroRNA Exrpession Detected by Oligonucleotide Microarrays: System Establishment and Expression Profiling in Human Tissues," Genome Research, 2004, pp. 2846-2494, vol. 14.
Bartel, D. P., "MicroRNAs: Target Recognition and Regulatory Functions," Cell, Jan. 2009, pp. 215-233, vol. 136.
Bartel, MicroRNAs: Genomics, Biogenesis, Mechanism, and Function, Cell, vol. 116, 2004, pp. 281-297.
Basu, et al., MicroRNA-375 and MicroRNA-221:Potential Noncoding RNAs Associated with Antiproliferative Activity of Benzyl Isothiocyanate in Pancreatic Cancer, Croce, Genes & Cancer, 2011, pp. 108-119.
Baudhuin, L.M. et al., "Use of Microsatellite Instability and Immunohistochemistry Testing for the Identification of Individuals at Risk for Lynch Syndrome," Fam. Cancer, 2005, pp. 255-265, vol. 4, No. 3.
Bednarek, A. K. et al., "WWOX, the FRA16D Gene, Behaves as a Suppressor of Tumor Growth," Cancer Research, Nov. 2001, pp. 8068-8073, vol. 61.
Bejenaro, etal., "Ultraconserved Elements in the Human Genome," Electronic Suppl. Data, Science, 2004.
Bejerano, Computational Screening of Conserved Genomic DNA-Nature Methods, 2005, vol. 2, No. 7, pp. 535-545.
Bejerano, G. et al., "Ultraconserved Elements in the Human Genome," Science, May 2004, pp. 1321-1325, vol. 304.
Belinsky, et al., Inhibition of DNA Methylation and Histone Deacetylation Prevents Murine Lung Cancer, Cancer Research 63, 2004, pp. 7089-7093.
Bell, D. A., "Origins and Molecular Pathology of Ovarian Cancer," Modern Pathology, 2005, pp. S19-S32, vol. 18.
Bendoraite, et al, Regulation of miR-200 family microRNAs and ZEB transcription factors in ovarian cancer: evidence supporting a mesothelial-toepithelial transition, Gyneol Oncol, 2010, vol. 116, pp. 117-125.
Bichi, R. et al., "Human Chronic Lymphocytic Leukemia Modeled in Mouse by Targeted TCL1 Expression," PNAS, May 2002, pp. 6955-6960, vol. 99, No. 10.
Bloomston, et al., Identification of Molecular Markers Specific for Pancreatic Neuroendocrine Tumors by Genetic Profiling of Core Biopsies, Ann. Surg. Oncol. 2004, vol. 11, 4, pp. 413-419.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blow, Replication licensing—defining the proliferative state, Cell Biol, 2002.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Boominathan, L., The Tumor Suppressors p53-p63 and p72, PLOS ONE, May 2010, vol. 5, Issue 5, pp. 1-13.
Braun et al., "p53-Responsive MicroRNAs 192 and 215 are Capable of Inducing Cell Cycle Arrest," Cancer Research, 2008, pp. 10094-10104, vol. 68.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, A. et al., "Identification of Metastasis-Related MicroRNAs in Hepatocellular Carcinoma," Hepatology, Mar. 2008, pp. 897-907, vol. 47, No. 3.
Budhu, et al., Prediction of venous metastases, recurrence, and prognosis in hepatocellular carcinoma based on a unique immune response signature of the liver microenvironment, Cancer Cell, 2006, vol. 10, 2, pp. 99-111.
Butz, H. et al., "Down-Regulation of Wee1 Kinase by a Specific Subset of MicroRNA Sporadic Pituitary Adenomas," Journal of Clinical Endocrinol Metab, Oct. 2010, pp. E181-E191, vol. 95, No. 10.
Caldas, C. et al., "Sizing Up miRNAs as Cancer Genes," Nature Medicine, Jul. 2005, pp. 712-714, vol. 11, No. 7.

(56) References Cited

OTHER PUBLICATIONS

Calin, G. A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "Ultraconserved Regions Encoding ncRNAs are Altered in Human Leukemias and Carcinomas," Cancer Cell, Sep. 2007, pp. 215-229, vol. 12.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.
Calin, G. A. et al., "MicroRNA Signatures in Human Cancers," Nature Reviews Cancer, Nov. 2006, pp. 857-866, vol. 6.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.
Cannistra, S.A., "Cancer of the Ovary," The New England Journal of Medicine, 2004, pp. 2519-2529, vol. 351, No. 25.
Castoldi, M. et al., "A Sensitive Array for MicroRNA Expression Profiling (miChip) Based on Locked Nucleic Acids (LNA)," RNA, 2006, pp. 913-920, vol. 12.
Chambers, et al., Dissemination and Growth of Cancer Cells in Metastatic Sites, Nat. Rev. Cancer, 2002, vol. 2, pp. 563-572.
Chan, et al., Concordant and Discordant Regulation of Target Genes by miR-31 and Its Isoforms, PLOS One, 2013, vol. 8, pp. 1-11.
Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.
Chang, T. C., et al., Transactivation of miR-34a by p53, Molecular Cell 26, pp. 745-752, 2007.
Chang, T.-C. et al., "Widespread MicroRNA Repression by Myc Contributes to Tumorigenesis," Nat Genet., Jan. 2008, pp. 43-50, vol. 40, No. 1.
Chen, C.-Z. et al., "MicroRNAs as Regulators of Mammalian Hematopoiesis," Seminars in Immunology, 2005, pp. 155-165, vol. 17.
Chen, et al., Expanded Polyglutamine-Binding Peptoid as a Novel Therapeutic Agent for Treatment of Huntington's Disease, Chemistry Biology, 2011, vol. 18, pp. 1113-1125.
Chen, et al., Real-time quantification of microRNAs by stem-loop RT-PCR, Nucleic Acids, 33, 2005, e179.
Chen, et al., Downregulation of miR-221/222 sensitizes glioma cells to tempzolomide by regulating apoptosis independently of p53 status, Onocolgy Reports, 2012, vol. 27, pp. 854-860.
Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.
Chiesa, et al., Fenretinide (4-HPR) in Chemoprevention of Oral Leukoplakia, Journal of Cellular Biochemistry, Supplement, 17F, 1993, pp. 255-261.
Chiesa, et al., Prevention of Local Relapses and New Localisations of Oral Leukoplakias with the Synthetic Retinoid Fenretinide (4-HPR). Preliminary Results, 1992, Oral Oncol, Eur. J. Cancer, vol. 28B, No. 2, pp. 97-102.

Chiesa, et al., Randomized trial of fenretinide (4-HPR) to prevent recurrences, new localizations and carcinomas in patients operated on for oral leukoplakia: Long-term results, Int. J. Cancer, 2005, No. 115, pp. 625-629.
Chim, S.S.C. et al., "Detection and Characterization of Placental MicroRNAs in Maternal Plasma," Clinical Chemistry, 2008, pp. 482-490, vol. 54, No. 3.
Chun-Zhi, et al., MicroRNA-221 and microRNA-222 regulate gastric carcinoma cell proliferation and radioresistance by targeting PTEN, BMC Cancer, 2010, gastric, vol. 10, pp. 1-10.
Ciafre, S. A. et al., "Extensive Modulation of a Set of MicroRNAs in Primary Glioblastoma," Biochemical and Biophysical Research Communications, 2005, pp. 1351-1358, vol. 334.
Cillo, et al., The critical issue of hepatocellular carcinoma prognostic classification: which is the best tool available, J. Hepatol., 2004, vol. 40, 1, pp. 124-131.
Cimmino, A. et al., "miR-15 and miR-16 Induce Apoptosis by Targeting BCL2," PNAS, Sep. 2005, pp. 13944-13949, vol. 102, No. 39.
Cimmino, A. et al., Corrections to "miR-15 and miR-16 Induce Apoptosis by Targeting BCL2," PNAS, Feb. 2006, pp. 2464-2465, vol. 103, No. 7.
Costa, et al., Prospects of Chemoprevention of Human Cancers with the Synthetic Retinoid Fenretinide1, Cancer Research (Suppl.,), 1994, No. 54, pp. 2032s-2037s.
Costinean, S. et al., "Pre-B Cell Proliferation and Lymphoblastic Leukemia/ High-Grade Lymphoma in Eμ-miR155 Transgenic Mice," PNAS, May 2006, pp. 7024-7029, vol. 103, No. 18.
Cowgill, The genetics of pancreatic cancer Am. J. Surg, 2003, vol. 186, 3, pp. 279-286.
Croce, C. M. et al., "Role of FHIT in Human Cancer," Journal of Clinical Oncology, May 1999, pp. 1618-1624, vol. 17, No. 5.
Croce, C. M. et al., "miRNAs, Cancer, and Stem Cell Division," Cell, 2005, pp. 6-7, vol. 36.
Croce, C. M., "Causes and Consequences of MicroRNA Dysregulation in Cancer," Nature Reviews Genetics, Oct. 2009, pp. 704-714, vol. 10.
Croce, C. M., "Oncogenes and Cancer," The New England Journal of Medicine, Jan. 2008, pp. 502-511, vol. 358, No. 5.
Cui, S. et al., "MicroRNAs that Underlie Ovarian Cancer Development and Response to Chemotherapy," 98th AACR Annual Meeting, Apr. 14-18, 2007, Los Angeles, CA.
Dahiya, N. et al., "MicroRNA Expression and Identification of Putative miRNA Targets in Ovarian Cancer," Plos One, Jan. 2008, pp. 1-11, vol. 3, No. 6.
Dalmay, T. et al., "MicroRNAs and the Hallmarks of Cancer," Oncogene, 2006, pp. 6170-6175, vol. 25.
Davies, B.R. et al., "AZD6244 (ARRY-142886), a Potent Inhibitor of Mitogen-Activated Protein Kinase/Extracellular Signal-Regulated Kinase Kinase ½ Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.
Davies, F. E. et al., "Insights into the Multistep Transformation of MGUS to Myeloma Using Microarray Expression Analysis," Blood, Dec. 2003, pp. 4504-4511, vol. 102, No. 13.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Delott, et al., CDX2 Is a Useful Marker of Intestinal-Type Differentiation Arch. Pathol. Lab, Med, 2005 vol. 129, 9, pp. 1100-1105.
Desai, et al., Development and In Vitro-In Vivo Evaluation of Fenretinide-Loaded Oral Mucoadhesive Patches for Site-Specific Chemoprevention of Oral Cancer, Pharm Res., 2011, No. 28, pp. 2599-2609.
DiGiovanna, Retinoids for the future: Oncology, Retinoids of the Future, vol. 27, 1992, pp. S34-S37.
Dignam, et al., Accurate transcription initiation by RNA polymerase D in a soluble extract from isolated mammalian nuclei, Nucleic Acids Res., 11, 1983, pp. 1475-1489.

(56) References Cited

OTHER PUBLICATIONS

Dohner, H. et al., "Genomic Aberrations and Survival in Chronic Lymphocytic Leukemia," The New England Journal of Medicine, Dec. 2000, pp. 1910-1916, vol. 343, No. 26.

Druck, etal., "FHIT," Atlas of Genetics and Cytogenetics in Oncology and Haematology, 2007, pp. 171-178, vol. 2.

Ehrich, et al., Quantitative High-Throughput Analysis of DNA Methylation Patterns by Base-Specific Cleavage and Mass Spectrometry, vol. 102, 2005, pp. 15785-15790.

Eiriksdottir, G. et al., "Mapping Loss of Heterozygosity at Chromosome 13q: Loss at 13q12-q13 is Associated with Breast Tumour Progression and Poor Prognosis," European Journal of Cancer, 1998, pp. 2076-2081, vol. 34, No. 13.

Eis, P. S. et al., "Accumulation of miR-155 and BIC RNA in Human B Cell Lymphomas," PNAS, Mar. 2005, pp. 3627-3632, vol. 102, No. 10.

Esquela-Kerscher "OncomiRs: The Discovery and Progress of MicroRNAs in Cancers," Molecular Cancer, Sep. 2007, pp. 259-269, vol. 6, No. 4.

Esquela-Kerscher, A. et al., "Oncomirs—MicroRNAs with a Role in Cancer," Nature Reviews:Cancer, Apr. 2006, pp. 259-269, vol. 6.

Eychene, A. et al., "A New MAFia in Cancer," Nature Reviews Cancer, Sep. 2008, pp. 683-693, vol. 8.

Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.

Fabbri, M. et al., "MicroRNAs," The Cancer Journal, Jan./Feb. 2008, pp. 1-6, vol. 14, No. 1.

Fabbri, M. et al., "WWOX Gene Restoration Prevents Lung Cancer Growth In Vitro and In Vivo," PNAS, Oct. 2005, pp. 15611-15616, vol. 102, No. 43.

Farazi, et al., MicroRNA Sequence and Expression Analysis in Breast Tumors by Deep Sequencing, AACR, 71(13), Jul. 1, 2011, pp. 4443-4453.

Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.

Feng, G. et al., "Elevated Serum-Circulating RNA in Patients with Conventional Renal Cell Cancer," Anticancer Research, 2008, pp. 321-326, vol. 28.

Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.

Fong, Y. et al., "Muir-Torre-Like Syndrome in FHIT-Deficient Mice," PNAS, Apr. 2000, pp. 4742-4747, vol. 97, No. 9.

Ford, L.P., "A MicroRNA Expression Signature of Human Solid Tumors Defines Cancer Gene Targets," Leukemia Research, 2006, pp. 511-513, vol. 30.

Fornari, et al., MiR-221 controls CDKNIC/p57 and CDKNIB/p27 expression in human hepatocellular carcinoma, Oncogene 2008, vol. 27, pp. 5651-5661.

Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.

Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.

Fulci, et al., Quantitative Technologies Establish a Novel MicroRNA Profile of Chronic Lymphocytic Leukemia, Blood, Jun. 1, 2007, vol. 109, pp. 4944-4951.

Gailiun, M., "Single MicroRNA Causes Cancer in Transgenic Mice," Research Communications, The Ohio State University, Apr. 2006, pp. 1-3.

Gang, M. et al., "Expression of Programmed Cell Death 4 and Its Clinicopathological Significance in Human Pancreatic Cancer," Abstract, 2005, pp. 597-600, vol. 27.

Garcea, et al., Molecular prognostic markers in pancreatic cancer, A systematic review, Eur. J. Cancer, 2005, vol. 4, 15, pp. 2213-2236.

Garofalo, et al., MiR-221&222 enchance migration and invasiveness of NSCLC and hepatocarcinoma cells by targeting PTEN tumor suppressor, AACR, 2009.

Garofalo, et al., miR221/222 in Cancer: Their Role in Tumor Progression and Response to Therapy, Current Molecular Medicine, 2012, 12, pp. 27-33.

Garofalo, M. et al., "MicroRNA Signatures of TRAIL Resistance in Human Non-Small Cell Lung Cancer," Oncogene, 2008, pp. 3845-3855, vol. 27.

Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.

Garzon et al., MicroRNA expression and function in cancer, Trend Mol Med, vol. 12, 2006, pp. 580-587.

Garzon et al., MicroRNA signatures associated with cytogenetics and prognosis in acute myeloid leukemia; Blood, Mar. 15, 2008, vol. 111, No. 6.

Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.

Garzon, R. et al., "MicroRNA Expression and Function in Cancer," TRENDS in Molecular Medicine, Oct. 2006, pp. 580-587, vol. 12, No. 12.

Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.

Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.

Garzon, R. et al., "MicroRNA Fingerprints During Human Megakaryocytopoiesis," PNAS, Mar. 2006, pp. 5078-5083, vol. 103, No. 13.

Ghaneh, et al., Molecular prognostic markers in pancreatic cancer, J. Hepatobiliary, Pancreat. Surg., 2002, vol. 9, pp. 1-11.

Ghoshal, et al., Up-regulation of oncogenic microRNAs and down-regulation of their tumor suppressor targets play a casual role in the initiation of hepatocarcinogenesis in mice fed choline-deficient and amino acid defined diet, AACR, 2008.

Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.

Goel, A., et al., A Novel Mechanism for Aspirin Mediated Growth Inhibition, Clin Cancer Res, 2003, vol. 9, pp. 383-390.

Gourley, C. et al., "WWOX Gene Expression Abolishes Ovarian Cancer Tumorigenicity In Vivo and Decreases Attachment to Fibronectin via Integrin α3," Cancer Research, Jun. 2009, pp. 4835-4842, vol. 69, No. 11.

Greenbaum, D. et al., "Comparing Protein Abundance and mRNA Expression Levels on a Genomic Scale," Genome Biology, 2003, pp. 117.1-117.8, vol. 4, Issue 9.

Gregory, et al., MicroRNA Biogenesis and Cancer, Cancer Res, 2005, vol. 65, 9, pp. 3509-3512.

Gregory, et al., The Microprocessor complex mediates the genesis of microRNAs, Nature, 432, 2004, pp. 235-240.

Grier, D.G. et al., "The Pathophysiology of HlX Genes and Their Role in Cancer," Journal of Pathology, 2005, pp. 154-171, vol. 205.

Griffiths-Jones, S. et al., "miRBase: MicroRNA Sequences, Targets and Gene Nomenclature," Nucleic Acids Research, 2006, pp. D140-D144, vol. 34.

Griffths-Jones, S. et al., "miRBase: Tools for MicroRNA Genomics," Nucleic Acids Research, 2008, pp. D154-D157, vol. 36.

Griffths-Jones, S., "The MicroRNA Registry," Nucleic Acids Research, 2004, pp. D109-D111, vol. 32.

Gu, et al., The t(4;ll) Chromosome Translocation of Human Acute Leukemias Fuses the ALL-7 Gene, Related to *Drosophila trithorax*, to the AF-4 Gene, Cell 71, 1992, pp. 701-709.

Guenther, et al., Global and Hox-specific roles for the MLL1 methyltransferase, Proc. Natl. Acad. Sci., 102, 2005, pp. 8603-8608.

Guerrette, S. et al., "Interactions of Human hMSH2 with hMSH3 and hMSH2 with hMSH6: Examination of Mutations Found in

(56) References Cited

OTHER PUBLICATIONS

Hereditary Nonpolyposis Colorectal Cancer," Molecular and Cellular Biology, Nov. 1998, pp. 6616-6623, vol. 18, No. 11.
Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Habbe, et al., MicroRNA miR-155 is a biomarker of early pancreatic neoplasia, Cancer Biol Therapy, 2009, pp. 340-346.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.
He, H. et al., "The Role of MicroRNA Genes in Papillary Thyroid Carcinoma," PNAS, Dec. 2005, pp. 19075-19080, vol. 102, No. 52.
He, L. et al., "A MicroRNA Polycistron as a Potential Human Oncogene," Nature, Jun. 2005, pp. 828-833, vol. 435.
He, X. et al., "MicroRNA and Esophageal Carcinoma," Journal of Nanjing Medical University, 2007, pp. 201-206, vol. 21, No. 4.
Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.
Hezel, et al., Genetics and biology of pancreatic ductal adenocarcinoma, Genes Dev., 2006, vol. 20, pp. 1218-1249.
Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.
Holpuch, et al., Evaluation of a mucoadhesive fenretinide patch for local intraoral delivery: a strategy to reintroduce fenretinide for oral cancer chemoprevention, Carcinogenesis, 2012, vol. 33, No. 5, pp. 1098-1105.
Holpuch, et al., Nanoparticles for Local Drug Delivery to the Oral Mucosa: Proof of Principle Studies, Pharm Res. 2010, No. 27, pp. 1224-1236.
Holpuch, et al., Optimizing therapeutic efficacy of chemopreventive agents: A critical review of delivery strategies in oral cancer chemoprevention clinical trials, Journal of Carcinogenesis, 2011, pp. 1-12.
Hu, et al., A miR-200 microRNA cluster as prognostic marker in advanced ovarian cancer, Gynecol Oncol, 2009, vol. 114, pp. 457-464.
Huang, et al., Evaluation of predictive value of CLIP, Okuda, TNM and JIS staging systems for hepatocellular carcinoma patients undergoing surgery, J. Gastroenterol Hepatol, 2005, vol. 20, 5, pp. 765-771.
Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.
Hudlebusch, H. et al., "Expression of HOXA Genes in Patients with Multiple Myeloma," Leukemia & Lymphoma, Jun. 2004, pp. 1215-1217, vol. 45, No. 6.
Hutvagner, et al., A MicroRNA in a Multiple Turnover RNAi Enzyme Complex, Science, 2002, vol. 297, 5589, pp. 2056-2060.
Iizuka, et al., Oligonucleotide microarray for prediction of early intrahepatic, Lancet, 2003, vol. 361, 9361, pp. 923-929.
Iliopoulos, D. et al., "Inhibition of Breast Cancer Growth InVitro and In Vivo: Effect of Restoration of WWOX Expression," Clin. Cancer Research, Jan. 2007, pp. 268-274, vol. 13, No. 1.
Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.

Iorio et al., MicroRNAs in Cancer: Small Molecules With a Hugh Impact, Journal of Clinical Oncology, vol. 27, Dec. 1, 2009, pp. 5848-5856.
Iorio, et al., Causes and consequences of microRNA Dysregulation, Cancer Journal, 2012, vol. 18, pp. 215-222.
Iorio, et al., MicroRNA dysregulation in cancer: diagnostics, monitoring and therapeutics. A comprehensive review. EMBO Mol Med 4, pp. 143-159.
Iorio, et al., MicroRNA Involvement in Human Cancer, Advance Access, 2012, pp. 1126-1133.
Iorio, M. V. et al., "MicroRNA Signatures in Human Ovarian Cancer," Cancer Research, Sep. 2007, pp. 8699-8707, vol. 67, No. 18.
Iorio, M. V. et al., "MicroRNA Gene Expression Deregulation in Human Breast Cancer," Cancer Research, Aug. 2005, pp. 7065-7070, vol. 65, No. 16.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.
Izzotti, A. et al., Relationships of MicroRNA Expression in Mouse, FASEB Journal, vol. 23, Sep. 2009, pp. 3243-3250.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jacobs, I.J. et al., "Progress and Challenges in Screening for Early Detection of Ovarian Cancer," Molecular & Cellular Proteomics, 2004, pp. 355-366, vol. 3.
Janis, L.S., Ephrin-A Binding and EphA Receptor Expression Delineate the Matrix Compartment of the Striatum, The Journal of Neuroscience, Jun. 15, 1999, 19(12), pp. 4962-4971.
Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.
Jazbutyte, V. et al., "MicroNRA-21: From Cancer to Cardiovascular Disease," Current Drug Targets, Abstract, 2010, pp. 926-935, vol. 11.
Jemal, A. et al., "Cancer Statistics," CA Cancer J. Clin., 2008, pp. 71-96, vol. 58, No. 2.
Jemal, et al., Cancer Statistics, Cancer Stats vol. 57, 2007, pp. 43-66.
Ji, J. et al., "MicroRNA Expression, Survival, and Response to Interferon in Liver Cancer," The New England Journal of Medicine, Oct. 2009, pp. 1437-1447, vol. 361, No. 15.
Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.
Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.
Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.
Jiang, J. et al., "Real-Time Expression Profiling of MicroRNA Precursors in Human Cancer Cell Lines," Nucleic Acids Research, 2005, pp. 5394-5403, vol. 33, No. 17.
Johansson, et al., Hematologic malignancies with t(4;11)(q21;q23) a cytogenetic, morphologic, immunophenotypic and clinical study of 183 cases, Leukemia, 12, 1998, pp. 779-787.
John, B. et al., "Human MicroRNA Targets," PLOS Biology, Nov. 2004, pp. 1862-1879, vol. 2, Issue 11.
Johnson, S. M. et al., "RAS is Regulated by the let-7 MicroRNA Family," Cell, Mar. 2005, pp. 635-647, vol. 120.
Jover, et al., The Efficacy of adjuvant chemotherapy with 5-fluorouracil in colorectal cancer depends on the mismatch repair status, European Journal of Cancer, Pergamon Press, Oxford, GB, vol. 45, No. 3, Feb. 1, 2009, pp. 365-373.
Kan, et al., Elevated Levels of Circulating MicroRNA, BMC, Cancer, 2012, vol. 12, pp. 2-9.

(56) References Cited

OTHER PUBLICATIONS

Kane, M.F. et al., "Methylation of the hMLH1 Promoter Correlates with Lack of Expression of hMLH1 in Sporadic Colon Tumors and Mismatch Repair-Defective Human Tumor Cell Lines," Cancer Research, 1997, pp. 808-811, vol. 57.
Kanzo (Liver), 2006, vol. 47, No. Suppl. 1, pA19, #S2-11.
Kanzo (Liver), 2006, vol. 47, No. Suppl. 2, pA381, #KanW14-5.
Kawasaki, H. et al., "MicroRNA-196 Inhibits HOXB8 Expression in Myeloid Differentiation of HL60 Cells," Nucleic Acids Symposium Series, 2004, pp. 211-212, No. 48.
Kelly, L.M. et al., "CT53518, A Novel Selective FLT3 Antagonist for the Treatment of Acute Myelogenous Leukemia (AML)," Cancer Cell, Jun. 2002,pp. 421-432, vol. 1.
Kim, et al., FHIT Protein Enhances Paclitaxel-Induced Apoptosis, Int. J. Cancer, vol. 118, pp. 1692-1698.
Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.
Kim, MicroRNA Biogenesis: Coordinated Cropping and Dicing, Nature Rev. Mol. Cell Bio, vol. 6, 2005, pp. 376-385.
Kim, Processing of intronic microRNAs, EMBO, 2007, vol. 26, 3, pp. 775-783.
Kluiver, et al., BIC and miR-155 are highly expressed in Hodgkin, primary mediastinal and diffuse large B cell lymphomas, J. Pathol., 2005, 207, 2, pp. 243-249.
Kluiver, et al., Lack of BIC and MicroRNA miR-155 Expression in Primary Cases of Burkitt Lymphoma, Cancer, 2006, vol. 45, 2, pp. 147-153.
Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.
Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.
Kozomara, A. et al., "miRBase: Integrating MicroRNA Annotation and Deep-Sequencing Data," Nucleic Acids Research, 2011, pp. D152-D157, vol. 39.
Krek, A. et al., "Combinatorial MicroRNA Target Predictions," Nature Genetics, May 2005, pp. 495-500, vol. 37, No. 5.
Kudo, et al., Prognostic staging system for hepatocellular carcinoma (CLIP score): its value and limitations, and a proposal for a new staging system, the Japan Integrated Staging Score (JIS score), J. Gastroenterol, 2003, vol. 38, 3, pp. 207-215.
Kulshreshtha, et al., A MicroRNA Signature of Hypoxia, Mol. Cell Biol., 2006, pp. 1395-1306.
Kulshreshtha, R. et al., "A MicroRNA Signature of Hypoxia," Molecular and Cellular Biology, Mar. 2007, pp. 1859-1867, vol. 27, No. 5.
Kuroki, et al., "Genetic Alterations of the Tumor Suppressor Gene WWOX in Esophageal Squamous Cell Carcinoma," Cancer Research, Apr. 2002, pp. 2258-2260, vol. 62.
Kutay, H. et al., "Downregulation of miR-122 in the Rodent and Human Hepatocellular Carcinomas," Journal of Cellular Biochemistry, 2006, pp. 671-678, vol. 99.
Lagos-Quintana, et al., Identification of Novel Genes Coding for Small Expressed RNA's, Science, 2001, vol. 294, 5543, pp. 853-858.
Lagos-Quintana, M. et al., "Identification of Tissue-Specific MicroRNAs from Mouse," Current Biology, Apr. 2002, pp. 735-739, vol. 12.
Lagos-Quintana, M. et al., "New MicroRNAs From Mouse to Human," RNA, 2003, pp. 175-179, vol. 9, No. 2.
Lajolo, et al., Effect of fenretinlde on DMBA Induced oral cancer. Histolomorphologlcal study, Diagnosis Radiotherapy, p. 147.
Lall, et al., A Genome-Wide Map of Conserved MicroRNA Targets in C. elegans, Curr Biol 16, 2006, pp. 460-471.
Landgraf, P. et al., "A Mammalian MicroRNA Expression Atlas Based on Small RNA Library Sequencing," Cell, Jun. 2007, pp. 1401-1414, vol. 129.
Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.
Landthaler, et al., The Human DiGeorge Syndrome Critical Region Gene 8 and Its *D. melanogaster* Homolog Are Required for miRNA Biogenesis, CB, 14, 2004, pp. 2162-2167.
Lanza, G. et al., "mRNA/microRNA Gene Expression Profile in Microsatellite Unstable Colorectal Cancer," Molecular Cancer, 2007, pp. 1-11, vol. 6, No. 54.
Lau, et al., An Abundant Class of Tiny RNA's With Probable Regulatory Roles in Caenorhabditis elegans, Science 2001, vol. 294, 5543, pp. 858-862.
Lawrie, C. H. "MicroRNAs and Haematology: Small Molecules, Big Function," British Journal of Haematology, Jun. 2007, pp. 503-512, vol. 137, No. 6.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Lawrie, C.H., "MicroRNA, Expression in Lymphoma," Expert Opinoin on Biological Therapy, Sep. 2007, pp. 1363-1374, vol. 7, No. 9.
Lecellier, et al., A Cellular MicroRNA mediates Antiviral, Science, 2005, vol. 308, pp. 557-560.
Lee, E. J. et al., "Expression Profiling Identifies MicroRNA Signature in Pancreatic Cancer," Int. J. Cancer, 2006, pp. 1046-1054, vol. 120.
Lee, E.J., "Expression and Function of MicroRNA in Human Cancer," Dissertation, The Ohio State University, 2008.
Lee, et al., An Extensive Class of Small RNA's in Caenorhabditis Elegans, Science, 2001, vol. 294, 5543, pp. 862-864.
Lee, et al., MicroRNA maturation: stepwise processing and subcellular localization, EMBO, J., 2004, vol. 40, 3, pp. 667-676.
Lee, et al., MicroRNA maturation: stepwise processing and subcellular localization, EMBO, J. 2002, vol. 21, 17, pp. 4663-4670.
Lee, Y.S. et al., "MicroRNAs: Small but Potent Onogenes or Tumor Suppressors," Current Opinion in Investigational Drugs, Jun. 2006, pp. 560-564, vol. 7, No. 6.
Levy, et al., Staging of hepatocellular carcinoma: assessment of the CLIP, Okuda, and Child-Pugh staging systems in a cohort of 257 patients in Toronto, Gut, 2002, vol. 50, 6, pp. 881-885.
Lewis, B. P. et al., "Prediction of Mammalian MicroRNA Targets," Cell, Dec. 2003, pp. 787-798, vol. 115.
Lewis, et al., Conserved Seed Pairing, Often Flanked by Adenosines, Indicates that Thousands of Human Genes are MicroRNA Targets, Cell, 2005, vol. 120, 1, pp. 15-20.
Li et al., miR-181a Is an Intrinsic Modulator of T Cell Sensitivity and Selection, Cell 2007, pp. 147-161.
Li, et al., DNA mismatch repair (MMR)-dependent 5-fluorouracil cytotoxicity and the potential for new therapeutic targets, British Journal of Pharmacology, 2008, vol. 158, pp. 679-692.
Li, et al., Expression of serum miR-221 in human heptocellular carcinoma and its prognostic significance, Biochemical Biophys Res Commun, 2011, vol. 406, pp. 70-73.
Li, S.-C. et al., "Bioinformatic Discovery of MicroRNA Precursors from Human ESTs and Introns," BMC Genomics, 2006, vol. 7.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Lin, et al., Alteration of DNA methyltransferases contributes to 5 CpG methylation and poor prognosis in lung cancer, LungCancer, vol. 55, 2007, pp. 205-213.
Lin, R.-K. et al., "Alteration of DNA Methyltransferases Contributes to 5'CpG Methylation and Poor Prognosis in Lung Cancer," Lung Cancer, 2007, pp. 205-213, vol. 55.
Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.
Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.

(56) References Cited

OTHER PUBLICATIONS

Liu, et al., Characterization of in vitro and in vivo hypomethylating effects of decitabine in acute myeloid leukemia by a rapid, specific and sensitive LC-MS/MS method, Nucleic Acids, vol. 35, 2007, e31.
Liu, et al., Increased Expression of MicroRNA-221 in Gastric Cancer and Its Clinical Significance, Journal of International Medical Research, 2012, vol. 40, pp. 467-474.
Liu, Tissue inhibitor of metalloproteinase-1 protects human breast epithelial cells from extrinsic cell death: a potential oncogenic activity of tissue inhibitor of metalloproteninase-1, Cancer Research, vol. 65, No. 3, pp. 898-906.
Loffler, D. et al., "Interleukin-6-Dependent Survival of Multiple Myeloma Cells Involves the Stat3-Mediated Induction of MicroRNA-21 Through a Highly Conserved Enhancer," Blood, 2007, pp. 1330-1333, vol. 110, No. 4.
Lu, J. et al., "MicroRNA Expression Profiles Classify Human Cancers," Nature, Jun. 2005, pp. 834-838, vol. 435.
Lujambio, A. et al., "A MicroRNA DNA Methylation Signature for Human Cancer Metastasis," PNAS, Sep. 2008, pp. 13556-13561, vol. 105, No. 36.
Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.
Ma, X., et al., MicroRNAs in NF-kB signaling, Journal of Molecular Cell Biology, 2011, vol. 3, pp. 159-166.
Mack, G. S., "MicroRNA Gets Down to Business," Nature Biotechnology, Jun. 2007, pp. 631-638, vol. 25, No. 6.
Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.
Marcucci, et al., "MicroRNA Expression in Cytogenetically Normal Acute Myeloid Leukemia," NEJM, May 2008, pp. 1919-1928, vol. 358, No. 18.
Marsit, et al., MicroRNA Responses to Cellular Stress, Cancer Research, 2006, vol. 66, pp. 10843-10848.
Martin, M. et al., "MicroRNA-155 Regulates Human Angiotensin II Type 1 Receptor Expression in Fibroblasts," The Journal of Biological Chemistry, Jul. 2006, pp. 18277-18284, vol. 281, No. 27.
Mascellani, N. et al., "Using miRNA Expression Data for the Study of Human Cancer," Minerva Biotec, 2008, pp. 23-30, vol. 20.
Masri, A. et al., "MicroRNA Expression Analysis in Multiple Myeloma," Blood, Nov. 2005, p. 446A, vol. 106, No. 11, Abstract.
Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.
Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," Journal of Biological Chemistry, vol. 282, No. 29, pp. 21337-21348, Jul. 20, 2007.
McManus, M. T., "MicroRNAs and Cancer," Seminars in Cancer Biology, 2003, pp. 253-258, vol. 13.
Medina, et al., MicroRNA's 221 and 222 Bypass Quiescence and Compromise Cell Survival Cancer Research, 2008, vol. 68, pp. 2773-2780.
Medina, P.P. et al., "OncomiR Addiction in an In Vivo Model of MicroRNA-21-Induced Pre-B-Cell Lymphoma," Nature Letters, Sep. 2010, pp. 86-91, vol. 467.
Medina, P.P., "OncomiR Addicton in an in vivo Model of MicroRNA-21-Induced Pre-B-Cell Lymphoma," Supplementary Information, Sep. 2010, p. 1-22.
Megraw, M. et al., "miRGen: A Database for the Study of Animal MicroRNA Genomic Organization and Function," Nucleic Acids Research, 2007, pp. D149-D155, vol. 35.
Mendell, J.T., "miRiad Roles for the miR-17-92 Cluster in Development and Disease," Cell. Apr. 18, 2008; 133(2) :217-222.
Meng, F. et al., "MicroRNA-21 Regulates Expression of the PTEN Tumor Suppressor Gene in Human Hepatocellular Cancer," Gastroenterology, 2007, pp. 647-658, vol. 133.
Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mercatelli, et al., The Inhibition of the Highly Expressed Mir-221 and Mir-222 Impairs the Growth of Prostate Carcinoma Xenografts in Mice, Plos One, 2008, vol. 3, No. 12, pp. 21337-21348.
Metzler, et al., High Expression of Precursor MicroRNA-155/BIC RNA in Children with Burkitt Lymphoma, Genes, Chromosomes, Cancer, 2004, vol. 39, 2, pp. 167-169.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.
Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mishra, A. et al., "Cancer Biomarkers: Are We Ready for the Prime Time?" Cancers, 2010, pp. 190-208, vol. 2.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mizusawa, et al., Differentiation phenotypes of pancreatic islet h- and a-cells are closely related with homeotic genes and a group of differentially expressed genes, Gene 2004, vol. 331, pp. 53, 63.
Mountzios, G. et al., "Mechanisms of Disease: Signal Transduction in Lung Carcinogenesis—A Comparison of Smokers and Never-Smokers," Nature Clinical Practice Oncology, Oct. 2008, pp. 610-618, vol. 5, No. 10.
Mueller, J. et al., "Comprehensive Molecular Analysis of Mismatch Repair Gene Defects in Suspected Lynch Syndrome (Hereditary Nonpoluposis Colorectal Cancer) Cases," Cancer Research, 2009, pp. 7053-7061, vol. 69, No. 17.
Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.
Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.
Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.
Nakamura, et al., ALL-1 Is a Histone Methyltransferase that Assembles a Supercomplex of Proteins Involved in Transcriptional Regulation, Mol. Cell, 10, 2002, pp. 1119-1128.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Nam, E.J. et al., "MicroRNA Expression Profiles in Serous Ovarian Carcinoma," Clinical Cancer Research, 2008, pp. 2690-2695, vol. 14, No. 9.
Nana-Sinkam, et al., Clinical applications for microRNA's in cancer, Nature, 2013, vol. 93.
Nazarov, et al., Interplay of microRNAs, transcription factors and target genes: linking dynamic expression changes to function, Nucleic Acids Research, 2013, vol. 41, No. 5, pp. 2817-2831.
Negrini, M. et al., "MicroRNAs in Human Cancer: From Research to Therapy," Journal of Cell Science, Apr. 2007, pp. 1833-1840, vol. 120.

(56) References Cited

OTHER PUBLICATIONS

Nicoloso, M.S. et al., "MicroRNAs—The Micro Steering Wheel of Tumour Metastases," Nature Reviews: Cancer, Apr. 2009, pp. 293-302, vol. 9.

Nippon—Journal of the Japanese Society, 1993, vol. 82, pp. 1053-1057.

Nurden, A.T., "Qualitative Disorders of Platelets and Megakaryocytes," Journal of Thrombosis and Haemostasis, 2005, vol. 3, pp. 1773-1782.

O'Connell, R. et al., "Inositol Phosphatase SHIP1 is a Primary Target of miR-155," PNAS, Apr. 2009, pp. 7113-7118, vol. 106, No. 17.

O'Donnell, c-Myc-regulated microRNAs modulate E2F1 expression, Nature, 2005, pp. 839-843.

Okada, H. et al., "MicroRNAs in Immune Regulation—Opportunities for Cancer Immunotherapy," The International Journal of Biochemistry & Cell Biology, 2010, pp. 1256-1261, vol. 42.

Okuda, et al., Natural History of Hepatocellular Carcinoma and Prognosis in Relation to Treatment, Cancer, 1985, vol. 56, 4, pp. 918-928.

Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.

Palamarchuk, A. et al., "Akt Phosphorylates Tcl1 Oncoprotein and Inhibits Its Repressor Activity," Cancer Research, Jun. 2005, pp. 4515-4519, vol. 65, No. 11.

Pallante, et al., MicroRNA deregulation in human thyroid papillary carcinomas, Endocr. Relat. Cancer, 2006, vol. 13, 2, pp. 497-508.

Pan, M. R. et al. Non-Steroidal Anti-Inflammatory Drugs Suppress The ERK, Cellular Signaling, 20, 2008, pp. 1134-1141.

Panarelli, et al., MicroRNA Expression Aids the Preoperative Diagnosis of Pancreatic Ductal Adenocarcinoma, Pancreas, 2012, vol. 41, pp. 685-690.

Papageorgiou, et al., Interferon-α Induces TRAIL Expression and Cell Death Via an IRF-1-Dependent Mechanism in Human Bladder Cancer Cells, Cancer Biol Ther, 2007, vol. 6, No. 6, pp. 872-879.

Park, et al., Antisense inhibition of microRNA-21 or-221 arrests cell cycle, induces apoptosis, and sensitizes the effects of gemcitabine in pancreatic adenocarcinoma, Pancreas, 2009, Abstract.

Park, J.-K. et al., "miR-221 Silencing Blocks Hepatocellular Carcinoma and Promotes Survival," Cancer Research, Dec. 2011, pp. 7608-7616, vol. 71, No. 24.

Parkin, et al., Global Cancer Statistics, 2002, CA, Cancer, J. Clin., 2005, vol. 55, 2, pp. 74-108.

Partha, D. et al., "Early Detection of Ovarian Cancer," NIH Public Access Author Manuscript, Jun. 2008, pp. 1-17, Retrieved from the Internet.

Pasquinelli, et al., MicroRNAs: a developing story, Current Opinion in Genetics and Development, vol. 15, 2005, pp. 200-205.

Pathi, S. S., et al., GT-094, a No-NSAID, Inhibits Colon, Molecular Cancer Research, 2011, vol. 9, pp. 195-202.

Pawelczyk, T. et al., "Expression in *Escherichia coli* and Simple Purification of Human Fhit Protein," Protein Expr. Purlf., Apr. 2000, pp. 320-326, vol. 18, No. 3.

Pedersen, I. M. et al., "Interferon Modulation of Cellular MicroRNAs as an Antiviral Mechanism," Nature, Oct. 2007, pp. 919-922, vol. 449.

Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.

Pekarsky, Y. et al., "Animal Models for Chronic Lymphocytic Leumekia," Journal of Cellular Biochemistry, 2007, pp. 1109-1118, vol. 100.

Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.

Pekarsky, Y. et al., "Tcl1 Enhances Akt Kinase Activity and Mediates Its Nuclear Translocation," PNAS, Mar. 2000, pp. 3028-3033, vol. 97, No. 7.

Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.

Petrocca, F. et al., "MicroRNAs Deregulation in Gastric Cancer," PNAS, Apr. 2006, p. 1338, vol. 47, Abstract # 5690.

Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.

Pichiorri, F. et al., "MicroRNAs Regulate Critical Genes Associated with Multiple Myeloma Pathogenesis," PNAS, Sep. 2008, pp. 12885-12890, vol. 105, No. 35.

Pichiorri, F. et al., "MicroRNA Signatures in Multiple Myeloma," 99th AACR Annual Meeting, Apr. 12-16, 2008, pp. 1203, vol. 49, Abstract.

Pineau, P. et al., "miR-221 Overexpression Contributes to Liver Tumorigenesis," PNAS, Jan. 2010, pp. 264-269, vol. 107, No. 1.

Poliseno, et al., MicroRNAs modulate the angiogenic properties of HUVECs, Blood, 2006.

Porkka, K.P. et al., "MicroRNA Expression Profiling in Prostate Cancer," Cancer Research, 2007, pp. 6130-6135, vol. 67, No. 13.

Pouponnot, C. et al., "Cell Context Reveals a Dual Role for Maf in Oncogenesis," Oncogene, 2006, pp. 1299-1310, vol. 25.

Poy, et al., A pancreatic islet-specific microRNA regulates insulin secretion, Nature, 2004, vol. 432, pp. 226-230.

Prueitt, R. L. et al., "Expression of MicroRNAs and Protein-Coding Genes Associated with Perineural Invasion in Prostate Cancer," The Prostate, 2008, pp. 1152-1164, vol. 68.

Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.

Pu, et al., Circulating miR-221 directly amplified from plasma is a potential diagnostic and prognostic marker of colorectal cancer and is correlated with p53 expression, J. Gastroenterol Hepatol, 2010, vol. 25, pp. 1674-1680.

Qin, H. R. et al., "A Role for the WWOX Gene in Prostate Cancer," Cancer Research, Jul. 2006, pp. 6477-6481, vol. 66, No. 13.

Ramkissoon, S. H, et al., "Hematopoietic-Specific MicroRNA Expression in Human Cells," Leukemia Research, 2006, pp. 643-647, vol. 30.

Ren, et al., Co-delivery of as-miR-21 and 5-FU by Poly (amidoamine) Dendrimer Attenuates Human Glioma Cell Growth in Vitro, Journal of Biomedical Science, 2010, vol. 21, pp. 303-314.

Resnick, et al., The detection of differentially expressed microRNAs from the serum of ovarian cancer patients using a novel real-time PCR platform, Science Direct, 2009, vol. 112, pp. 55-59.

Ribas, J. et al., "The Transcriptional Regulation of miR-21, Its Multiple Transcripts, and Their Implication in Prostate Cancer," Cell Cycle, 2010, pp. 923-929, vol. 9.

Rockerfeller, Science Daily, Web address: http://www.sciencedaily.com/release/2009/05/090522171001.htm Nov. 1, 2013.

Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.

Rosa, et al., The miR-430/427/302 Family Controls Mesendodermal Fate Specification via Species-Specific Target Selection, Developmental Cell, 16, 2009, pp. 517-527.

Rossi, et al., Modification of MiR gene expression pattern in human colon cancer cells following exposure to 5-fluorouracil in vitro, Pharmacological Research, Academic Press, Londdon, GB, vol. 56, No. 3, Aug. 30, 2007, pp. 248-253.

Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.

Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.

Ryu, J.K. et al., "Aberrant MicroRNA-155 Expression is an Early Event in the Multistep Progression of Pancreatic Adenocarcinoma," Pancreatology, 2010, pp. 66-73, vol. 10.

Sah., et al, Translation Inhibitors Sensitize Prostate Cancer Cells to Apoptosis Induced by Tumor Necrosis Factor-related Apoptosis-

(56) References Cited

OTHER PUBLICATIONS inducing Ligand (TRAIL) by Activating c-Jun N-terminal Kinase, J. Biol Chem 2003, vol. 278, pp. 20593-20602.
Saini, H. K. et al., "Annotation of Mammalian Primary MicroRNAs," BMC Genomics, 2008, vol. 9.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Salovaara, R. et al., "Population-Based Molecular Detection of Hereditary Nonpolyposis Colorectal Cancer," Journal of Clinical Oncology, Jun. 2000, pp. 2193-2200, vol. 18, No. 11.
Santanam, U. et al., "Chronic Lymphocytic Leukemia Modeled in Mouse by Targeted miR-29 Expression," PNAS, Jul. 2010, pp. 12210-12215, vol. 107, No. 27.
Sarver, A.L. et al., "Human Colon Cancer Profiles Show Differential microRNA Expression Depending on Mismatch Repair Status and are Characteristic of Undifferentiated Proliferative States," BMC Cancer, 2009, pp. 1-15, vol. 9. No. 401.
Sasaki, Y.T.F. et al., "Coordinated Expression of ncRNAs and HOX mRNAs in the Human HOXA Locus," Biochemical and Biophysical Communications, 2007, pp. 724-730, vol. 357.
Schagen, F. et al., "Genetic Targeting of Adenovirus Vectors Using a Reovirus Sigmal-Based Attachment Protein," Molecular Therapy, May 2006, pp. 997-1005, vol. 13, No. 5.
Scher, et al., Fenretinide-inducad apoptosis of human head and neck squamous carcinoma cell lines, vol. 118, Issue 4, pp. 464-471.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.
Schetter, et al., MicroRNA Expression Profiles Associated With Prognosis and Therapeutic Outcome in Colon Adenocarcinoma, Journal of America Medical Association, 2008, vol. 299, pp. 426-436.
Schmittgen, T. D. et al., "A High-Throughput Method to Monitor the Expression of MicroRNA Precursors," Nucleic Acids Research, Feb. 2004, vol. 32, No. 4.
Schrump, et al., Targeting the Epigenome for the Treatment and Prevention of Lung Cancer Semin Oncol, 32, 2005, pp. 488-502.
Scully, Oral Precancer: Preventive and Medical Approaches to Management, Oral Oncol., Eur J. Cancer, 1995, vol. 31B, No. 1, pp. 16-26.
Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.
Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.
Selvendiran, K. et al. NCX-4016 a Nitro-derivative of Aspirin, Cell Cycle, 2008, 7:1, pp. 81-88.
Seth, P., "Vector-Mediated Cancer Gene Therapy," Cancer Biology & Therapy, May 2005, pp. 512-517, vol. 4, Issue 5.
Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.
Sharma, S. et al., "Development of Inhalational Agents for Oncologic Use," Journal of Clinical Oncology, Mar. 2001, Abstract, vol. 19, Issue 6.
Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.
Shih, K.K. et al., "Exosomal MicroRNAs Step into the Biomarker Arena," Gynecologic Oncology, Jul. 2008, pp. 1-2, vol. 110, No. 1.
Skalsky, R.L. et al., "Kaposi's Sarcoma-Associated Herpesvirus Encodes an Ortholog of miR-155," Journal of Virology, Dec. 2007, pp. 12836-12845, vol. 81, No. 23.
Slaby, et al., AlteredExpressionofmiR21-miR31, Oncology, 2007, vol. 72, pp. 1-6.
Slack, F.J., "Big Roles for Small RNAs," Nature, Feb. 2010, p. 616, vol. 463.
Sonoki, T. et al., "Insertion of MicroRNA-125b-1, A Human Homologue of lin-4, into a Rearranged Immunoglobulin Heavy Chain Gene Locus in a Patient with Precursor B-Cell Acute Lymphoblastic Leukemia," Leukemia, 2005, pp. 1-2, vol. 19.
Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.
Stenvang, et al., The utility of LNA in microRNA-based cancer diagnostics and therapeutics, Cancer Biology, 2008, pp. 89-102.
Suarez-Saiz, F.J. et al., "MicroRNA Expression Profiling in Acute Myelogenous Leukemia," Canada Blood, Nov. 2004, Abstract #1131, p. 320A.
Sugito, et al., RNASEN regulates Cell Proliferation and Affects Survival in Esophageal Cancer Patients, Clin Canc Res, 2006[1], vol. 12, pp. 7322-7328.
Suh, et al., Human embryonic stem cells express a unique set of microRNAs, Dev. Biol., 270, 2004, pp. 488-498.
Sun Kai, Analysis of microRNA expression patterns, Chinese Journal of Experimental Surgery, 2006, vol. 23, No. 8, pp. 945-947.
Sun, et al., MicroRNA-221 inhibits CDKN1C/p57 expression in human colorectal carcinoma, Acta Pharmacologica Sinica, 2011, vol. 32, pp. 375-384.
Suzuki, et al., RNA Interference-Mediated Knockdown of DNA Methyltransferase 1 Leads to Promoter Demethylation and Gene Re-Expression in Human Lung and Breast Cancer CellsCancer, Research, 64, 2004, pp. 3137-3143.
Szymanski M., et al., A new frontier for molecular medicine: Noncoding RNAs, BBA, vol. 1756, No. 1, Sep. 25, 2005, pp. 65-75.
Taccioli, C. et al., "Ucbase & miRfunc: A Database of Ultraconserved Sequences and MicroRNA Function," Nucleic Acids Research, 2009, pp. D41-D48, vol. 37.
Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.
Tam, The Emergent Role of MicroRNA's in Molecular Diagnostics of Cancer, Journal of Molecular Diagnostics, 2008, vol. 10, pp. 411-414.
Tang, X. et al., "A Simple Array Platform for MicroRNA Analysis and Its Application in Mouse Tissues," RNA, Aug. 2007, pp. 1-20, vol. 13.
Tanner et al., BAALC, The human member of a novel mammalian neuroectoderm gene lineage, is implicated in hematopoiesis and acute leukemia, PNAS, Nov. 20, 2001, vol. 98, No. 24, pp. 13901-13906.
Tanzer, Molecular Evolution of a MicroRNA Cluster, J. Mol. Biol, 2004, vol. 339, 2, pp. 327-335.
Tatsuya, et al., Oncogenic All1 fusion proteins target Drosha-mediated microRNA processing, PNAS, 2007, vol. 104, pp. 10980-10985.
Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Teachey, et al., Mammalian target of rapamycin inhibitors and their potential role in therapy in leukemia and other haematogical malignancies, BJH, 2009[1], vol. 145, pp. 569-580.
Thomson, et al., Extensive post-transcriptional regulation of microRNAs and its implications for cancer Genes, Dev. 20, 2006, pp. 2202-2207.
Thomson, J. M. et al., "A Custom Microarray Platform for Analysis of MicroRNA Gene Expression," Nature Methods, Oct. 2004, pp. 1-7, vol. 1, No. 1.
Thomson, M., Supplementary data for "A Custon Microarray Platform for Analysis of MicroRNA Gene Expression," Nature Methods, Oct. 2004, pp. 47-53, vol. 1, No. 1.

(56) References Cited

OTHER PUBLICATIONS

Thorgeirsson, et al., Molecular pathogenesis of human hepatocellular carcinoma, Nat, Genet. 2002, vol. 31, 4, pp. 339-346.
Thorgeirsson, S. S. et al., "Functional Genomics of Hepatocellular Carcinoma," Hepatology, Feb. 2006, pp. S145-S150, vol. 43, No. 2, Suppl. 1.
Tibshirani, et al., Diagnosis of multiple cancer types by shrunken centroids of gene expression, Proc. Natl. Acad. Sci., 2002, vol. 99, 10, pp. 6567-6572.
Tili, E. et al., "Expression and Function of Micro RNAs in Immune Cells During Normal or Disease State," International Journal of Medicine Sciences, 2008, pp. 73-79, vol. 5, No. 2.
Tili, E. et al., "Mutator Activity Induced by microRNA-155 (miR-155) Links Inflammation and Cancer," PNAS, Mar. 2011, pp. 4908-4913, vol. 108, No. 12.
Tkachuk, et al., Involvement of a Homolog of Drosophila trithorax by 11 q23 Chromosomal Translocations in Acute Leukemias Cell, vol. 71, 1992, pp. 691-700.
Tockman, M. S. et al., "Considerations in Bringing a Cancer Biomarker to Clinical Application," Cancer Research, May 1992, pp. 2711s-2718s, vol. 52.
Tokarz, et al., The Role of microRNA in metastatic colorectal cancer and its significance in cancer prognosis and treatment, ACTA, 2012, vol. 59, pp. 467-474.
Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.
Tricoli, J. V. et al., "MicroRNA: Potential for Cancer Detection, Diagnosis, and Prognosis," Cancer Research, May 2007, pp. 4553-4555, vol. 67, No. 10.
Tsunoda, et al., Oncogenic KRAS regulates miR-200c and miR-221, 222 in a 3D-specific manner in colorectal cancer cells, Anticancer Research, 2011, Abstract.
Tusher, et al., Significance analysis of microarrays applied to the ionizing radiation response, Proc. Natl. Acad. Sci., 2001, vol. 98, 9, pp. 5116-5121.
Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.
Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.
Ulivi, et al., p16INK4A and CDH13 Hypermethylation in Tumor and Serum of Non-Small Cell Lung Cancer Patients Journal of Cell, Physiol, 206, 2006, pp. 611-615.
Valeri, et al., MicroRNA-21 induces resistance to 5-fluorouracil by down-regulating human DNA MutS homolog 2 hMSH2 ,PNAS, 2010, vol. 107, pp. 21098-21103.
Valeri, N. et al., "Pathogenetic and Clinical Relevance of microRNAs in Colorectal Cancer," Cancer Genomics Proteomics, Jul./Aug. 2009, pp. 195-204, vol. 6, No. 4.
Valeri, N. et al., "Epigenetics, miRNAs, and Human Cancer: A New Chapter in Human Gene Regulation," Mamm Genome, Aug. 2009, pp. 573-580, vol. 20.
Valeri, N. et al., "Modulation of Mismatch Repair and Genomic Stability by miR-155," PNAS, Apr. 2010, pp. 6982-6987, vol. 107, No. 15.
Vandeneynde, et al., Is Tailored Adjuvant Treatment for Colon Cancer Possible, Clinical Colorectal Cancer, 2010, vol. 9, pp. 15-21.
Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.
Varotti, et al., Comparison between the fifth and sixth editions of the AJCC/UICC TNM staging systems for hepatocellular carcinoma: multicentric study on 393 cirrhotic resected patients, Eur. J. Surg. Oncol, 2005, vol. 31, 7, pp. 760-767.
Vassilev et al., "In Vivo Activation of the p53 Pathway by Small-Molecule Antagonists of MDM2," Science, 2004, pp. 844-848, vol. 303.
Vatolin, et al., A Novel Method to Detect Functional MicroRNA Targets, J. Mol. Biol., 358, 2006, pp. 983-996.
Verschuur, A.C., "Acute Megakaryoblastic Leukemia," May 2004, pp. 1-5, Retrieved from the Internet: URL: http://www.orpga.net/data/patho/GB/uk-AMLM7.pdf.
Virgilio, L. et al., "Identification of the TCL1 Gene Involved in T-Call Malignancies," Proc. Natl. Acad. Sci., Dec. 1994, pp. 12530-12534, vol. 91.
Visone, R. et al., "MiRNAs and Cancer," The American Journal of Pathology, Apr. 2009, pp. 1131-1138, vol. 174, No. 4.
Volinia, et al., "Reprogramming of MirRNA Networks in Cancer and Leukemia," Genome Research, 2010, pp. 589-599, vol. 20.
Volinia, et al., Breast cancer signatures for invasiveness and prognosis defined by deep sequencing of microRNA, PNAS, Feb. 21, 2012, vol. 109, No., pp. 3024-3029.
Volinia, Prognostic microRNA/mRNA signature from the integrated analysis of patients with invasive breast cancer, PNAS, pp. 1-5.
Volinia, S. et al., "A MicroRNA Expression Signature of Human Solid Tumors Defines Cancer Gene Targets," PNAS, Feb. 2006, pp. 2257-2261, vol. 103, No. 7.
Wang, E. et al., "Ontogeny and Oncogenesis Balance the Transcriptional Profile of Renal Cell Cancer," Cancer Research, Oct. 2004, pp. 7279-7287, vol. 64.
Wang, X. et al., "Association Between CpG Island Methylation of the WWOX Gene and Its Expression in Breast Cancers," Tumor Biology, Feb. 2009, pp. 8-14, vol. 30.
Watson, D.I. et al., "MicroRNA Expression Profiles in Barrett's Oesophagus," RACS Annual Scientific Congress, 2007, pp. A45, vol. 77.
Weidhaas, J., "Using MicroRNAs to Understand Cancer Biology," Published Online Dec. 21, 2009, DOI: 10.1016/S1470-2045(09)70386-9.
Wiemer et al., "The Role of MicroRNAs in Cancer: No Small Matter," European Journal of Cancer, Jun. 12, 2007, vol. 43, No. 10, pp. 1529-1544.
Wijermans, P.W., "Low Dose Azanucleosidesfor High Risk (s) MDS and AML," Haematologica Reports,Nov. 2006, pp. 74-76. vol. 2, Issue, 15.
Wildi, et al., Critical evaluation of the different staging systems for hepatocellular carcinoma, Br. J. Surg., 2004, vol. 91, 4, pp. 400-408.
Wu, D. et al., "Micro-RNA: A New Kind of Gene Regulators," Agricultural Sciences in China, Jan. 2006, pp. 77-80, vol. 5, No. 1.
Wu, et al., Mucoadhesive Fenretinide Patches for Site-Specific Chemoprevention of Oral Cancer: Enhancement of Oral Mucosal Permeation of Fenretinide by Coincorporation of Propylene Glycol and Menthol, Molecular Pharmaceutics, 2012, No. 9, pp. 937-945.
Xi, Y. et al., "Prognostic Values of MicroRNAs in Colorectal Cancer," Biomarker Insights, Jan. 2006, pp. 113-121, vol. 1.
Y. Yu, et al., Context-Dependent Bidirectional Regulation of the MutS Homolog 2 by Transforming Growth Factor Contributes to Chemoresistance in Breast Cancer Cells, Molecular Cancer Research, vol. 8, No. 12, Oct. 14, 2010, pp. 1633-1642.
Yamamichi, et al., Locked Nucleic Acid In Situ Hybridization Analysis of MiR-21 Expression during Colorectal Cancer Development, Clinical Cancer Research, vol. 15, No. 12, Jun. 15, 2009, pp. 4009-4016.
Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.
Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.
Yanaihara, N. et al., "Unique MicroRNA Molecular Profiles in Lung Cancer Diagnosis and Prognosis," Cancer Cell, Mar. 2006, pp. 189-198, vol. 9.
Yang, J. et al., "Analysis of Sequence Variations in 59 MicroRNAs in Hepatocellular Carcinomas," Mutation Research, Aug. 2008, pp. 205-209, vol. 638.

(56) References Cited

OTHER PUBLICATIONS

Ye, et al., Predicting hepatitis B virus-positive metastatic hepatocellular carcinomas using gene expression profiling and supervised machine learning, Nat. Med., 2003, vol. 9, 4, pp. 416-423.
Yekta, et al., MicroRNA-Directed Cleavage of HOXB8 MRNA, Science, 2004, vol. 304, pp. 594-596.
Yendamuri, S. et al., "WW Domain Containing Oxidoreductase Gene Expression is Altered in Non-Small Cell Lung Cancer," Cancer Research, Feb. 2003, pp. 878-881, vol. 63.
Yi, et al., Exportin-5 mediates the nuclear export of pre-microRNAs and short hairpin RNAs, Genes Dev, 2003, vol. 17, 24, pp. 3011-3016.
Yoo, et al., Epigenetic therapy of cancer: past, present and future, Nature Reviews Drug Discov 5, 2006, pp. 37-50.
Yoon, S. et al., "Prediction of Regulatory Modules Comprising MicroRNAs and Target Genes," Bioinformatics Genes and Genomes, 2005. pp. ii93-ii100, vol. 21, Suppl. 2.
Yu, et al., Human microRNA clusters: Genomic organization and expression profile in leukemia cell lines, Biomed Biophys Res Comm, 2006, pp. 59-68.
Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.
Yuki, et al., Growth and Spread of Hepatocellular Carcinoma, Cancer, 1990, vol. 66, 10, pp. 2174-2179.
Zaman, et al., Current status and implications of microRNAs in ovarian cancer diagnosis and therapy, J Ovarian Res, 2012[1].
Zawacka-Pankau, J. et al., "Expression and Simple, One-Step Purification of Fragile Histidine Triad (Fhit) Tumor Suppressor Mutant Forms in *Escherichia coli* and their Interaction with Protoporphyrin IX," Biotechnology Letters, Jun. 2007, pp. 877-883, vol. 29, No. 6.
Zeng, Y. et al., "Recognition and Cleavage of Primary MicroRNA Precursors by the Nuclear Processing Enzyme Drosha," The EMBO Journal, 2005, pp. 138-148, vol. 24.
Zhang, et al., Inhibitory effect of knocking down microRNA-221 and microRNA-222 on glioma cell growth in vitro and in vivo, Chinese Journal of Oncology, 2009, vol. 31, No. 10.
Zhang, In Vitro Study on effect of up-regulation of PETN expression by miR-221 and miR-222 knocked-down in lung cancer cell line A549 cells on radiosensitization, Proceedings of the 5th Chinese Academic Conf. on Tumors, the 7th Academic Conf. on Tumors Across the Taiwan Straits, Academic Conf. on Int'l Tumor Cells and Gene Therapy, and the 2nd Chinese and Japanese Academic Conf. on Tumor Interventional Therapy, p. 317.
Zhang, In vitro study on effect of up-regulation of TIMP3 expression by antisense miR-221 and miR-222 on inhibition of invasiveness of glioblastoma cell U251, The 8th Conference and Symposium Proceedings, China Genetic Association, 2004-2008, p. 139.
Zhang, L. et al., "Genomic and Epigenetic Alterations Deregulate MicroRNA Expression in Human Epithelial Ovarian Cancer," PNAS, May 2008, pp. 7004-7009, vol. 105, No. 19.
Zhang, L. et al., "MicroRNAs Exhibit High Frequency Genomic Alterations in Human Cancer," PNAS, Jun. 2006, pp. 9136-9141, vol. 103, No. 24.
Zhang, L. et al., Supporting Information, PNAS 2008, pp. 1-11.
Zhang, Z. et al., "Three Biomarkers Identified from Serum Proteomic Analysis for the Detection of Early Stage Ovarian Cancer," Cancer Research, Aug. 2004, pp. 5882-5890, vol. 64.
Zhao et al., "p53 Mediates the Negative Regulation of MDM2 by Orphan Receptor TR3," The EMBO Journal, 2006, pp. 5703-5715, vol. 25.
Zhou, et al., Binding of NF-kappaB p65 subunit to the promoter elements is involved in LPS-induced transactivation of miRNA genes in human biliary epithelial cells, Nucleic Acids Research, 2010, vol. 38, No. 10, pp. 3222-3232 [1].
Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.
Chiesa, Fenretinide (4-HPR) in Chemoprevention of Oral Leukoplakia, Journal of Cellular Biochemistry, Supplement, 17F, 1993, pp. 255-261.
Chiesa, Prevention of Local Relapses and New Localisations of Oral Leukoplakias with the Synthetic Retinoid Fenretinide (4-HPR). Preliminary Results, 1992, Oral Oncol. Eur. J. Cancer, vol. 28B, No. 2, pp. 97-102.
Chiesa, Randomized trial of fenretinide (4-HPR) to prevent recurrences, new localizations and carcinomas in patients operated on for oral leukoplakia: Long-term results, Int. J. Cancer, 2005, No. 115, pp. 625-629.
Chinese Office Action, Application No. 201180062951.6, dated Jul. 1, 2014.
PCT International Preliminary Report on Patentability, Application No. PCT/US2011/060838, filed Nov. 15, 2011, dated May 30, 2013.
European Patent Office Extended Search Report for Application No. 11842396.1 dated Oct. 7, 2014 (5 pages).
Japanese Patent Office Action for Application No. 2013-539955 dated Sep. 4, 2015 (5 pages, English translation Only).
Australian Patent Office Examination Report No. 1 dated Feb. 19, 2016 (3 pages).
Desai et al. "Formulation and In Vitro-In Vivo Evaluation of Black Raspberry Extract-Loaded PLGA/PLA Injectable Millicylindrical Implants for Sustained Delivery of Chemopreventive Anthocyanins," Pharmaceutical Research, 2010, vol. 27, No. 4, pp. 628-643.
Andriani, "Increased Sensitivity to Cisplatin-Neoplasia," 2006, vol. 8, No. 1, pp. 9-7.
Lajolo et al., "Effect of fenrentinide on DMBA Induced oral cancer. Histolomorphological study. Diagnosis Radiotherapy," Oral Oncology Supplement, 2005, vol. 1, Issue 1, p. 191.
Liu et al., "Research progress in penetration enhancers," Chinese Journal of Clinical Pharmacy, 2003, vol. 12, No. 4, pp. 257-260.
Scher et al., "Fenretinide-inducad apoptosis of human head and neck squamous carcinoma cell lines," 1998, vol. 118, Issue 4, Abstract.
Yu et al., Effect of combination of menthol, azone and propylene glycol on penetration rate of Qumei slimming patch, Heilongjiang Medicine Journal, 2008, vol. 21, No 4, pp. 88-89.
Extended European Search Report for Application No. 12154300.3 dated Dec. 7, 2012 (13 pages).
Japanese Patent Office Action for Application No. 2013-539955 dated Jul. 4, 2016 (7 pages).
European Patent Office Action for Application No. 11842396.1 dated Apr. 13, 2016 (4 pages).
Australian Examination Report No. 2 for Application No. 2011329066 dated Feb. 9, 2017 (4 pages).
European Patent Office Action for Application No. 11842396.1 dated Aug. 2, 2017 (5 pages).
Japanese Patent Office Action for Application No. 2016-215838 dated Aug. 29, 2017 (9 pages).
Intellectual Property of India Office Action for Application No. 4492/CHENP/2013 dated Mar. 8, 2018 (6 pages).
Australian Patent Office Examination Report No. 1 for Application No. 2017201105 dated Mar. 14, 2018 (5 pages).

* cited by examiner

Fenretinide (MW = 391.6 Da)

Propylene glycol (MW = 76.10 Da)

L-Menthol (MW = 156.27 Da)

Oleic acid (MW = 282.46 Da)

CONTROLLED RELEASE MUCOADHESIVE SYSTEMS

CROSS-REFERENCE TO RELATED APPLICATIONS

This application claims the benefit of the PCT/US2011/060838 filed Nov. 15, 201, which claims priority to U.S. Provisional Application No. 61/413,982 filed Nov. 15, 2010, the entire disclosures of which are expressly incorporated herein by reference.

STATEMENT REGARDING FEDERALLY SPONSORED RESEARCH

This invention was not made with any Government support and the Government has no rights in this invention.

TECHNICAL FIELD AND INDUSTRIAL APPLICABILITY OF THE INVENTION

This invention is directed to formulations for chemoprevention of oral cancer and precancerous lesions, and for methods for preparing the formulations.

Specifically, the invention relates to bioadhesive gels containing a hydrophobic formulation (such as fenretinide), formulated for local delivery for the chemoprevention of oral cancer and precancerous lesions. The invention relates also to methods for stabilizing and enhancing the efficacy of chemopreventive components of the formulations.

BACKGROUND OF THE INVENTION

Head and neck squamous cell carcinoma (HNSCC), which is a world-wide health problem, will affect approximately 36,000 Americans with over 7,000 deaths this year. Despite extensive research and introduction of therapeutic advances such as radiation-intensification, prognosis for persons with HNSCC remains among the lowest of all solid tumors.

Intervention with effective chemopreventive agents—to prevent progression or induce regression—at the pre-cancerous stage would greatly improve clinical outcomes. Analogous to other surface origin malignancies, initiated head and neck epithelium undergoes progressive growth disturbances (grades of epithelial dysplasia) prior to conversion to overt carcinoma. Furthermore, many of these dysplastic lesions arise in visible mucosa, making topical application and direct clinical monitoring of lesion progression feasible. Despite obtaining complete surgical excision, many of these dysplastic lesions recur; necessitating sequential surgeries and increasing patient anxieties regarding cancer development.

The buccal mucosa is an attractive site for the localized delivery of therapeutic agents to treat or prevent oral cancer by using a mucoadhesive patch. However, the benefits of this administration route may be limited due to the barrier properties of the buccal mucosa. Since the buccal mucosa is a tissue that is exposed to many foreign agents, the buccal mucosa significant barrier properties may hinder the transport of therapeutically active compounds.

For example, small lipophilic drug molecules with a log P of 1.6-3.3 are generally believed to permeate well because of greater partitioning into the tissue. However, for highly lipophilic drugs with a log P greater than 3.5, a decrease in permeability is observed due to their limited water solubility. In fact, most agents that are better known for enhancing drug permeability through the skin also improve the transport of compounds across the buccal mucosa.

To increase the permeation of drugs, chemical approaches such as the utilization of chemical permeation enhancers (e.g., surfactants, bile salts, and fatty acids) might be only applicable to patch preparations. There is still a need, however, for formulations that can readily cross the buccal mucosa barriers.

SUMMARY OF THE INVENTION

In a first broad aspect, there is provided herein a formulation, comprising: at least one mucoadhesive material; at least one retinide composition or a pharmaceutically acceptable salt thereof; and, at least one transmucosal permeation enhancer agent selected for enhancing permeation of the retinide composition across a mucosa; and; optionally, at least one solubilizer agent for enhancing release of the retinide composition from the mucoadhesive material.

In another broad aspect, there is provided herein a formulation, comprising: at least one mucoadhesive material; at least one retinide therapeutic agent; and, at least one transmucosal permeation enhancer agent selected from one or more of: propylene glycol (PG) and a terpene or terpenoid composition; and; optionally, at least one solubilizer agent In another broad aspect, there is provided herein a formulation, comprising: at least an effective amount of a pharmaceutically active fenretinide composition, and at least one transmucosal permeation enhancer agent selected from propylene glycol (PG) and menthol.

In another broad aspect, there is provided herein a formulation, comprising: at least an effective amount of a pharmaceutically active fenretinide composition, and transmucosal permeation enhancer agents comprising propylene glycol (PG) and menthol.

In certain embodiments, the formulation comprises from about 1 wt % to about 2.5 wt % PG, and from 1 wt % to about 5 wt % menthol.

In certain embodiments, the formulation comprises from about 1 wt % to about 2.5 wt % PG, and about 5 wt % menthol.

In certain embodiments, the formulation comprises about 1 wt % PG and about 5 wt % menthol.

In certain embodiments, the formulation comprises about 2.5 wt % PG and about 5 wt % menthol.

In certain embodiments, the pharmaceutically active fenretinide composition and the at least one permeation enhancer agent are adapted to be in contact with at least on common mucosal membrane.

In certain embodiments, the mucosal membrane is the buccal mucosa.

In another broad aspect, there is provided herein a transmucosal system comprising at least drug release layer comprised of the formulation generally described herein, at least one bioadhesive material, and at least one backing material.

In another broad aspect, there is provided herein a method, comprising: i) providing a transmucosal system comprising the formulation generally described herein; applying the transmucosal system to a mucosal membrane of a subject; and, keeping the transmucosal system in contact with the mucosal membrane for a therapeutically effective period of time; and, optionally removing the transmucosal system when a desired therapeutic effect has been achieved.

In certain embodiments, the transmucosal system includes a bioadhesive material.

In certain embodiments, the formulation and the bioadhesive material are present in separate compartments.

In another broad aspect, there is provided herein a method of treatment and prophylaxis of a disease, comprising: administering to a subject in need of such treatment the formulation generally described herein.

In another broad aspect, there is provided herein a formulation for application to the oral mucosa, comprising: at least an effective amount of a pharmaceutically active fenretinide composition, and at least one transmucosal permeation enhancer agent selected from propylene glycol (PG) and menthol.

In another broad aspect, there is provided herein a method for treating or preventing head and neck squamous cell carcinoma (HNSCC), comprising administering to a subject an effective amount of a formulation generally described herein.

In another broad aspect, there is provided herein a drug dosage form for oral transmucosal administration, comprising the formulation generally described herein. In certain embodiments, the drug dosage form further includes a bioadhesive material, the bioadhesive material providing for adherence to the oral mucosal membrane of a subject. In certain embodiments, the oral mucosal membrane is a buccal membrane.

In another broad aspect, there is provided herein a drug dosage form for oral transmucosal administration, comprising a formulation comprised of: at least an effective amount of a pharmaceutically active fenretinide composition, and at least one transmucosal permeation enhancer agent selected from propylene glycol (PG) and menthol; and, a bioadhesive material, the bioadhesive material providing for adherence to the oral mucosal membrane.

In certain embodiments, the formulation contains a predetermined amount of pharmaceutically active fenretinide composition in an amount selected from the group consisting of 10 μg, 15 μg, 25 μg, 50 μg, 100 μg, 500 μg, 1 mg, 2 mg, 3 mg, 4 mg, 5 mg, 6 mg, 7 mg, 8 mg, 9 mg and 10 mg and a bioadhesive material, the bioadhesive material providing for adherence to the oral mucosal membrane of a subject.

In certain embodiments, he amount of the pharmaceutically active fenretinide absorbed via the oral mucosa is selected from the group consisting of at least 35%, at least 40%, at least 45%, at least 50%, at least 55%, at least 60%, at least 65%, at least 70%, at least 75%, at least 80%, at least 85%, at least 90%, at least 95%, at least 98% and at least 99% of the drug in the dosage form.

In certain embodiments, a single or repeated oral transmucosal administration to a subject results in a bioavailability of greater than 70%, greater than 75%, greater than 80%, greater than 85%, greater than 90%, or greater than 94%.

In certain embodiments, a single or repeated oral transmucosal administration to a subject results in a bioavailability with a coefficient of variation of less than 30%, or less than 40%.

In certain embodiments, a single oral transmucosal administration of the drug dosage form to a subject results in a $T_{max}$ of from about 6 hours to about 12 hours.

In certain embodiments, a single oral transmucosal administration of the drug dosage form to a subject results in a $T_{max}$ of from about 6 hours to about 8 hours.

In another broad aspect, there is provided herein a method of treating a subject exhibiting a symptomatic medical condition, comprising, administering the formulation generally described herein in a pharmaceutically active amount of a drug effective to reduce or eliminate the symptoms in the subject. In certain embodiments, the symptomatic medical condition is an oral cancer or pre-cancerous condition.

In another broad aspect, there is provided herein a method of a treating an oral cancer or a precancerous condition in a subject comprising, administering the formulation generally described herein.

In another broad aspect, there is provided herein a method for making the formulation generally described herein, comprising: i) mixing a quantity of at least one solubilizer and at least one permeation enhancer in a solvent to form a solvent mixture; ii) adding a quantity of fenretinide to the solvent mixture of step i); and, optionally adjusting a volume thereof to 10 mL with the solvent mixture of step i); iii) forming a layer of the fenretinide mixture of step ii); and, iv) drying the layer of step iii).

In certain embodiments, the solubilizer comprises one or more of: polysorbate 80 (brand names include Alkest®, Canarcel® and Tween® 80 (a registered trademark of ICI Americas, Inc)) which is a nonionic surfactant and emulsifier derived from polyethoxylated sorbitan and oleic acid, and sodium deoxycholate.

In certain embodiments, the permeation enhancer comprises propylene glycol and menthol.

In another broad aspect, there is provided herein a method for chemoprevention of an oral cancer or precancerous condition, comprising topically administering to a subject in need of such chemoprevention the formulation generally described herein.

In certain embodiments, the formulation is administered to an interior of an oral cavity of the subject.

In still further aspects, there is described herein is a mucoadhesive system useful for intraoral administration and slow release of a highly hydrophobic formulation, comprising a co-solvent system that enhances oral mucosal permeation of a hydrophobic formulation.

In certain embodiments, the formulation comprises a highly hydrophobic chemopreventive agent. In certain embodiments, the formulation comprises a retinide composition, such as fenretinide.

Described herein is a method for enhancing oral mucosal permeation of a hydrophobic formulation, comprising co-incorporation of a co-solvent in a hydrogel-based controlled release system.

In certain embodiments, the method includes forming a drug layer comprising fenretinide, mucoadhesive material Eudragit® RL PO films containing mixed nonionic surfactants and deoxycholate solubilizers. In certain embodiments, the drug layer comprises one or more of: nonionic surfactants, bile salts, phospholipids, and polymeric solubilizers.

Described herein is a formulation for chemoprevention of an oral cancer or precancerous condition, comprising a hydrogel-based controlled release mucoadhesive system.

In certain embodiments, the formulation comprises at least one therapeutic agent in an amount effective for chemoprevention.

In certain embodiments, the adhesive carrier is a mucoadhesive gel adapted for transmucosal delivery of fenretinide.

Described herein is a method for chemoprevention of an oral cancer or precancerous condition, comprising topically administering to a subject in need of such chemoprevention a solublized fenretinide preparation admixed with a permeation enhancer agent.

In certain embodiments, the fenretinide preparation admixed with the permeation enhancer agent is administered to an interior of an oral cavity of the subject.

In certain embodiments, the permeation enhancers comprise a mixture of propylene glycol, L-menthol and oleic acid.

Described herein is a method for increasing the concentration of a hydrophobic therapeutic agent in a bodily tissue or fluid of a subject at risk of an oral cancer or precancerous condition, comprising applying a preparation containing the therapeutic agent to an interior of an oral cavity of the subject.

In certain embodiments, the bodily tissue or fluid is selected from the group consisting of a mucosal tissue, an oral mucosa tissue, oral tissue, peripheral blood, serum, and saliva.

Described herein is a method for preparing a formulation for chemoprevention of an oral cancer or precancerous condition.

Described herein is a method for improving the efficacy of a formulation for chemoprevention of an oral cancer or precancerous condition, comprising: providing a fenretinide preparation; admixing the fenretinide preparation with a permeation enhancer formulation to form a mixture; prior to applying the mixture to an oral cavity of a subject in need of chemoprevention.

Described herein is a method for making a buccal drug delivery system, comprising: preparing a drug-release layer comprised of the formulation; preparing an adhesive layer; and, assembling the drug layer and the adhesive layers onto a backing layer.

Described herein is a formulation comprising a solubilizer agent for enhancing release of fenretinide from the patch; and, a permeation enhancer agent for improving permeation of fenretinide across a mucosa.

Described herein is a method for increasing release of a retinide composition from a drug-release layer, comprising: admixing a retinide composition with a solubilizer, and forming the admixture into a drug-release layer.

Described herein is a method for increasing permeation of a retinide composition from into a mucosa of a subject in need thereof, comprising: admixing a retinide composition with a permeation enhancer agent comprised of one or more of propylene glycol and menthol, and forming the admixture into a drug-release layer.

Described herein is a method for increasing release of a retinide composition from a drug-release layer and for increasing permeation of the retinide composition into a mucosa of a subject in need thereof, comprising: admixing a retinide composition with a solubilizer and a permeation enhancer agent, and forming the admixture into a drug-release layer.

Described herein is a method of treatment and prophylaxis of a disease comprising administering to a subject in need of such treatment the formulation.

Described herein is a method for increasing the concentration of a retinide composition in a bodily tissue or fluid of a subject at risk of an oral cancer or precancerous condition, comprising applying the formulation to an interior of an oral cavity of the subject. In certain embodiments, the bodily tissue or fluid is selected from the a mucosal tissue, an oral mucosa tissue and oral tissue Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The patent or application file contains one or more drawings executed in color and/or one or more photographs. Copies of this patent or patent application publication with color drawing(s) and/or photograph(s) will be provided by the Patent Office upon request and payment of the necessary fee.

DETAILED DESCRIPTION OF THE PREFERRED EMBODIMENT

Figures 1A, 1B:
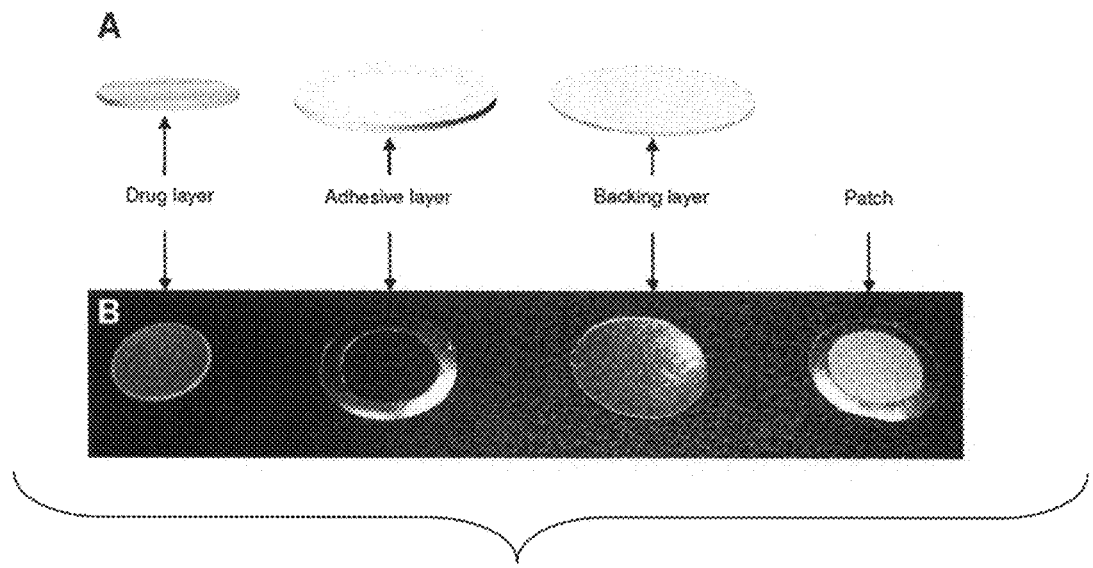
FIGS. 1A-C: Schematic diagrams (FIG. 1A), photographic image (FIG. 1B), and schematic cross-sectional diagram (FIG. 1C) of a mucoadhesive patch comprising drug (fenretinide-mucoadhesive material (Eudragit® RL PO) with or w/o solubilizer), adhesive (hydroxypropyl methylcellulose (HPMC) 4KM:polycarbophil (3:1), and backing (Tegaderm™ dressing) layers.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

In describing and claiming the present invention, the following terminology will be used in accordance with the definitions set out below.

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition (e.g., cancer). The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human. In some embodiments, the pharmacokinetic profiles of the systems of the present invention are similar for male and female subjects.

As used herein, the term "controlled drug delivery" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

As used herein, the term "sustained drug delivery" refers to release or administration of a therapeutic agent from a source (e.g., a drug formulation) in a sustained fashion over a protracted yet specific period of time, which may extend from several minutes to a few hours, days, weeks or months. In certain embodiments, the term "sustained" can refer to delivery of consistent levels of the therapeutic agent over a time period ranging from a few minutes to a day, with a profile characterized by the absence of an immediate release phase, such as the one obtained from intravenous administration.

The present invention is based, at least in part, on the discovery that transmucosal uptake of fenretinide can be enhanced by employing permeation enhancing agents. Such permeation enhancing agents are advantageous, e.g., because the absolute bioavailability of the therapeutic agent contained therein is enhanced, while also providing a desired delivery time period for the therapeutic agent. Additionally, less therapeutic agent is needed in the system to deliver a therapeutic effect versus systems of the prior art.

In particular, there has been a major challenge in developing an effective mucoadhesive system is to achieve continuous and complete drug-release from the system.

In one aspect, described herein is a mucoadhesive system which now provides a continuous and near complete drug-release. The mucoadhesive system, as now described herein provides an improved technology where systemic administration using the mucoadhesive system provides therapeutic levels to the mouth without inducing significant side effects.

The mucoadhesive system-based approach provides a targeted delivery of therapeutic levels of fenretinide at a treatment site without induction of deleterious systemic effects.

The mucoadhesive system described herein overcomes the issues associated with the efficacy of delivery systems for various hydrophobic drugs.

The term "transmucosal," as used herein, refers to any route of administration via a mucosal membrane. Examples include, but are not limited to, buccal, sublingual, nasal, vaginal, and rectal. In one embodiment, the administration is buccal. In one embodiment, the administration is sublingual. As used herein, the term "direct transmucosal" refers to mucosal administration via the oral mucosa, e.g. buccal and/or sublingual.

The term "buccal patch" or "film" typically refers to a flexible film that adheres to the oral mucosa and delivers the therapeutic agent. Such films can be either quick dissolving or dispersing films releasing the therapeutic agent immediately or can be films having mucoadhesive properties with the therapeutic being released over a period of time. These patches or films are typically prepared by mixing the ingredients, heating, extruding, drying and then sizing the sheets to deliver the exact amounts of medications.

The present invention provides a formulation for transmucosal administration that is easy to manufacture, exhibits good stability and allows for flexibility of formulation.

The present invention provides a formulation for transmucosal administration that allows for precise control over the dose administered and the effect obtained.

The present invention provides a formulation for transmucosal administration that is simple, convenient to administer, easy to handle and promotes high patient acceptance and compliance.

In one embodiment, the mucoadhesive system comprises the use of effective solubilizers that enhances the release of the therapeutic agent from the patch.

Figure 1C:
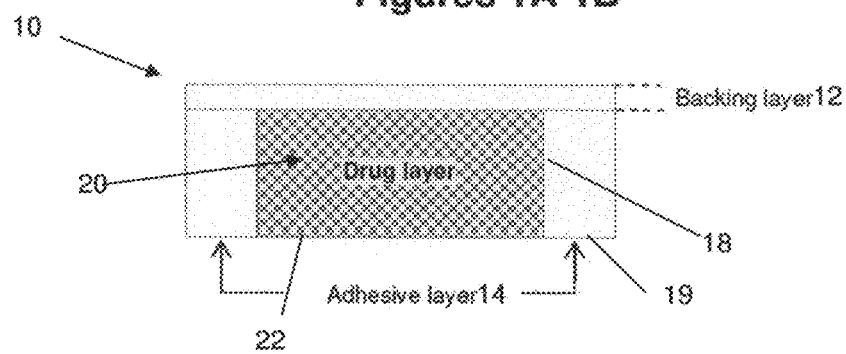

In one embodiment, the solubilizer and the permeation enhancer are co-incorporated with the therapeutic agent in a drug layer film, as schematically illustrated in FIGS. 1A-1C, and as further described below. The solubilizer enhances the release of the therapeutic agent from the drug film layer, while the permeation enhancer improves the permeation of the therapeutic agent across the mucosa. It is to be noted, however, in another embodiment, the formulation be a "single" formulation comprised of the solubilizer and the therapeutic agent.

In another broad aspect, there is provided herein a controlled release retinide mucoadhesive system.

In another broad aspect, there is provided herein formulations of mucoadhesive system for effective controlled release of a therapeutic composition.

The present invention also provides for a method for transmucosal administration of a therapeutic agent where a transmucosal patch is applied to a mucosal membrane and kept in contact with it for a therapeutically effective period of time. When the desired therapeutic effect has been achieved, the patch can be optionally removed.

In one embodiment, the formulation can be delivered by the various transmucosal routes. In a particular embodiment, the formulation is delivered via the buccal mucosa. The buccal mucosa is readily accessible and provides a desired wide area of smooth muscle for application of a patch. In addition, absorption through the buccal mucosa delivers the therapeutic agent directly into the systemic circulation through the internal jugular vein, thus bypassing the hepatic metabolic system. Also, the buccal mucosa tends to have low enzymatic activity, and delivery of the therapeutic agent through the buccal mucosa thus avoids degradation in the gastric and intestinal fluids.

In certain embodiments, the formulation is suitable for both immediate delivery and time-controlled delivery of the therapeutic agent though the buccal mucosa.

Design of Controlled Release Mucoadhesive System

In the embodiment illustrated in FIGS. 1A-1C, a "patch" or mucoadhesive delivery system 10 generally includes a backing layer 12, an adhesive layer 14, and drug-release layer 20. As disclosed herein, the terms "delivery system" and "patch" can be used interchangeably. The patch 10 is designed to be applied to a mucosal membrane, and is used to deliver a therapeutic agent through transmucosal administration. The delivery patch 10 can be of any shape and size as desired.

Each mucoadhesive layer of the system perform specific role and contribute towards effective controlled delivery of one or more therapeutic agents (i.e., drugs). The backing layer 12 (which is insoluble in saliva, water, and the like) prevents the drug loss/release from a rear surface of the drug-release layer 20, thereby providing unidirectional drug-release. The adhesive layer 14 provides strong mucoadhesion with mucosal surfaces. The drug-release layer 20 can provide a substantially continuous and complete drug delivery.

In one embodiment, as described in the Examples herein, the backing layer 12 can be comprised of a Tegaderm® dressing film; the adhesive layer 14 can be comprised of one or more mucoadhesive polymers; and, the drug-release layer 20 can be comprised of a formulation comprised of a therapeutic agent, a for example, a Eudragit® polymer+drug solubilizer).

Referring to FIG. 1C, there is shown a schematic cross-sectional view of patch 10. The adhesive layer 12 can have any suitable general overall configuration. As shown in FIG. 1C, the adhesive layer 12 can define a recess 18. It is to be understood that the depth of the recess can be readily determined by those skilled in the art. The adhesive layer 18 has an outer adhesive surface 19 that is exposed when a protective layer (not shown) is removed when the patch is ready for placement in a subject.

As shown in FIGS. 1A-1C, the drug-release layer 20 can be configured to fit into the recess 18 such that an outer drug-release surface 22 of the drug-release layer 20 is exposed to the mucosa (not shown) when in use. The remaining sides and inner surfaces of the drug-release layer 20 can be substantially surrounded by the adhesive layer 14. Both the adhesive layer 14 and the drug-release layer 22 together can form a unitary construction. In such construction, the outer drug-release surface 22 of the drug-release layer 20 is substantially planar with a plane defined by the outer adhesive surface 19 of the adhesive layer 14 such that, when the patch 10 adheres to a mucosal membrane, both the outer drug-release surface 22 and the outer adhesive layer are in contact with the mucosa (not shown).

The dimensions of both the adhesive layer 14 and the drug-release layer 20 are chosen as per the therapeutic agent to be administered and its dosage. The ratio of lengths of both (i.e., diameters in case of a circular recess) can be selected such that the adhesive surface 19 has sufficient area to enable adequate adhesion of the patch 10 to the mucosa. The thickness of the patch 10 is kept at a minimum possible, to ensure least possible foreign body sensation and better patient compliance and mouth-feel. For example, the thickness can range from about 0.5 mm to about 5 mm. While certain embodiments are of a circular shape, alternative shapes of the patch 10 can be easily manufactured. Non-limiting examples of other shapes include oval, ellipsoidal, capsule shape, and the like. In certain embodiments, the shapes lack sharp edges such that the patch is less likely to have raise concerns such as mechanical instability and irritation during use. However, it is to be understood that other modifications to the shape, such as making various geometric shapes or making both the compartments of different shapes are obvious to a person skilled in the art and are contemplated as part of the invention.

The drug-release layer 20 contains a formulation comprising one or more therapeutic agent/agents, and optionally excipients. In certain embodiments, the therapeutic agent can be present in the range of about 0.1 to about 99% w/w, preferably about 1 to about 90% w/w of the patch, depending on its dose and formulation factors.

Formulations and Therapeutic Formulations

The terms "therapeutic formulation/s" and 'formulation/s" can be used interchangeably herein. In one aspect, the formulation includes: at least one mucoadhesive material; at least one active, or therapeutic, agent, such as a retinide composition; and, at least one permeation enhancer agent; and, in certain embodiments, at least one solubilizer agent.

The present invention further provides for a method of treatment and prophylaxis of diseases comprising administering to a subject in need of such treatment, the formulation of the invention.

In certain embodiments, the formulations can include be provided as: a gel, a rinse, and two locally injectable delivery formulations: one that can be delivered from a poly-lactide-co-glycolide, and another that can be delivered as a gel that undergoes hybridization after injection and achieving body temperature.

Mucoadhesive Materials

The formulation includes one or more mucoadhesive materials, optionally in combination with suitable excipients. In certain embodiments, the mucoadhesive material is present in the range of about 1% to about 99% w/w, preferably about 5 to about 95% w/w of the formulation.

Useful examples of mucoadhesive materials include polymers of acrylic acid esters, acrylic acid copolymers, vinyl polymers, vinyl copolymers, polymers of vinyl alcohols, carboxy vinyl polymers and copolymers, vinyl esters, alkoxy polymers, polyethylene oxide polymers, polyethers, and mixtures thereof.

In the examples herein the mucoadhesive materials comprised a methacrylate copolymer. One non-limiting example is commercially available under the tradename Eudragit®, which is a copolymer of ethyl acrylate, methyl methacrylate and a low content of methacrylic acid ester with quaternary ammonium groups. The ammonium groups are present as salts and make the polymers permeable. The Chemical/IUPAC name is poly(ethyl acrylate-co-methyl methacrylate-co-trimethylammonioethyl methacrylate chloride) 1:2:0.1; INCI name: Acrylates/Ammonium Methacrylate Copolymers.

The mucoadhesive material may be admixed with other materials; for example, the mucoadhesive materials may be admixed with optional excipients, such as binders, coloring agents; diluents, enzyme inhibitors, fillers, flavoring agents, lubricants, stabilizers, sweetening agents, and the like.

Therapeutic Agents

The therapeutic formulation described herein is especially useful in the treatment of subjects with precancerous oral epithelial lesions.

Figure 7:
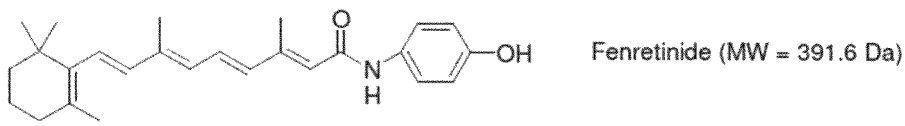
FIG. 7: Chemical structures of fenretinide and the chemical permeation enhancers propylene glycol, L-menthol, and oleic acid.
Figure 7:
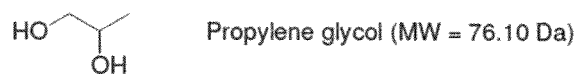
Figure 7:
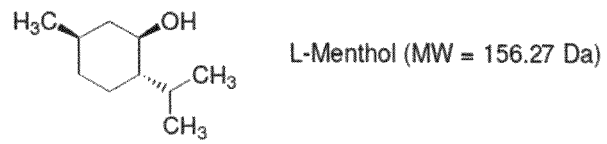
Figure 7:
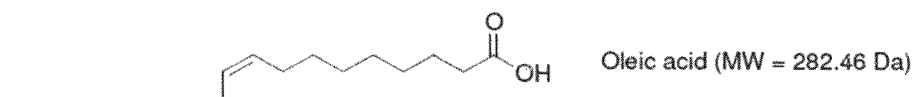

In one particular aspect, the therapeutic agent is a hydrophobic composition, such as synthetic Vitamin A compositions, such as retinide compositions. In a particular embodiment, the mucoadhesive system includes a formulation that is especially useful for the delivery of retinide compositions. In certain embodiments, the retinide composition comprises a synthetic retinoid such as fenretinide. Fenretinide (4-hydroxy(phenyl)retinamide) is a highly lipophilic drug and has a log P of 8.03, which results in minimal buccal mucosal uptake and permeation. The chemical structures of the drug and permeation enhancers are shown in FIG. 7.

In the past, however, the achievement of desired antitumor activity using fenretinide has been limited by low bioavailability (due to low membrane permeability) and rapid elimination from the body respectively after oral and intravenous administration of fenretinide. Therefore, multiple dosing of fenretinide is required to achieve therapeutic drug level in the blood and hence potent oral cancer chemoprevention. The local delivery from hydrogel-based mucoadhesive system provides therapeutic fenretinide level directly at the treatment site, thereby improving the therapeutic efficacy of fenretinide in cancer chemoprevention. However, fenretinide is a highly hydrophobic drug with very low water solubility (below HPLC detection limit). Though fenretinide possesses both desirable epithelial differentiation and apoptotic-inducing capabilities, its previous clinical use has been limited to oral systemic administration.

Transmucosal Permeation Agents

The transmucosal permeation enhancing agents described in more detail herein provide an enhanced delivery profile and more efficient delivery of the therapeutic agent. Additional advantages of the transmucosal permeation enhancing agents are also described herein. For example, in certain embodiments, the transmucosal permeation enhancer agents comprise one or more of: propylene glycol (PG) and terpenoids or terpenes (such as menthol, D-limonene, geraniol, nerolidol) and mixtures thereof.

In one embodiment, the transmucosal permeation enhancer agent is selected from propylene glycol (PG) and menthol. In a particular embodiment, the transmucosal permeation enhancer agent comprises from about 1 wt % to about 2.5 wt % PG, and from 1 wt % to about 5 wt % menthol.

In another embodiment, the transmucosal permeation enhancer agent comprises from about 1 wt % to about 2.5 wt % PG, and about 5 wt % menthol.

In another embodiment, the transmucosal permeation enhancer agent comprises about 1 wt % PG and about 5 wt % menthol.

In yet another embodiment, the transmucosal permeation enhancer agent comprises about 2.5 wt % PG and about 5 wt % menthol.

Solubilizers

In certain embodiment, the formulation includes an effective amount on one or more solubilizers to facilitate continuous in vitro and in vivo release from the mucoadhesive material. To maintain a desired sink condition in the release/receiver chamber medium, appropriate quantity of suitable solubilizing agent can be incorporated. In this Example, the optimal quantity of nonionic surfactant in the release media was selected by matching the drug solubility to that in bovine serum.

Non-limiting examples of solubilizers include, deoxycholic acid, polyoxy-ethylene-sorbitan higher fatty acid esters (e.g., Tween®80).

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

Example 1

Preparation of Hydrogel-Based Controlled Release Fenretinide Mucoadhesive System Preparation of an Adhesive Layer An adhesive layer based on the blend of hydroxypropyl methylcellulose (HPMC 4KM) and polycarbophil (PC) at a weight ratio of 3:1 was prepared by a casting method. Briefly, 1.5% polymer solution was prepared in ddH$_2$O containing required amount (20 wt % based on polymer mass) of propylene glycol by stirring the polymer/water mixture overnight. About 50 mL of polymer solution was then casted onto glass petri dish (150×20 mm) and incubated at 50° C. for 48 h. Then, the polymer film was cut into required size and stored in a desiccator at room temperature until further use.

Preparation of Drug-Release (Fenretinide) Layer/Film

Preparation of fenretinide films was performed under the protection from light. A desired quantity of solubilizer (Tween® 80 and sodium deoxycholate), permeation enhancers (1, 2.5, 5, and 10 wt %) and mucoadhesive material, Eudragit® RL PO, were weighed in 15 mL polypropylene tubes to which 8 mL of a 50:50 (v/v) acetone-ethanol mixture was added. The quantity of plasticizer or solubilizer added was calculated based on the mass of polymer. The resulting mixture was vortexed until all ingredients were dissolved. The required quantity (5 wt % based on the total mass of polymer+excipients) of fenretinide was then added to above prepared polymer-solubilizer or polymer-solubilizer-permeation enhancer(s) solution, vortexed again, and the volume was adjusted to 10 mL with the same solvent mixture. Five milliliter of fenretinide-polymer solution was added onto Teflon (Scientific Commodities, Inc., Lake Havasu City, Ariz., USA) overlaid glass petri dish (60×15 mm) and incubated at 38° C. for 48 h. After sufficient drying, fenretinide loaded polymer film was cut into required size (7 mm diameter), packed in aluminum foil, and stored in a desiccator at −20° C. until further use.

Assembly of Oral Mucoadhesive Patches of Fenretinide

Figure 1D:
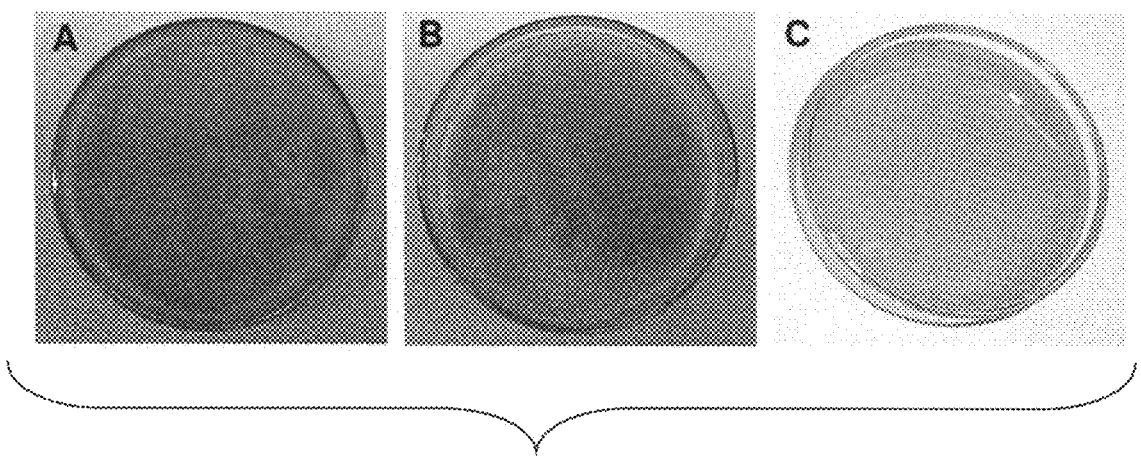
FIG. 1D: Photographs of the fenretinide/Eudragit® (drug release) layer loaded with 5 wt % menthol (photograph A), 10% menthol (photograph B), and 1 wt % PG+5 wt % menthol (photograph C).

An annular adhesive layer with 11 (outer diameter) and 7 (inner diameter) mm dimensions were formed by cutting the film with 11 and 7 mm cork borers, respectively. The adhesive layer was then placed onto adhesive side of the Tegaderm™ film (backing layer), followed by insertion of previously cut 7 mm fenretinide/Eudragit® layer into open region of adhesive layer to obtain oral mucoadhesive patch of fenretinide. FIG. 1D shows the physical appearance of the fenretinide/Eudragit® (drug-release) layer loaded with 5 wt % menthol (photograph A), 10% menthol (photograph B), and 1 wt % PG+5 wt % menthol (photograph C).

Effect of Co-Incorporation of Menthol on Fenretinide/Eudragit® RL PO Film Morphology Fenretinide/Eudragit® RL PO (drug-release) films without menthol exhibited good film forming and physical appearance. Fenretinide/Eudragit® RL PO films loaded with 5% or 10% menthol did not exhibit good film forming and physical appearance (see photograph A and photograph B in FIG. 1D). It appeared that that phase separation occurred during the film formation due to formation precipitation and/or aggregation of menthol. As shown in photograph C in FIG. 1D, the addition of 1% PG as a co-solvent facilitated desirable film formation.

Solubilization of Fenretinide in Simulated Saliva with Variety of Solubilizers

The extent of solubility enhancement of fenretinide by numerous solubilizers (bile salts, surfactants, hydrophilic polymers, and co-solvents) was studied by determining the solubility in simulated saliva in the presence of 0.5, 1, 2, and 5% w/v solubilizers. Briefly, an excess amount of fenretinide was added into separate amber color ampoules containing 1-mL 0.5, 1, 2, and 5% w/v solutions of solubilizers (prepared using $N_2$-purged simulated saliva) and sealed under vacuum in order remove the oxygen from the head-space. The ampoules were then placed in an incubator maintained at 37° C. and shaken at 240 RPM for 72 h (this duration was determined to be sufficient to reach the equilibrium). After 72 h, the ampoules were broken, mixture was passed through 0.45 µm PVDF filter units (Millipore, USA), diluted suitably with respective solubilizer solution, and the amount of fenretinide solubilized in simulated saliva was determined by HPLC.

Results for Example 1

Figure 2A:
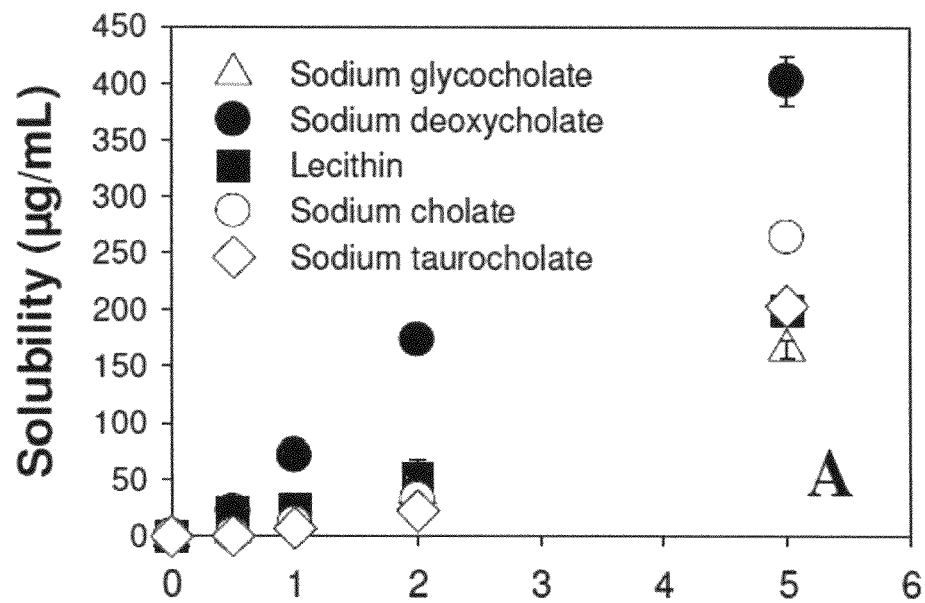
FIGS. 2A-C: Graphs showing solubilization of fenretinide in simulated saliva (buffer, pH 6.8). Effect of addition of bile salt/lecithin (FIG. 2A), surfactant (FIG. 2B), and hydrophilic polymer (FIG. 2C) on the solubility of fenretinide in simulated saliva. Solubility of fenretinide in simulated saliva in the presence of 0.5, 1, 2, and 5% w/v solubilizers at 37° C. Values represent mean±SE, n=3.
Figure 2B:
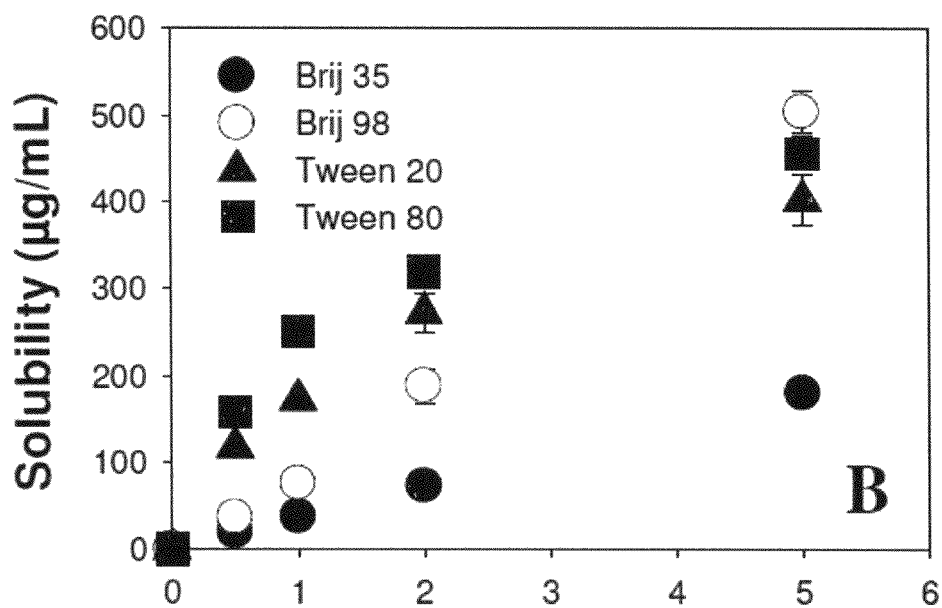
Figure 2C:
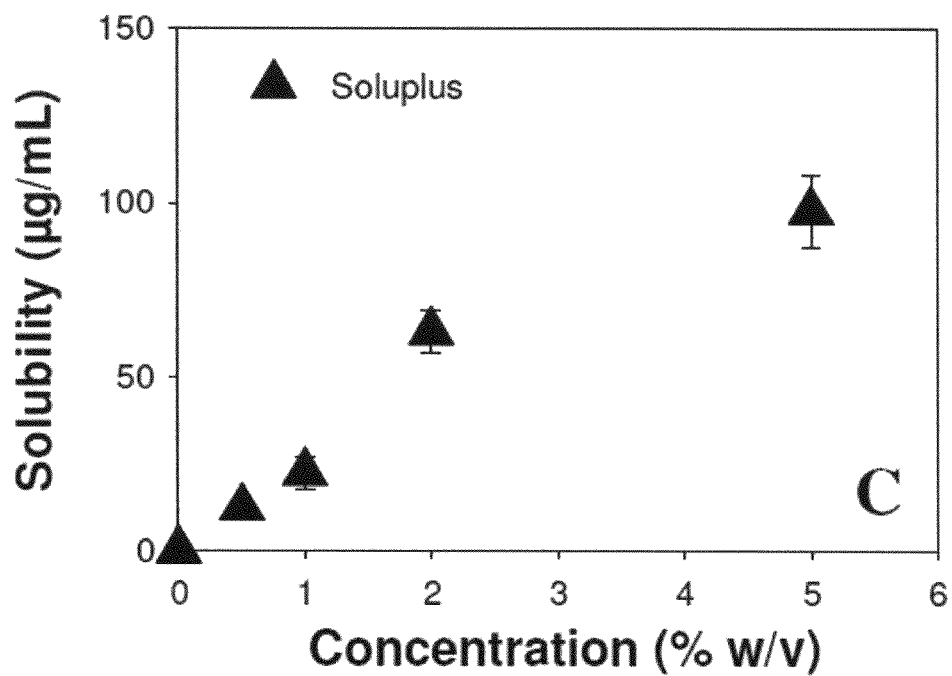

FIGS. 2A-2C show graphs illustrating the solubilization of fenretinide in simulated saliva (buffer, pH 6.8). Effect of addition of bile salt/lecithin (FIG. 2A), surfactant (FIG. 2B), and hydrophilic polymer (FIG. 2C) on the solubility of fenretinide in simulated saliva. Solubility of fenretinide in simulated saliva in the presence of 0.5, 1, 2, and 5% w/v solubilizers at 37° C. Values represent mean±SE, n=3.

Table 1 below shows examples of formulations of hydrogel-based controlled release fenretinide mucoadhesive system that were evaluated.

TABLE 1

Compositions of hydrogel-based controlled release fenretinide mucoadhesive system Adhesive layer
1) HPMC 4KM
2) Polycarbophil
3) Propylene glycol Drug (fenretinide)-release layer
A) Solubilizer-free fenretinide layer
   1) Fenretinide
   2) Eudragit ® polymer
   3) Triacetyl citrate
B) Solubilizer-loaded fenretinide layer
   1) Fenretinide
   2) Eudragit ® polymer
   3) Solubilizer
      Tween ® 20 or Tween ® 80 of Brij 98 of Sodium deoxycholate The fenretinide loading efficiency of Eudragit® RS PO/RL PO films is shown in Table 2 below.

TABLE 2

Evaluation of microencapsulation of fenretinide in solubilizer-free and solubilizers loaded Eudragit ® RS PO/RL-PO films

| Formulation | Fenretinide Loading Theoretical$^a$ (wt %) | Actual (wt %)* | Loading Efficiency (%)* |
|---|---|---|---|
| Eudragit ® RS-PO | 5.0 | 4.5 ± 0.1 | 90.0 ± 1.2 |
| Solubilizer-free Eudragit ® RL-PO | | | |
| | 5.0 | 4.6 ± 0.1 | 92.1 ± 1.0 |
| | 10.0 | 9.2 ± 0.2 | 92.0 ± 2.0 |
| Solubilizers Loaded Eudragit ® RL-PO | | | |
| 20 wt % Tween ® 20 | 5.6 | 5.4 ± 0.1 | 96.3 ± 1.5 |
| 20 wt % Tween ® 80 | 5.1 | 4.9 ± 0.2 | 95.1 ± 1.6 |
| 20 wt % Brij 98 | 5.2 | 4.8 ± 0.1 | 92.3 ± 1.5 |
| 20 wt % Sodium deoxycholate | 5.6 | 5.5 ± 0.2 | 97.0 ± 1.0 |
| 40 wt % Sodium deoxycholate | 5.0 | 4.6 ± 0.1 | 91.4 ± 1.0 |
| 20 wt % Tween ® 80 + 40 wt % Sodium deoxycholate | 4.9 | 4.5 ± 0.2 | 92.0 ± 2.1 |

*Mean ± SE, n = 3;
$^a$Based on polymer + excipients weight

Identification of Suitable Release Medium to Maintain Sink Condition During In Vitro Drug-Release The drug is insoluble in simulated saliva (pH 6.8). Therefore, it is not possible to maintain the sink condition in simulated saliva during the in vitro drug-release studies. To maintain the sink condition, 2.5 and 5% (w/v) sodium deoxycholate was added into the simulated saliva. In certain embodiments, the solubilizer used to maintain sink condition is inert and does not change the drug release characteristics of film. To understand phenomenon, in vitro release study of fenretinide from Eudragit® films in simulated saliva containing 2.5 and 5% (w/v) sodium deoxycholate was performed.

Figure 3:
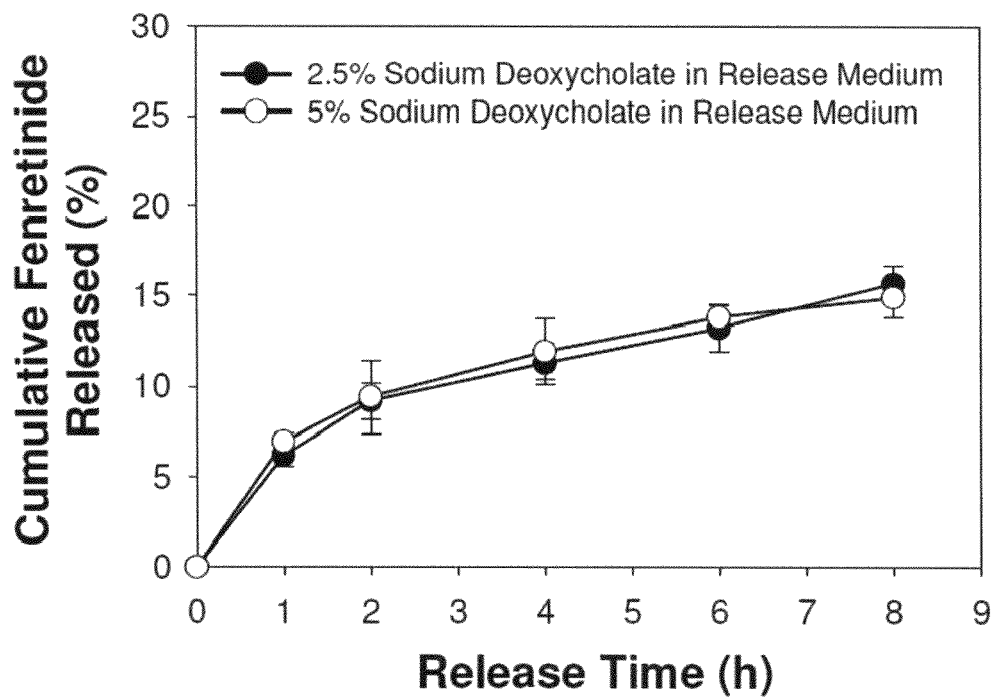
FIG. 3: Graph showing effect of addition of sodium deoxycholate in simulated saliva (pH 6.8) on cumulative release of fenretinide from Eudragit® RS-PO film. Drug loading was 5 wt %.

FIG. 3 illustrates the effect of addition of sodium deoxycholate in simulated saliva (pH 6.8) on cumulative release of fenretinide from Eudragit® RS-PO film. Drug loading was 5 wt %. The addition of different fraction of sodium deoxycholate did not change the drug release characteristics of polymer film, suggesting that the solubilizer is inert and can be used to maintain sink condition in the simulated saliva. Further release studies were conducted in simulated saliva containing 5% w/v sodium deoxycholate.

Figure 4:
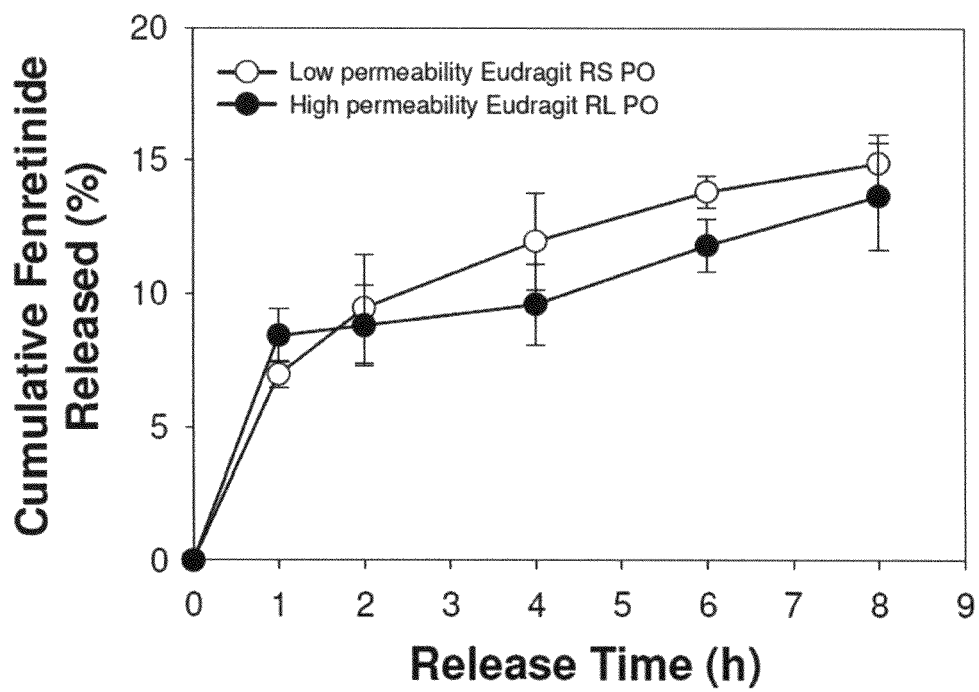
FIG. 4: Graph showing effect of polymer matrix permeability on cumulative release of fenretinide from Eudragit® film. Drug loading was 5 wt %. Release study was conducted in simulated saliva (buffer, pH 6.8) containing 5% w/v sodium deoxycholate at 37° C. Values represent mean±SE, n=3.

Effect of Polymer Matrix Permeability on In Vitro Release of Fenretinide from Eudragit® Films FIG. 4 illustrates the effect of polymer matrix permeability on cumulative release of fenretinide from Eudragit® film. Drug loading was 5 wt %. Release study was conducted in simulated saliva (buffer, pH 6.8) containing 5% w/v sodium deoxycholate at 37° C. Values represent mean±SE, n=3.

Figure 5:
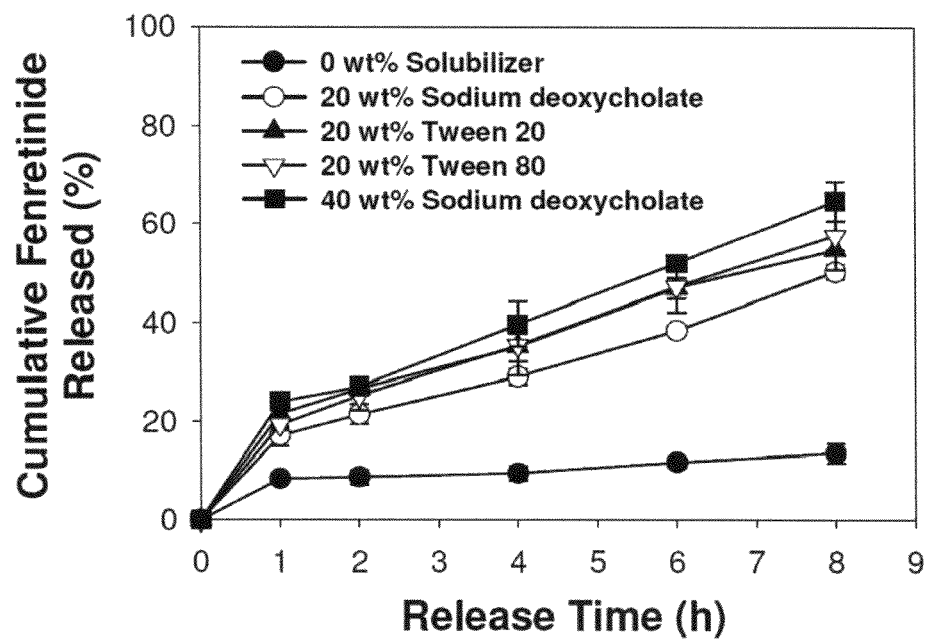
FIG. 5: Graph showing effect of co-encapsulation of solubilizer on cumulative release of fenretinide from Eudragit® RL PO film. Drug loading was 5 wt %. Release study was conducted in simulated saliva (buffer, pH 6.8) containing 5% w/v sodium deoxycholate at 37° C. Values represent mean±SE, n=3.

Effect of Co-Encapsulation of Solubilizer on In Vitro Release of Fenretinide from Eudragit® Films FIG. 5 illustrates the effect of co-encapsulation of solubilizer on cumulative release of fenretinide from Eudragit® RL PO film. Drug loading was 5 wt %. Release study was conducted in simulated saliva (buffer, pH 6.8) containing 5% w/v sodium deoxycholate at 37° C. Values represent mean±SE, n=3.

Figure 6:
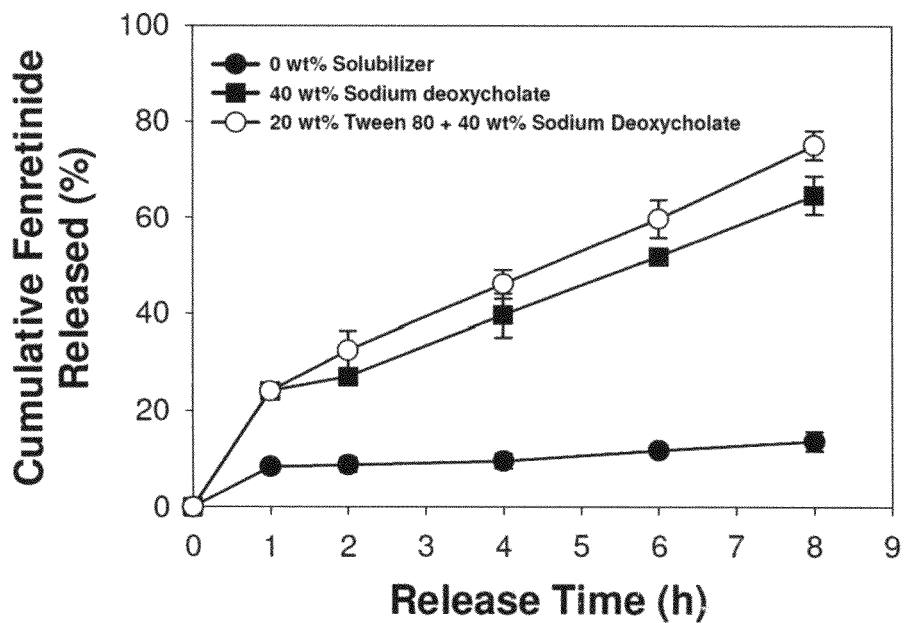
FIG. 6: Graph showing effect of co-encapsulation of mixed solubilizers on cumulative release of fenretinide from Eudragit® RL PO film. Drug loading was 5 wt %. Release study was conducted in simulated saliva (buffer, pH 6.8) containing 5% w/v sodium deoxycholate at 37° C. Values represent mean±SE, n=3.

FIG. 6 illustrates the effect of co-encapsulation of mixed solubilizers on cumulative release of fenretinide from Eudragit® RL PO film. Drug loading was 5 wt %. Release study was conducted in simulated saliva (buffer, pH 6.8) containing 5% w/v sodium deoxycholate at 37° C. Values represent mean±SE, n=3.

The release of fenretinide from solubilizer-free Eudragit® RL PO/RS PO films was very slow (13-15% release after 8 h). Co-encapsulation of single (17-22 and 50-58% release, respectively, after 1 and 8 h from 20 wt % Tween® 20 and 80 and sodium deoxycholate loaded films) or mixed (24 and 75% release respectively after 1 and 8 h from 20 wt % Tween® 80+40 wt % sodium deoxycholate loaded film) solubilizers in fenretinide/Eudragit® RL PO films led to significant improvement in drug-release over a period of 8 h.

Example 2

Materials

Sodium deoxycholate (Sigma-Aldrich, Co., St. Louis, Mo.), Tween® 80 (Sigma-Aldrich, Co., St. Louis, Mo.), Eudragit® RL-PO (Rohm GmbH, Pharma Polymers, Darmstadt, Germany), propylene glycol (MP Biomedicals, LLC, Solon, Ohio). Fenretinide (MK-4016) was provided by Merck Corp.

Porcine buccal tissue was obtained from local slaughterhouse and used within 2 hours of slaughter. Tissue was kept on ice during transit. The epithelium was separated from the underlying connective tissue with surgical technique.

Methods for Example 2

Preparation of Oral Patch

Various types of mucoadhesive layers were prepared by a casting method. Briefly, about 50 mL polymer solutions (1.5% w/v) of various mucoadhesive polymers were each prepared in water by stirring overnight and poured into glass Petri dishes. The water was evaporated by incubating the Petri dishes at 50° C. for 24 h. The films were then removed and stored in a desiccator until further use.

The drug layer was also prepared by a casting method using Eudragit® RL-PO polymer. Briefly, 12% (w/w) Tween® 80, 33% (w/w) sodium deoxylcholate, 5% (w/w) fenretinide, 50% (w/w) Eudragit® RL-PO and 5% (w/w) or 10% (w/w) permeation enhancers were dissolved in 10 ml acetone:ethanol (50:50). All the weight to weight ratios were based on the total amount of polymer, excipients and drug.

The solution was casted onto Teflon coated Petri dishes. The Petri dishes were then incubated at 37° C. for 24 h. The films were removed and stored in a desiccator at −20° C. until further use.

Determination of Fenretinide Solubility in Bovine Serum

Excessive amount of fenretinide was added into fetal bovine serum in polypropylene tubes. The sample was placed on a mechanical circulator and incubated at 37 C avoiding light. At every 24 hours (until fenretinide reached saturation in serum), the sample was centrifuged at 8000 rpm for 10 minutes. 0.2 ml sample was drawn from the supernatant. This volume was immediately replaced using blank serum. The tubes were shook to mix the supernatant and sediment, and then re-placed on the mechanical circulator and incubated at 37 C. The fenretinide concentration in the supernatant was measured by a HPLC assay after extraction using acetonitrile.

In Vitro Permeation

In vitro permeation studies were investigated using a side-by-side Franz diffusion cell apparatus. The orifice diameter in both donor and receptor compartments was 1 cm (0.785 $cm^2$). Porcine buccal membrane was mounted between donor and receiver compartments of the diffusion cell. Fenretinide patches were placed on surface side of buccal membrane, in such a way that the backing layer faced the donor chamber and the adhesive film facing the membrane. The receptor compartment held phosphate buffered saline (PBS, pH=7.4) containing 0.084% Tween 80 (v/v), which was degassed prior to use by vacuum filtration through a HPLC filter. The donor compartment held saliva buffer. Compartment temperature was kept constant at 37° C. by recirculating water from a thermostatically controlled bath. Continuous stirring was provided by stirring bar, rotating at 600 rpm. 1 ml samples were collected from the receptor compartment at defined time intervals (1, 2, 3, 4, 5, 6, 7, 8 and 12 h). This volume was immediately replaced using blank, pre-warmed PBS buffer. The samples were then analyzed by HPLC.

Fenretinide HPLC Assay

HPLC assays were performed on a Waters 2695 alliance system (Milford, Mass., USA) consisting of a 2996 Photodiode array detector and a personal computer with Empower 2 Software. A symmetry C18 column (4 μm, 150 mm×4.6 mm) was used. Isocratic elution with acetonitrile: 0.1% (v/v) phosphoric acid (67:33 v/v) was employed at a flow rate of 1.0 ml/min and detection wavelength was set at 365 nm. Volume of injection was 50 μl. All samples were analyzed at room temperature. Standard curve of fenretinide was established in acetonitrile:ethanol (50:50) and concentration of unknown samples was calculated from the standard curve.

Results for Example 2

Fenretinide Solubility in Bovine Serum

The solubility of fenretinide in serum after 6 days incubation was 20.945±1.022 μg/ml. As the intrinsic aqueous solubility of fenretinide is extremely low (0.0098 μg/ml) (practically insoluble in water), the fenretinide concentrations achieved in serum might be fenretinide bound to serum proteins, such as albumin, lipoproteins and serum retinol-binding protein (RBP). RBP, a glycoprotein, is a well-characterized protein which transports retinol in plasma. It consists of a single polypeptide chain of 21 kDa which binds one molecule of retinol. It forms a complex with all-trans retinol (ATRol) in the liver and is involved in the transport of ATRol in the blood. Fenretinide also interacts with RBP to form a tight complex, but the affinity is lower than that of retinol.

The inventors herein have shown that the addition of Tween® 80 can improve the solubility of fenretinide. Therefore, to mimic the physiological conditions inside the body, in vitro permeation studies were performed in the presence of 0.084% Tween 80 (v/v) in the receiver containing PBS buffer (pH 7.4) as the solubility of fenretinide in serum is equal to that in 0.084% Tween 80 (v/v) solution.

Permeation of Fenretinide Through Porcine Buccal Tissue

Figure 8:
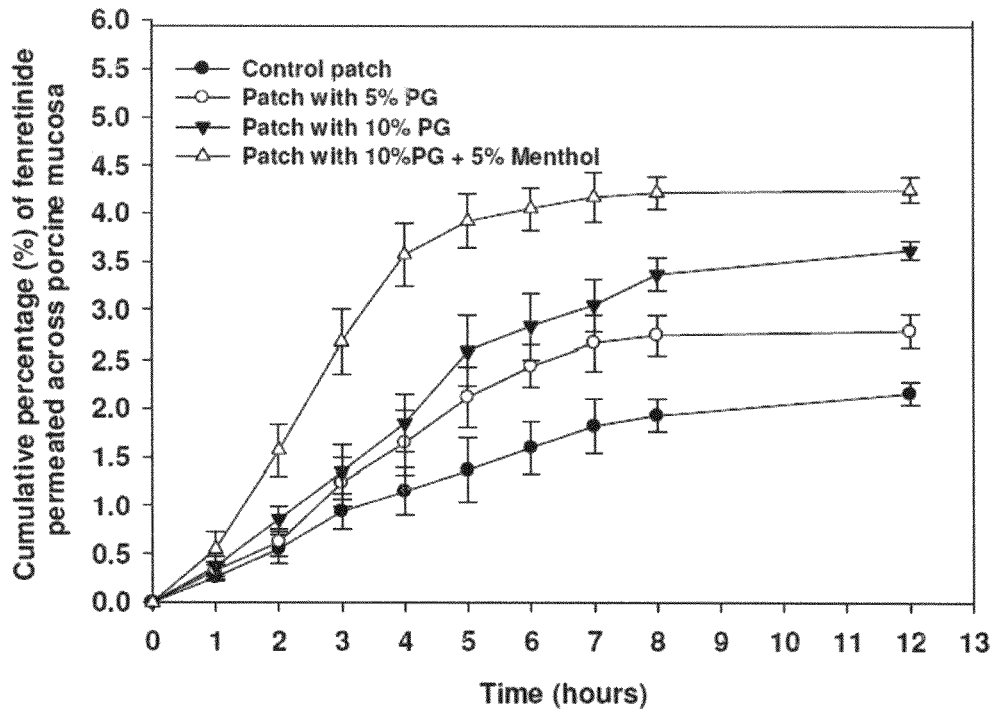
FIG. 8: Graph showing cumulative percentage versus time profiles of fenretinide permeated across porcine buccal mucosa from patches with/without propylene glycol (mean±SD, n=3).
Figure 9:
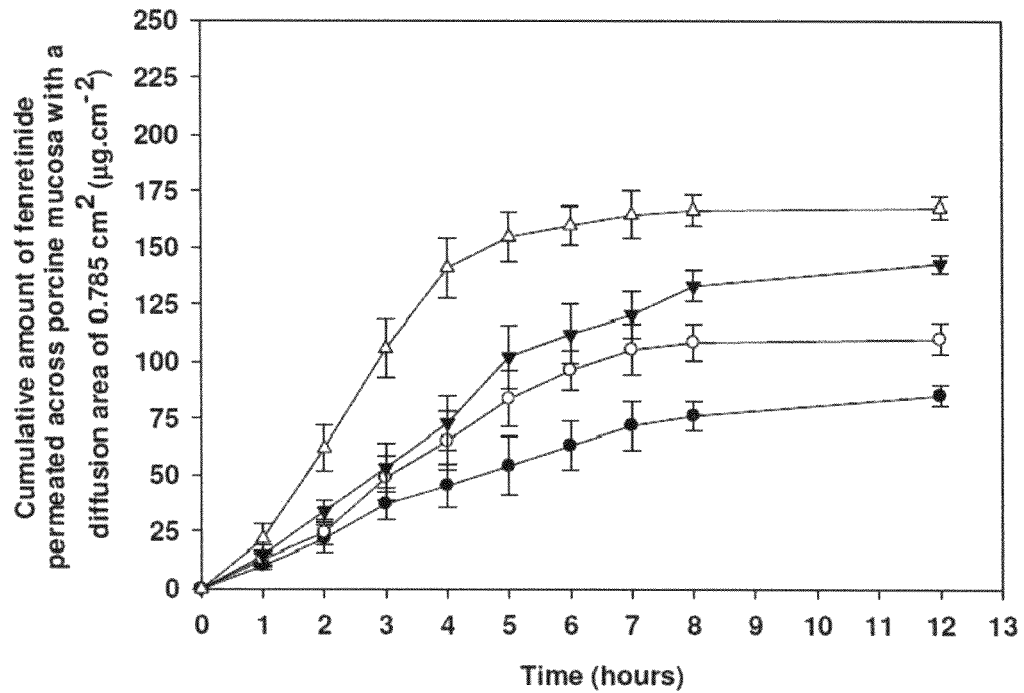
FIG. 9: Graph showing cumulative amount versus time profiles of fenretinide permeated across porcine buccal mucosa from patches with/without propylene glycol (mean±SD, n=3).

Permeation profiles of fenretinide, i.e., cumulative percentages and amounts of fenretinide permeated through porcine buccal mucosa plotted against time, are shown in FIG. 8 and FIG. 9, respectively. The FIGS. 8-9 show that the co-solvent system described herein enhances oral mucosal permeation of fenretinide. In particular, there is an enhancement of oral mucosal permeation of fenretinide by co-incorporation of propylene glycol (co-solvent) in the hydrogel-based fenretinide controlled release system.

The steady state flux ($J_s$), cumulative amounts and percentages of fenretinide in the receiver and tissue, and enhancement factors from PG-incorporated patches are shown in Table 3.

menthol improves the permeation of drugs by increasing the drug diffusivity in the membrane by modifying the intercellular packing, disrupting highly ordered structure of lipids.

Propylene glycol has an effect on the enhancement of buccal mucosa permeation and retention of fenretinide. The combination of other enhancers with propylene glycol provides a synergistic effect and significantly increases the activity of enhancers. As such, in certain embodiments, there is also provided herein methods and buccal patches containing PG and other permeation enhancer (e.g., L-menthol, oleic acid).

Example 3

Chemicals, Tissue, and Animals

Fenretinide was received as a gift sample from Merck & Co., Inc. (Whitehouse Station, N.J.). Sodium deoxycholate, Tween® 80 and L-menthol were purchased from Sigma-Aldrich, Co. (St. Louis, Mo.). Noveon® AA-1 polycarbophil (PC), hydroxypropyl methylcellulose (HPMC) 4KM and Eudragit® RL-PO were all gifts from Lubrizol Corp. (Wickliffe, Ohio), Colorcon®, Inc., (West point, Pa.), and Evonik Degussa Corp. (Piscataway, N.J.), respectively. Propylene glycol was purchased from MP Biomedicals, LLC (Solon, Ohio). Teflon® overlay was purchased from Scientific Commodities, Inc., (Lake Havasu City, Ariz.). Tegaderm™ roll was purchased from 3M Health Care (St. Paul, Minn.). Porcine buccal tissue was obtained from slaughter house

TABLE 3

Evaluation of oral mucosal permeation enhancement characteristics of propylene glycol for fenretinide

| Formulation | J, (µg cm$^{-2}$ h$^{-1}$)[a] | Cumulative amount of fenretinide in the receptor $Q_{126}$ (µg) | Cumulative percentage of fenretinide in the receptor fluid $Q_{126}$ (%) | Fenretinide amount in the tissue (µg) | Fenretinide percentage in the tissue (µg) | EF for fenretinide in the receptor[b] | EF for fenretinide in the tissue[c] |
|---|---|---|---|---|---|---|---|
| Control | 10.03 ± 1.03 | 66.96 ± 3.72 | 2.16 ± 0.12 | 234.05 ± 45.88 | 7.55 ± 1.48 | 1 | 1 |
| Propylene glycol 5% | 16.19 ± 2.21 | 86.49 ± 5.27 | 2.79 ± 0.17 | 504.06 ± 33.79 | 16.26 ± 1.09 | 1.3 | 2.2 |
| Propylene glycol 10% | 22.77 ± 2.90 | 112.22 ± 3.10 | 3.62 ± 0.10 | 616.28 ± 40.92 | 19.88 ± 1.32 | 1.7 | 2.6 |
| Propylene glycol 10% + Menthol 5% | 39.75 ± 2.11 | 131.75 ± 4.03 | 4.25 ± 0.13 | 908.92 ± 84.32 | 29.32 ± 2.72 | 2.0 | 3.9 |

[a]J, steady sate fluxes obtained from the slope of the graph of cumulative amount permeated versus time. (the linear portion of the concentration-time profiles).
[b]Enhancement factor (EF) = cumulative percentage of fenretinide in the receiver from patch with enhancer/cumulative percentage of fenretinide in the receiver from control patch.
[c]Enhancement factor (EF) = fenretinide percentage in the tissue from patch with enhancer/fenretinide percentage in the tissue from control patch.

The results in Table 3 demonstrate that patches containing both 5% and 10% PG increased buccal mucosa permeation and retention of fenretinide. This enhancement was in a greater extent when more PG (10%) was incorporated into the patch. Propylene glycol enters the buccal tissue, competes for the solvation sites of the polar head groups of the lipid bilayers and increases the solubility of this site for the permeant. As a consequence, the partitioning of the drug from the patch into the buccal tissue increases.

When 5% menthol was incorporated into the patch which contained 10% PG, much more drug (3.9 times in comparison with patch without enhancer) was recovered from the buccal tissue. As terpenes can enhance both hydrophilic drugs including propranolol and lipophilic drugs such as testosterone. This permeation enhancement results from the synergistic effect of propylene glycol and menthol. The (Dunbar Meat Packing Company, Milan, Mich., USA). Rabbits were purchased from Harlan Laboratories (Indianapolis, Ind., USA).

Preparation of Oral Mucoadhesive Patches for Enhanced Buccal Permeation of Fenretinide.

Fenretinide/Eudragit® RL-PO/solubilizers patches with and without permeation enhancers (PG and menthol) were prepared by a solvent casting and assembly techniques as described herein. Three steps were involved in the preparation of fenretinide patch: formation of adhesive (hydroxypropyl methylcellulose and polycarbophil at a weight ratio of 3:1) and drug release (5 wt % fenretinide/Eudragit® RL-PO/40 wt % sodium deoxycholate/20 wt % Tween® 80) layers, and assembly of adhesive and drug release layers onto backing layer (Tegaderm™ film) (see FIGS. 1A-1C. The drug release (fenretinide) layer included permeation enhancer(s) in addition to the formulation given above. Eudragit® RL-PO/5 wt % fenretinide/40 wt % sodium deoxycholate/20 wt % Tween® 80 layer loaded with PG alone (5 and 10 wt %) or menthol alone (5 and 10 wt %) or in combination (1 wt % PG+5 wt % menthol, 2.5 wt % PG+5 wt % menthol, and 10 wt % PG+5 wt % menthol) were prepared Fenretinide HPLC Assay.

HPLC assays were performed on a Waters 2695 alliance system (Milford, Mass., USA) consisting of a 2996 Photodiode array detector and a personal computer with Empower 2 Software. A symmetry C18 column (4 µm, 150 mm×4.6 mm) was used. Isocratic elution with acetonitrile: 0.1% (v/v) phosphoric acid (67:33 v/v) was employed at a flow rate of 1.0 mL/min and detection wavelength was set at 365 nm. Standard curve of fenretinide was established in acetonitrile: ethanol (50:50) and concentration of unknown samples was calculated from the standard curve.

Determination of Fenretinide Solubility in Bovine Serum.

A known quantity (0.9, 2.26, 3.97, 8.03, and 20.5 mg) of fenretinide was added to polypropylene tubes containing 15 mL fetal bovine serum. The samples were incubated at 37° C. under constant rotation using a rigged rotator and protection from light. At every 24 h till 7 days, the samples were centrifuged at 8000 rpm for 10 minutes and 200 µl of supernatant was withdrawn. Withdrawn serum sample was replaced with fresh serum sample, mixed properly, and incubated again under similar conditions. To the withdrawn sample (200 µl), 2 mL of acetonitrile was added, agitated overnight on a mechanical shaker with protection from light, passed through 0.45 µm PVDF filter units, and analyzed by HPLC.

Determination of Fenretinide Loading.

Fenretinide/Eudragit® films were digested in acetonitrile: ethanol (50:50), passed through 0.45 µm PVDF filter units, and analyzed by HPLC after suitable dilution. The fenretinide loading was calculated as the percentage of the amount of fenretinide versus the total weight of the film mixture (i.e., fenretinide, Eudragit®, and other excipients).

Evaluation of In vitro Release of Fenretinide from Oral Mucoadhesive Patches.

Simulated saliva comprised of 14.4, 16.1, 1.3, 0.55, and 2 mM sodium chloride, potassium chloride, calcium chloride dihydrate, magnesium chloride hexahydrate, and dibasic potassium phosphate and the pH was adjusted to 6.8. In vitro release studies were conducted in simulated saliva containing 5% (w/v) sodium deoxycholate under perfect sink conditions. Mucoadhesive patches were placed in 50 mL tubes (separate tubes for each sampling interval) and 40 mL release medium was added to each tube. The tubes were placed in an incubator maintained at 37° C. and shaken at 100 RPM. At predetermined time intervals (0.5, 3, and 6 h), tubes were taken out and the patches were immediately freeze-dried. The amount of fenretinide remaining in the patch was determined as per the method described in loading assay. The cumulative amount of fenretinide released was calculated by subtracting the fraction remaining in the patches from the initial drug content.

Ex Vivo Permeation of Fenretinide across Porcine Buccal Mucosa.

Ex vivo permeation of fenretinide across porcine buccal mucosa was conducted using side-by-side flow-through diffusion cells (donor and receiver chamber volume=3 mL). The diffusional interface was a spherical shape with a diameter of 1 cm. Porcine buccal tissue was obtained from a local slaughterhouse and used within 2 hours of slaughter. The tissue was stored in Krebs buffer at 4° C. upon removal. The epithelium was separated from the underlying connective tissue with a scalpel and mounted between the donor and the receiver chambers. Fenretinide patch was then attached to the buccal mucosa (adhesive layer facing mucosa and backing layer exposed to buffer) in donor chamber. Donor and receiver chambers were filled with 3 mL degassed phosphate buffered saline (PBS, pH=7.4) containing 0.084% Tween® 80 (v/v) and simulated saliva (pH 6.8), respectively. Both the chambers were maintained at 37° C. by circulating the water from a thermostatically controlled water bath. The receiver chamber medium was stirred at 600 rpm. After specified duration (1, 2, 3, 4, 5, 6, 7, 8 and 12 h), 1 mL sample was withdrawn from the receiver chamber and immediately replaced with fresh medium. Fenretinide was quantified by HPLC. At the end of permeation study, phenol red at a concentration of 300 µg/ml was added to the donor chamber to check the integrity of buccal mucosa. Phenol red acts as a marker compound, which does not permeate through an intact porcine buccal membrane. Upon the completion of ex vivo permeation study, porcine buccal tissue was removed and fenretinide level in the tissue was determined as described below.

Determination of Fenretinide Levels in Buccal Tissue.

Treated porcine buccal tissue was cut into small pieces and placed in 4-mL polypropylene tubes. One milliliter of water was added to the tubes and homogenized for 1 minute. Then, 2 mL of acetonitrile was added to the tubes and vortexed for 1 hour. After 1 h, tubes were centrifuged at 2600 g at 25° C. for 20 min and the supernatant was analyzed by HPLC to determine fenretinide content.

Haematoxylin and Eosin Staining.

A portion of each tissue was fixed in buffered 10% formalin and embedded in paraffin wax. Then, 5 µm sections were placed on microscope slides, deparaffinized using xylene, and rehydrated using ethanol solutions in a gradient of 80% up to 100% and distilled water. The tissue slices were placed in 0.7% w/w haematoxylin solution, rinsed twice in acid ethanol (0.1 N HCl in 95% ethanol) to remove the excess stain. Subsequently, the tissue slices were placed in 0.1% w/w eosin solution and dehydrated using solutions of ethanol in a gradient of 80% up to 100% and then xylene.

Light Microscopy Analysis.

Light microscopy was performed using Olympus BX51 microscope (Olympus, Tokyo, Japan) at 40× magnification. Images of the sections were captured using a fitted camera (Olympus DP70 digital camera, Tokyo, Japan), and software (Olympus DP controller, Tokyo, Japan).

Evaluation of In vivo Fenretinide Release and Permeation.

Animal studies were approved by the Ohio State University Institutional Animal Care and Use Committee and adhered to National Institute of Health guidelines. Female New Zealand white rabbits (12 weeks old and weight ranging 2.7-3.1 kg) were anesthetized with isoflurane (5% v/v in oxygen) via inhalation for patch placement and removal. Six fenretinide oral mucoadhesive patches/time point were placed on the buccal mucosa of subject rabbit's oral cavity (drug+adhesive layers facing the mucosa). Slight pressure was applied to the backing layer of the patch for 1 minute to establish mucoadhesion with the rabbit buccal mucosa. After different attachment times (0.5, 3 and 6 h), the patches were carefully removed and remaining fenretinide in patches was determined by HPLC. The cumulative amount of fenretinide released was determined by subtracting the fraction remaining in the patches from the initial drug content. To determine the drug level in the tissue, extraction and quantitation of fenretinide was performed as described in the determination of fenretinide level in buccal tissue section.

Statistical Analysis.

The results are expressed as mean±SE (n=3/4 (in vitro) or 5 (ex vivo) or 6 (in vivo)). An unpaired Student's t-test and one-way ANOVA were used to compare the means of in vitro and in vivo drug release, ex vivo porcine buccal mucosal permeation and tissue levels of fenretinide, in vivo tissue levels of fenretinide and assess statistical significance. Results were considered statistically significant if p<0.001.

Discussion of Example 3

Mucoadhesive Fenretinide Patches with Enhanced Drug Permeability.

As described herein, the mucoadhesive patch formulation of fenretinide was tested for site-specific chemoprevention of oral cancer. Solubilizer-free patches exhibited poor in vitro and in vivo drug release behavior. Co-incorporation of either single or mixed solubilizers (e.g., Tween® 20 and 80, sodium deoxycholate) in fenretinide/Eudragit® patches led to significantly improved continuous in vitro and in vivo fenretinide release. In the past, the use of fenretinide in chemoprevention of oral cancer has been hindered by several key limitations, e.g., poor solubility, biological membrane permeability and bioavailability, and rapid elimination of drug from the body. Undesired effects are rendered mainly by its extremely high hydrophobicity (log P=8.03) and low water solubility (below detection limit).

Fenretinide-loaded Eudragit® RL PO layers with and without permeation enhancers were prepared by a solvent casting method with drug loading efficiency of 90-95%, as seen in Table 4.

TABLE 4

Evaluation of Microencapsulation of Fenretinide in Permeation Enhancer-Free and Permeation Enhancers-Loaded Eudragit® RL-PO Films.

| Patch formulation | Fenretinide loading (wt %) | | Loading efficiency |
|---|---|---|---|
| | Theoretical[a] | Actual* | (%)* |
| Permeation enhancer-free | 5.26 | 4.76 ± 0.06 | 90.44 ± 1.14 |
| 5 wt % PG | 5.00 | 4.59 ± 0.07 | 91.81 ± 1.40 |
| 10 wt % PG | 4.76 | 4.52 ± 0.12 | 94.94 ± 2.52 |
| 5 wt % Menthol | 5.00 | 4.62 ± 0.06 | 92.40 ± 1.20 |
| 10 wt % Menthol | 4.76 | 4.51 ± 0.11 | 94.71 ± 2.31 |
| 1 wt % PG + 5 wt % Menthol | 4.95 | 4.48 ± 0.13 | 90.50 ± 2.63 |
| 2.5 wt % PG + 5 wt % Menthol | 4.88 | 4.53 ± 0.11 | 92.87 ± 2.26 |
| 10 wt % PG + 5 wt % Menthol | 4.54 | 4.14 ± 0.05 | 91.10 ± 1.10 |

*Mean ± SE, n = 3;
[a]Based on polymer + excipients weight

The thickness of fenretinide and adhesive layers, and the Tegaderm™ adhesive film were measured to be ~0.28, 0.28, and 0.05 mm, respectively. After assembling drug and adhesive layers onto backing layer, the total thickness of the patch was measured to be ~0.33 mm.

Determination of Optimal Quantity of Surfactant to Maintain Ex vivo Sink Condition for Fenretinide: Solubility of Fenretinide in Bovine Serum.

Sink condition is one of the key features that govern in vitro release or ex vivo biological membrane permeability of hydrophobic drugs. The process of ex vivo drug transport from the patch (donor compartment) to receiver medium (receiver compartment) involves release of drug from the patch to the buccal surface, permeation of drug into the buccal tissue, and release (after dissolution if necessary) of drug from the tissue into the receiver chamber medium.

The patch described herein is useful for extremely hydrophobic fenretinide, and comprises an effective amount on one or more solubilizers to facilitate continuous in vitro and in vivo fenretinide release and tissue permeation enhancers to improve fenretinide permeability across buccal mucosa. To maintain a desired sink condition in the release/receiver chamber medium, appropriate quantity of suitable solubilizing agent can be incorporated. In this Example, the optimal quantity of nonionic surfactant in the release media was selected by matching the drug solubility to that in bovine serum.

Figure 10A:
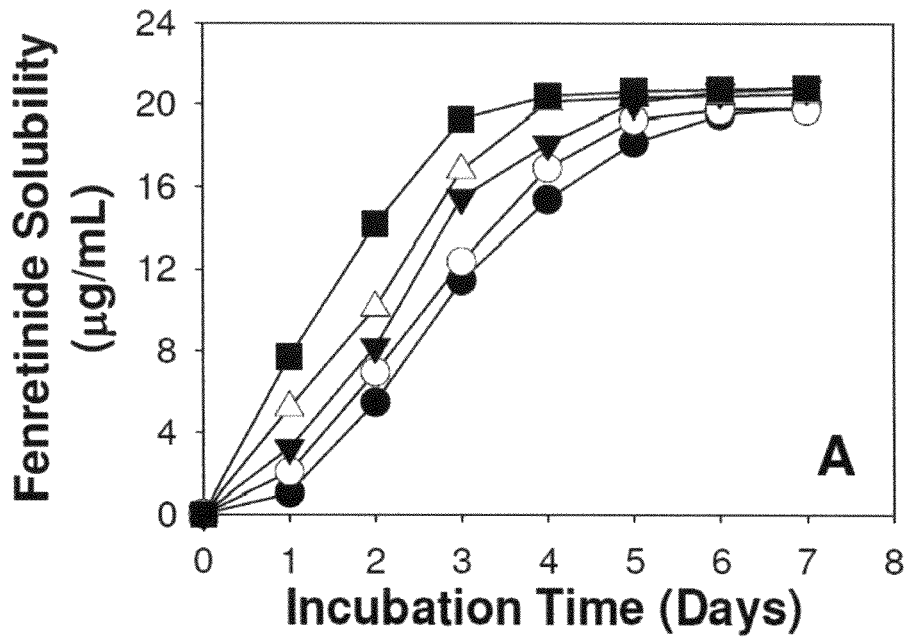
FIGS. 10A-10B: Graph showing solubilization of fenretinide in bovine serum. The effect of quantity (0.9 (•), 2.26 (○), 3.97 (▼), 8.03 (Δ), and 20.05 (■)) of fenretinide added in 15-mL bovine serum and incubation time on the solubility of fenretinide (FIG. 10A) and the relationship between the quantity of fenretinide added and time required to reach equilibration (FIG. 10B). Solubility study was conducted at 37° C. under the protection from light.

The solubility of fenretinide in bovine serum at different fenretinide concentrations (0.9, 2.26, 3.97, 8.03 and 20.5 mg) and incubation times (1-7 days) is shown in FIGS. 10A-1010B. The solubility of fenretinide in bovine serum was found to be 21±1 µg/mL (FIG. 10A). Bovine serum comprises numerous proteins namely albumin, lipoproteins and serum retinol-binding protein (RBP). Enhanced solubility of fenretinide in bovine serum can be attributed to protein-drug binding or complexation.

Figure 10B:
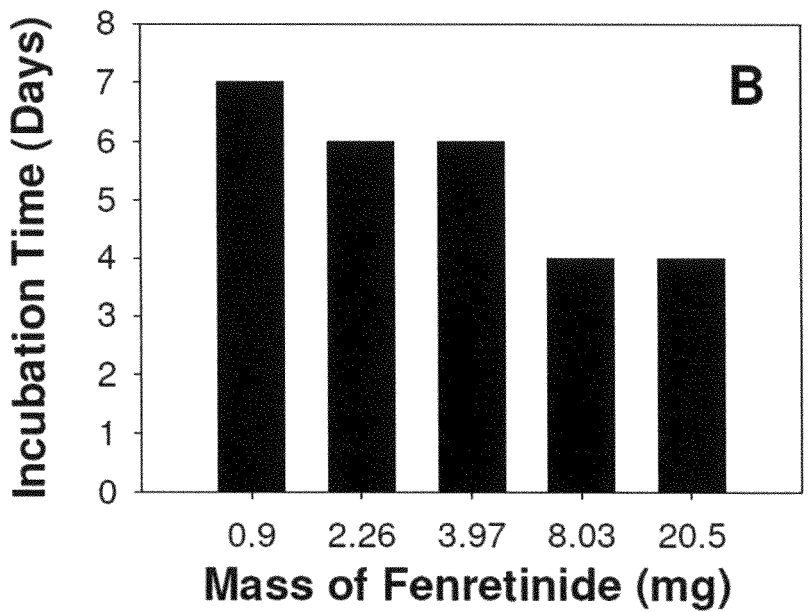

The time taken by fenretinide to reach equilibrium with bovine serum was affected by the amount of fenretinide added in bovine serum. For example, when the amount of fenretinide was increased from 0.9 to 8.03 mg, the time required to achieve equilibrium was reduced from 7 to 4 days (FIG. 10B). Further increases in fenretinide quantity did not reduce the time required for equilibration, thereby suggesting the necessity of minimum ~8 mg of fenretinide and 4 days incubation time to reach equilibrium state with 15 mL serum. A concentration of 0.084% Tween® 80 required to reach equivalent solubility of fenretinide (21 µg/mL in bovine serum) in test medium (receiver chamber medium i.e., PBS, pH 7.4) was then determined from the perfect linear relationship of fenretinide solubility in PBS versus Tween® 80 concentration above the surfactant critical micelle concentration. Hence, PBS+0.084% Tween® 80 was then used to mimic physiological solubilization/sink condition in the ex vivo drug permeation studies.

Enhanced Ex vivo Porcine Buccal Mucosal Permeation of Fenretinide by Co-incorporation of Propylene Glycol and Menthol in Fenretinide/Eudragit® RL-PO Patches.

Figures 11A, 11B, 11C:
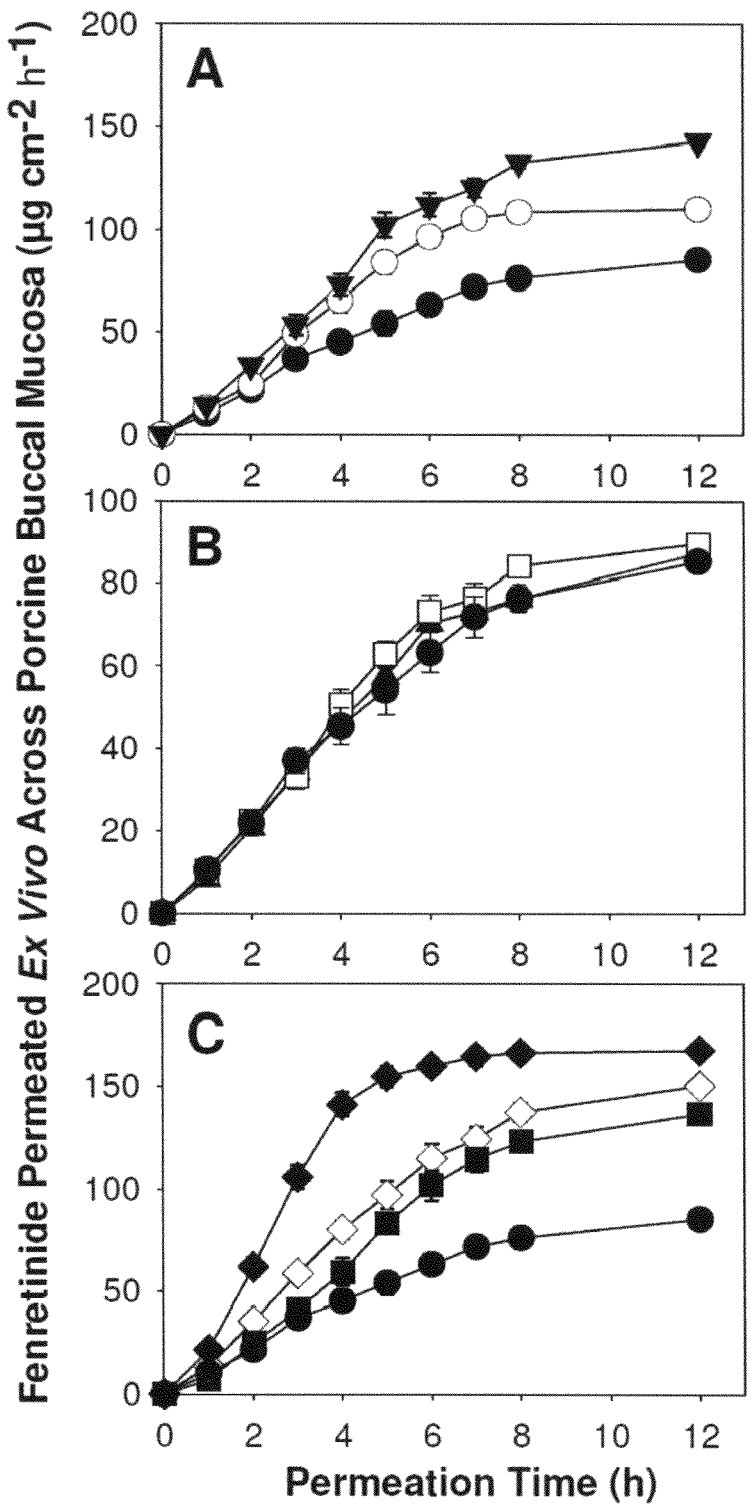
FIGS. 11A-11C: Graph showing co-incorporation of propylene glycol (PG) or PG+menthol in fenretinide/Eudragit® RL PO patches significantly enhance fenretinide permeation across porcine buccal mucosa. The effect of co-incorporation of 0 (•), 5 (○) and 10 (▼) wt % PG (FIG. 11A); 5 (▲) and 10 (△) wt % menthol (FIG. 11B), and 1 wt % PG+5 wt % menthol (▲), 2.5 wt % PG+5 wt % menthol (◇) and 10 wt % PG+5 wt % menthol (◆) (FIG. 11C) in patches on ex vivo permeation of fenretinide across porcine buccal mucosa. Ex vivo permeation studies were conducted using side-by-side flow-through diffusion cells at 37° C. Permeation enhancer-free patch comprised of 5 wt % fenretinide, 20 wt % Tween® 80, and 40 wt % sodium deoxycholate. Symbols represent mean±SE, n=5.

The effect of co-incorporation of single (5 and 10 wt % PG or menthol) and mixed (1 wt % PG+5 wt % menthol, 2.5 wt % PG+5 wt % menthol or 10 wt % PG+5 wt % menthol) permeation enhancers in fenretinide/Eudragit® RL PO mucoadhesive patches on ex vivo porcine buccal mucosal permeation of fenretinide is shown in FIGS. 11A-11C. Ex vivo permeation of fenretinide increased steadily over a period of 8 h and then reached a plateau thereafter. The both the flux (Js) at steady state and the enhancement factor (EF=Js with enhancer/Js without enhancer) were calculated.

The fraction of drug permeated across buccal mucosa and deposited in the buccal tissue, and values of Js and EF are given in Table 5.

TABLE 5

Evaluation of Potential of Co-incorporation of Permeation Enhancers (Propylene Glycol (PG), Menthol or PG + Menthol) in Fenretinide/Eudragit ® RL PO Patches to Enhance Porcine Buccal Mucosal Permeation of Fenretinide Ex Vivo.

| Patch formulation | Flux ($J_s$) ($\mu g \, cm^{-2} \, h^{-1}$)[c] | Fenretinide in the receptor medium (µg/mL) | Fenretinide in $EF^b$ the tissue (µg/g) | |
|---|---|---|---|---|
| Permeation enhancer-free | 10.0 ± 0.5 | 22.3 ± 0.5 | 43.8 ± 6.1 | 1.0 |
| 5 wt % PG | 16.2 ± 0.9 | 28.8 ± 0.8 | 158.5 ± 4.7 | 1.6 |
| 10 wt % PG | 22.8 ± 1.3 | 37.4 ± 0.5 | 170.7 ± 5.3 | 2.3 |
| 5 wt % Menthol | 12.4 ± 0.6 | 22.8 ± 0.5 | 61.7 ± 5.1 | 1.2 |
| 10 wt % Menthol | 12.7 ± 0.7 | 23.5 ± 0.7 | 65.3 ± 4.7 | 1.3 |
| 1 wt % PG + 5 wt % Menthol | 17.9 ± 0.6 | 35.8 ± 1.0 | 172.1 ± 7.6 | 1.8 |
| 2.5 wt % PG + 5 wt % Menthol | 20.2 ± 0.8 | 39.4 ± 0.8 | 175.6 ± 7.0 | 2.0 |
| 10 wt % PG + 5 wt % Menthol | 39.8 ± 0.9 | 43.9 ± 0.6 | 241.1 ± 9.8 | 4.0 |

[a]J: Steady state flux was calculated from linear regression of cumulative amount permeated vs time;
[b]Enhancement factor (EF) = $J_s$ in the presence of permeation enhancer/$J_s$ in the absence of permeation enhancer; Values represent mean ± SE, n = 5.

Co-incorporation of single (FIG. 11A and FIG. 11B) or mixed (FIG. 11C) permeation enhancers in the patch led to significant enhancement (p<0.001) in the rate and extent of fenretinide permeation across porcine buccal mucosa (see Table 5).

For example, the flux for permeation enhancer-free patch was found to be ~10 µg cm$^{-2}$ h$^{-2}$. After co-incorporation of 10 wt % PG or 10 wt % PG+5 wt % menthol, the flux was increased to ~23 (EF=2.3) and 40 (EF=4) µg cm$^{-2}$ h$^{-2}$, respectively. In contrast, a slight increase in the flux was observed with menthol patch formulations (Js=~13 µg cm$^{-2}$ h$^{-2}$). The levels of drug in tissue were in agreement with the values of flux (see Table 5). Fenretinide content in buccal tissue after 12 h of ex vivo permeation with permeation enhancer-free patch was found to be ~44 µg/g. Co-incorporation of PG or PG+menthol led significantly high amount of fenretinide recovery from the buccal tissue (~171 and 241 µg fenretinide/g tissue with 10 wt % PG and 10 wt % PG+5 wt % menthol formulation, respectively), thereby indicating increased tissue localization/permeation of fenretinide in the presence of PG or PG+menthol. A moderate enhancement effect was exhibited by menthol alone.

Propylene glycol exerts its permeation enhancement effect by competing for the solvation sites of the polar head groups of the lipid bilayers and occupying the hydrogen bonding sites, thereby increasing the solubility of this site for the permeant. PG may increase the lipid fluidity which in turn facilitates enhanced drug permeation. Enhanced permeation of fenretinide in the presence of PG can be attributed to one or both of these mechanisms. Menthol, on the other hand, has the ability to modify the drug diffusivity and/or partitioning by disrupting the conformational order of the intercellular lipids in bilayers. Menthol alone it did not provide significant permeation enhancement of fenretinide (p>0.001). This result can be attributed at least in part to non-homogeneous distribution of menthol in fenretinide/Eudragit® RL PO matrix (see FIG. 1D) due to crystallization and aggregation of menthol during solvent evaporation. When PG was combined with menthol, this issue was overcome (see FIG. 1D) and pronounced fenretinide permeation enhancement was observed relative to menthol alone (see FIG. 11C and Table 5). Desirable fenretinide permeation observed with mixed permeation enhancers (PG+menthol) can be attributed to synergistic effect between menthol and PG.

Morphological and Histological Characteristics.

Photomicrographs of the sections of buccal mucosa are shown in FIGS. 12A-12H. The porcine buccal mucosa, similar to human buccal mucosa, consists of an outermost layer of keratinized stratified squamous epithelium, below which lies a basement membrane, a lamina propria followed by the submucosa containing the buccinator muscle as the innermost layer. Regardless of patch application, all sections showed an appropriately maturing stratified squamous epithelium. Scattered mitotic figures were restricted to the basilar layers, and the outermost granular and corneal layers showed appropriate terminal differentiation as reflected by surface parakeratin production. No evidence of changes consistent with extensive epithelial perturbations attributable to a contact mucositis, e.g., hydropic degeneration of the basal cell layer or acantholysis were noted.

Figures 12A, 12B, 12C, 12D, 12E, 12F, 12G, 12H:
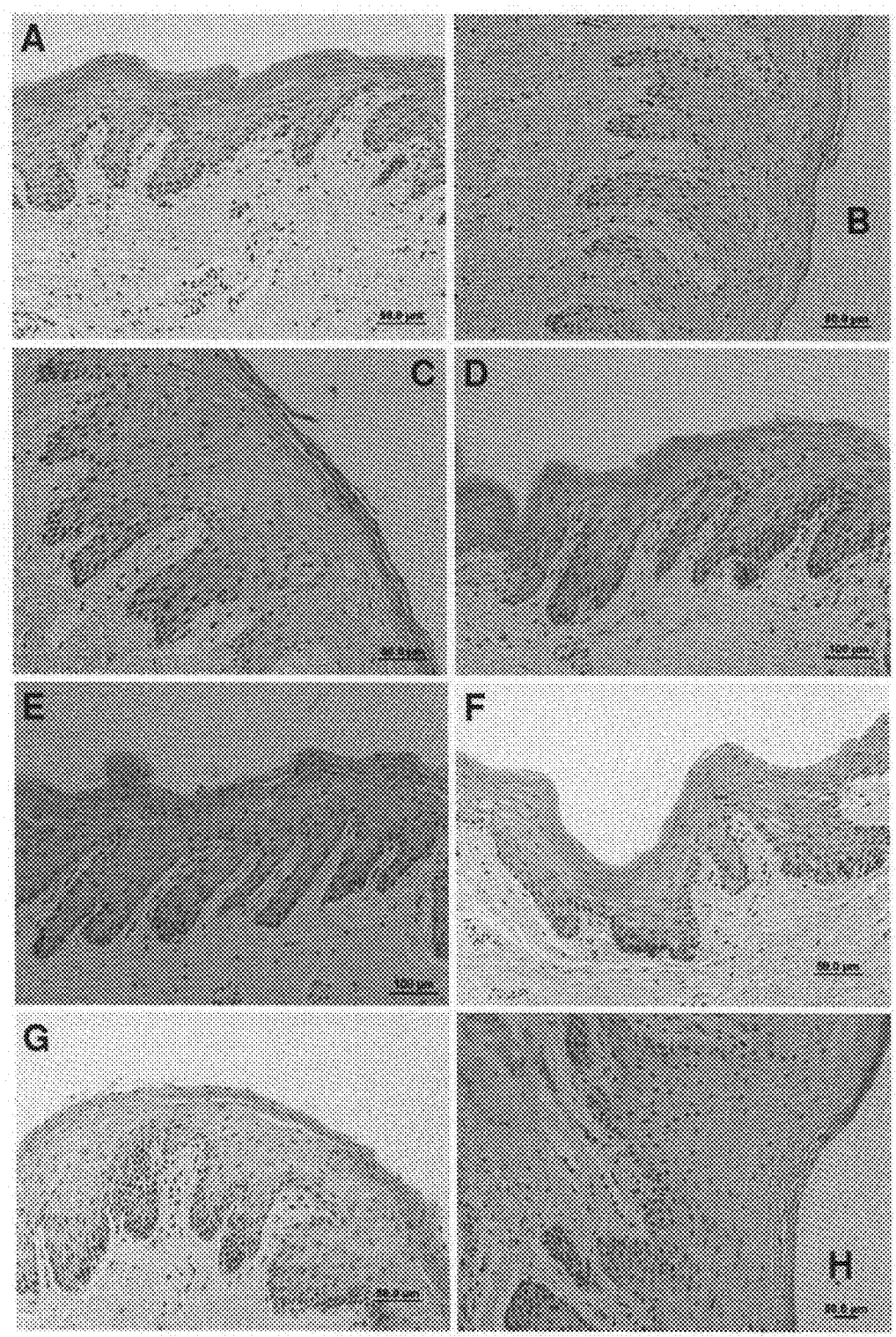
FIGS. 12A-12H: Photographs showing histological examination of porcine buccal tissue before and after fenretinide buccal permeation enhancement with permeation enhancers loaded mucoadhesive patches. The effect of co-incorporation of 0 wt % (FIG. 12A), 5 wt % (FIG. 12B) or 10 wt % (FIG. 12C) propylene glycol (PG); 5 wt % (FIG. 12D) or 10 wt % (FIG. 12E) wt % menthol; and, 1 wt % PG+5 wt % menthol (FIG. 12F), or 2.5 wt % PG+5 wt % menthol (FIG. 12G), or 10 wt % PG+5 wt % menthol (FIG. 12H) in fenretinide/Eudragit RL PO mucoadhesive patches on histological changes of porcine buccal tissue. As shown in these photomicrographs, patch application (with or without permeation enhancers) did not dramatically perturb porcine buccal mucosa. All sections demonstrate a preserved basement membrane and basal cell layer, an intact stratified squamous surface epithelium with an overlying parakeratotic layer. Notably, no evidence of changes consistent with extensive epithelial damage e.g., hydropic degeneration of the basal cell layer or acantholysis were observed in multiple sections. The evidence of increased intracellular and intercellular edema observed in epithelia exposed to increased levels PG (FIG. 12C and FIG. 12H) likely reflects diffusion of PG into subject keratinocytes as well as the intercellular spaces. Images were taken by a light microscope. Permeation enhancer-free patch comprised of 5 wt % fenretinide, 20 wt % Tween® 80, and 40 wt % sodium deoxycholate. Release Time (h).

Basal epithelial cells are tightly bound together in the control (no patch attachment) sample (see FIG. 12A). Noticeable morphological changes (e.g., prickle cells) in the underlying layers and significant loss of superficial cell layers were not apparent after attachment of 5 wt % (see FIG. 12B) and 10 wt % (see FIG. 12C) wt % PG loaded patches. An increase in intercellular edema and swelling of buccal epithelium are visible, however, in FIG. 12B and FIG. 12C when the loading of PG is above 5 wt %.

The photomicrographs of buccal epithelium after treatment with 5 and 10 wt % menthol loaded patches are respectively shown in FIG. 12D and FIG. 12E. It is visible that the epithelium layers were intact in both the samples. In addition, there was no sign of cellular swelling and significant histological and ultrastructural changes.

Similar results were observed in samples treated with 1 wt % PG+5 wt % menthol (see FIG. 12F) and 2.5 wt % PG+5 wt % menthol (see FIG. 12G) loaded patches. In contrast, tissue exposed to the 10 wt % PG+5% menthol loaded patch showed a moderate increases in intracellular space and intercellular edema (see FIG. 12H). Since menthol did not cause any epithelial cell alteration, it is likely that higher (10 wt %) loading of PG in the patch resulted in increased intracellular space and intercellular edema.

The histological changes (e.g., increases in intracellular space and intercellular edema) observed in the tissues treated with 5 and 10 wt % PG loaded patches (see FIG. 12B, FIG. 12C and FIG. 12H) are indicative of diffusion of PG into subject keratinocytes as well as the intercellular spaces. Upon permeation and accumulation in cells, it is likely that PG interacted with intercellular or membrane lipids, thereby increasing the permeability of fenretinide through epithelium. Since 2.5 wt % PG+5 wt % menthol loaded patches exhibited optimal drug permeation enhancement with no morphological and histological changes, this formulation was selected and used to further evaluate in vivo release, permeation and tissue deposition kinetics of fenretinide, as described below.

In Vitro and In Vivo Release Characteristics of Permeation Enhancers-Loaded Fenretinide/Eudragit® RL-PO Patches.

Figure 13:
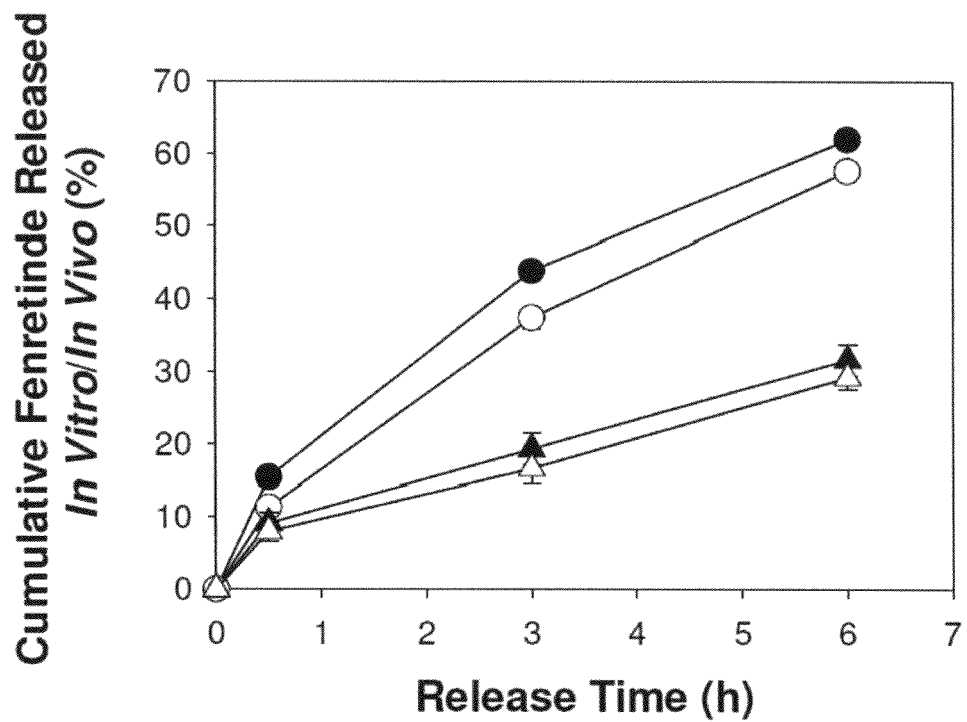
FIG. 13: Graph showing in vitro and in vivo release characteristics of permeation enhancers-free and permeation enhancers-loaded fenretinide/Eudragit® RL PO mucoadhesive patches. Cumulative amount of fenretinide released in vitrol in vivo from permeation enhancers-free (○: in vitro; Δ: in vivo) and permeation enhancers (2.5 wt % propylene glycol+5 wt % menthol)-loaded (•: in vitro; ▲: in vivo) patches as a function of time. In vitro and in vivo release studies were conducted in simulated saliva containing 5% w/v sodium deoxycholate (pH 6.8) at 37° C. and rabbits, respectively. Permeation enhancer-free patch comprised of 5 wt % fenretinide, 20 wt % Tween® 80, and 40 wt % sodium deoxycholate. Symbols represent mean±SE, n=4 (in vitro) or 6 (in vivo).

In vitro and in vivo fenretinide release from permeation enhancer-free and 2.5 wt % PG+5 wt % menthol-loaded fenretinide/Eudragit® RL-PO patches is shown in FIG. 13. Both the patch formulations provided continuous in vitro and in vivo fenretinide release from Eudragit® polymeric matrices, and the addition of PG and menthol did not significantly affect the release kinetics, indicating further fenretinide solubilization and/or changes to the patch swelling behavior. In this case, the patch release characteristics were largely determined by sodium deoxycholate and Tween® 80, which served as the effective solubilization role in the patch formulation There was a significant difference (p<0.001) between in vitro and in vivo fenretinide release characteristics of permeation enhancer-free and 2.5 wt % PG+5 wt % menthol-loaded fenretinide/Eudragit® RL-PO patches (see FIG. 13), although the continuous release trend was the same. This difference can be linked to dissimilarity in test conditions (e.g., in vitro drug release in simulated saliva vs. in vivo drug release followed by permeation across buccal mucosal membrane).

Enhanced In Vivo Rabbit Buccal Mucosal Permeation and Deposition of Fenretinide by Co-incorporation of Propylene Glycol and Menthol in Fenretinide/Eudragit® RL-PO Patches.

Figure 14:
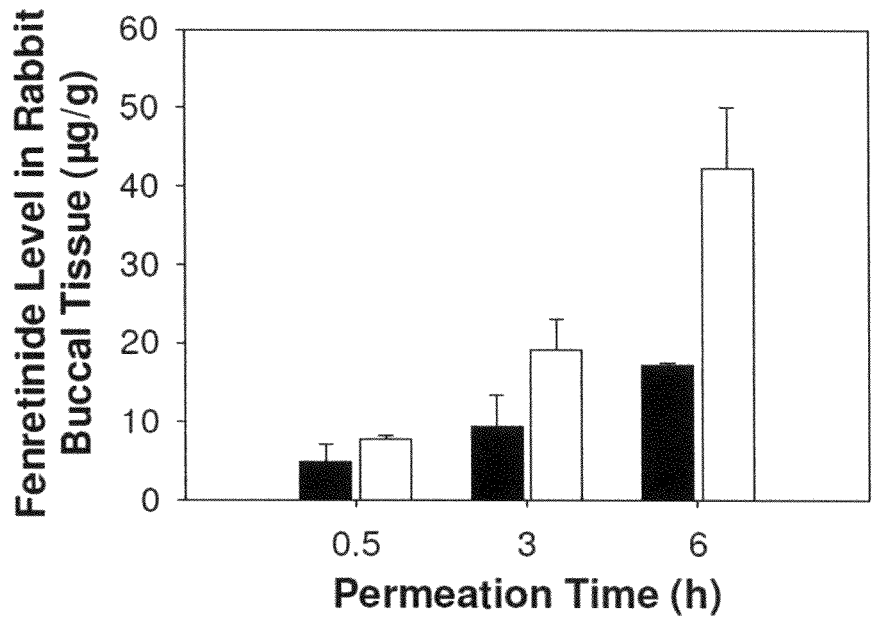
FIG. 14: Graph showing co-incorporation of Permeation enhancers (2.5 wt % propylene glycol+5 wt % menthol) in fenretinide/Eudragit® RL PO patch enhances in vivo buccal mucosal permeation of fenretinide. Tissue levels of fenretinide as a function of buccal administration time of permeation enhancer-free (filled bars) and permeation enhancers-loaded (open bars) patches in rabbits. Permeation enhancer-free patch comprised of 5 wt % fenretinide, 20 wt % Tween® 80, and 40 wt % sodium deoxycholate. Bars represent mean±SE, n=6).

The effect of co-incorporation of permeation enhancers (PG+menthol) in fenretinide/Eudragit® RL-PO patches on in vivo buccal mucosal permeation and deposition of fenretinide is shown in FIG. 14. The level of fenretinide in rabbit buccal tissue increased steadily as function of attachment time of both the patch (permeation enhancer-free and permeation enhancers-loaded patches) formulations (see FIG. 14), thereby indicating excellent efficacy of these patch formulations to provide continuous in vivo fenretinide permeation across the rabbit buccal mucosa. The extent of fenretinide permeation and tissue deposition provided by 2.5 wt % PG+5 wt % menthol-loaded patches was significantly higher (43.0±7.7 µg fenretinide/g tissue after 6 h of attachment) than that of permeation enhancer-free patch (17.3±0.3 µg fenretinide/g tissue after 6 h of attachment) (see FIG. 14). These results show excellent effectiveness of co-incorporation of PG and menthol to obtain improved oral mucosal permeation and tissue levels of fenretinide. Different permeation and tissue deposition kinetics of fenretinide obtained with ex vivo and in vivo studies can be attributed to dissimilarity in key test conditions (e.g., porcine vs. rabbit buccal mucosas, ex vivo vs. in vivo sink conditions).

These data demonstrate the therapeutic advantage imparted by mucoadhesive patch local delivery of fenretinide, i.e., obtaining pharmacologically active levels in the target tissue. In vitro fenretinide concentrations between 1 and 10 µM are useful for inducing desirable chemopreventive effects, e.g., cellular terminal differentiation (<3 µM) and apoptosis (>5 µM). As shown herein, the levels of fenretinide delivered to rabbit buccal mucosa from permeation enhancers loaded patch ranged from 7.75 µg/g (0.5 hour; 19.8 µM) to 42.36 µg/g (6 hours; 108.2 µM). Therefore, short duration patch application (i.e., less than 30 minutes) are especially useful in certain embodiments in order to provide therapeutically relevant concentrations in the targeted oral epithelium. In addition, due to the decreased treatment time, such applications can facilitate patient compliance.

The intraoral site-specific fenretinide delivery us thus enhanced by the mucoadhesive patches that provide enhanced buccal mucosal permeation and tissue levels of fenretinide. Suitable permeation enhancers (PG and menthol) were co-incorporated in fenretinide/Eudragit® RL-PO patches. Mucoadhesive patches containing a desired drug delivery (fenretinide+solubilizers+permeation enhancers), adhesive, and backing layers were prepared by solvent casting and assembling techniques. Co-incorporation of PG or PG+menthol in patches led to significant ex vivo and in vivo buccal mucosal permeation and tissue deposition of fenretinide, a extremely hydrophobic and poorly tissue permeable chemopreventive agent. In one embodiment, a mucoadhesive patch co-incorporated with 2.5 wt % PG+5 wt % menthol was found to be have desired oral mucosal permeation enhancement without significantly affecting the observed histology of the oral mucosa.

Methods of Treatment

Methods of using the formulations disclosed herein generally involve applying the formulations topically to mucosal surfaces of the oral cavity.

In one embodiment, the method generally comprising: providing a transmucosal system comprising the formulation described herein; applying the transmucosal system to a mucosal membrane of a subject; and, keeping the transmucosal system in contact with the mucosal membrane for a therapeutically effective period of time; and, optionally removing the transmucosal system when a desired therapeutic effect has been achieved.

In certain embodiments, the patch contains a permeation enhancer agent that is not present an adhesive layer, but is only present in the formulation.

In another embodiment, the method includes treatment and prophylaxis of a disease, comprising: administering to a subject in need of such treatment the formulation described herein.

In certain embodiments, the formulation can be present as a mouth product such as a toothpaste, a mouthwash or mouth rinse, a gel or paste, a spray, a chewing gum, and/or a lozenge.

Example 3

Therapeutic Uses

The formulations described herein have useful clinical applications for preventing development (primary chemoprevention) or inhibiting recurrence (secondary chemoprevention) of oral cancer.

Another therapeutic use includes treatment for includes inhibiting growth of a tumor such as head and neck squamous carcinoma cells (HNSCC).

Another therapeutic treatment includes decreasing the size of a tumor, comprising tumor cells, wherein the tumor cells are head and neck squamous cell carcinoma cells.

Another therapeutic treatment includes preventing head and neck squamous cell carcinoma (HNSCC).

Another clinical application is the use of the formulations on actinically induced precancerous lesions of the lower lip, known as actinic cheilitis. While not as clinically aggressive as intraoral dysplastic lesions, lip lesions need to be surgically managed, and can progress into oral squamous cell carcinoma.

Still other clinical applications can include all variants of oral squamous cell carcinoma (including these actinically-induced lip lesions) as treatment sites.

Other clinical applications include the treatment, amelioration or reversal of oral epithelial dysplasias, such as Fanconi anemia.

Kits

Also provided herein are kits comprising the formulations described herein and instructions for use in a method for administering to a subject.

In one embodiment, the kit includes instructions for use in the treatment of a cancerous or precancerous condition. In certain embodiments, the kit includes instructions for administering the composition to a mammal with a head or neck basal cell precancerous or cancerous condition. It is to be understood that the formulations described herein can be packaged in kit form. In one aspect, the invention provides a kit that includes delivery systems in suitable packaging.

Each formulation is supplied in a pharmaceutically acceptable carrier that is suitable for inventory storage. A kit may optionally provide additional components that are useful in the methods and formulation procedures of the invention, such as buffers, reacting surfaces, or means of purifying delivery particles.

In addition, the kits optionally include labeling and/or instructional or interpretive materials providing directions (i.e., protocols) for the practice of the methods of this invention, such as preparation, formulation and/or use of delivery particles. While the instructional materials typically comprise written or printed materials they are not limited to these formats. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to Internet sites that provide such instructional materials.

In one embodiment, there is provided herein a prophylactic kit for reducing the likelihood of disease in a subject comprising: (a) a bioadhesive pharmaceutical formulation as described herein; and (b) a delivery system, such as a patch or film for delivery of the formulation.

In another embodiment, there is provided herein a therapeutic kit for treating disease in a subject comprising: (a) a bioadhesive pharmaceutical formulation as described herein; and (b) a delivery system, such as a patch or film for delivery of the formulation.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A formulation, comprising:
   from about 5 wt % to about 95 wt %, based on the total weight of the formulation, mucoadhesive material, wherein the mucoadhesive material comprises a methacrylate copolymer;
   from about 0.1 wt % to about 5 wt %, based on the total weight of the formulation, fenretinide or a pharmaceutically acceptable salt thereof;
   a transmucosal permeation enhancer agent comprising a mixture of:
      from about 1 wt % to about 2.5 wt %, based on the total weight of the formulation, propylene glycol (PG), and
      from 1 wt % to about 5 wt %, based on the total weight of the formulation, menthol; and,
   at least one solubilizer agent selected from the group consisting of a nonionic surfactant, a bile salt, a phospholipid, a polymeric solubilizer, and combinations thereof.

2. The formulation of claim 1, wherein the at least one solubilizer agent is selected from the group consisting of sodium deoxycholate, a polyoxy-ethylene-sorbitan higher fatty acid ester, a polyoxyethylene (20) oleyl ether, and combinations thereof.

3. The formulation of claim 2, wherein the polyoxyethylene-sorbitan higher fatty acid ester is selected from polysorbate 20, polysorbate 80, and mixtures thereof.

4. The formulation of claim 1, wherein the fenretinide and the permeation enhancer agent are adapted to be in contact with the same mucosal membrane.

5. The formulation of claim 4, wherein the mucosal membrane is the buccal mucosa.

6. The formulation of claim 1, wherein the formulation contains a predetermined amount of fenretinide in an amount selected from the group consisting of 10 µg, 15 µg, 25 µg, 50 µg, 100 µg, 500 µg, 1 mg, 2 mg, 3 mg, 4 mg, 5 mg, 6 mg, 7 mg, 8 mg, 9 mg, and 10 mg and an adhesive material, the adhesive material providing for adherence to the oral mucosal membrane of a subject.

7. The formulation of claim 1, wherein the amount of the fenretinide absorbed via the oral mucosa is at least 35% of the drug in the formulation.

8. The formulation of claim 1, wherein the methacrylate copolymer comprises ethyl acrylate, methyl methacrylate, and methacrylic acid ester.

9. The formulation of claim 1, wherein the solubilizer agent comprises a bile salt selected from the group consisting of sodium glycocholate, sodium deoxycholate, sodium cholate, sodium taurocholate, and combinations thereof.

10. A mouth product comprising the formulation of claim 1, wherein the mouth product is selected from the group consisting of a toothpaste, a mouthwash or mouth rinse, a gel or paste, a spray, a chewing gum, and a lozenge.

11. A mucoadhesive patch comprising the formulation of claim 1.

12. A transmucosal drug delivery system comprising at least one drug-release layer comprised of the formulation of claim 1, at least one adhesive layer, and at least one backing layer.

13. A drug dosage form for oral transmucosal administration, comprising:
   the formulation of claim 1; and an adhesive material, the adhesive material providing for adherence of the drug dosage form to the oral mucosa membrane.

14. A method of treating a disease or disorder, comprising: administering the formulation of claim 1 to a subject in need thereof.

15. The method of claim 14, wherein the disease or disorder is a cancerous or precancerous condition.

16. The method of claim 14, wherein the disease or disorder comprises one or more of: oral squamous cell carcinoma, intraoral dysplastic lesions, head and neck squamous carcinoma.

17. A method of treating a tumor comprising head and neck squamous carcinoma cells, comprising administering an effective amount of the formulation of claim 1 to a subject in need thereof.

18. A method of treating actinically induced precancerous lesions, comprising administering an effective amount of the formulation of claim 1 to a subject in need thereof.

19. A method for chemoprevention of a precancerous condition, comprising topically administering to a subject in need of such chemoprevention the formulation of claim 1.

20. The method of claim 19, wherein the formulation is administered to an interior of an oral cavity of the subject.

21. The method of claim 20, wherein a single or repeated oral transmucosal administration to a subject results in a bioavailability of greater than 70%.

22. The method of claim 20, wherein the oral transmucosal administration to a subject is repeated and results in a bioavailability with a coefficient of variation of less than 40%.

23. The method of claim 20, wherein a single oral transmucosal administration of the formulation to a subject results in a Tmax of from about 6 hours to about 12 hours.

24. A method of using the formulation of claim 1, comprising:
i) providing a transmucosal system comprised of the formulation of claim 1;
ii) applying the transmucosal system to a mucosal membrane of a subject; and,
iii) keeping the transmucosal system in contact with the mucosal membrane for a therapeutically effective period of time; and,
iv) optionally removing the transmucosal system when a desired therapeutic effect has been achieved.

25. The method of claim 24, wherein the transmucosal system includes an adhesive material.

26. The method of claim 25, wherein the formulation and the adhesive material are present in separate compartments.

27. A method for making a buccal drug delivery system, comprising:
i) preparing a drug-release layer comprised of the formulation of claim 1;
ii) preparing an adhesive layer; and,
iii) assembling the drug layer and the adhesive layers onto a backing layer.

28. A method for increasing permeation of a fenretinide formulation from a drug-releasing layer into a mucosa of a subject in need thereof, comprising:
i) admixing from about 5 wt % to about 95 wt %, based on the total weight of the formulation, mucoadhesive material, wherein the mucoadhesive material comprises a methacrylate copolymer;
from about 0.1 wt % to about 5 wt %, based on the total weight of the formulation, fenretinide or a pharmaceutically acceptable salt thereof;
a transmucosal permeation enhancer agent comprising a mixture of: from about 1 wt % to about 2.5 wt %, based on the total weight of the formulation, propylene glycol, and from 1 wt % to about 5 wt %, based on the total weight of the formulation, menthol;
and at least one solubilizer agent selected from the group consisting of a nonionic surfactant, a bile salt, a phospholipid, a polymeric solubilizer, and combinations thereof, and
ii) forming the admixture into a drug-release layer.

29. A method for making the formulation of claim 1, comprising:
i) mixing a quantity of the at least one solubilizer agent, the mucoadhesive material, and the transmucosal permeation enhancer agent in a solvent to form a solvent mixture;
ii) adding the fenretinide or pharmaceutically acceptable salt thereof to the solvent mixture of step i); and, optionally adjusting a volume thereof to 10 mL with the solvent mixture of step i);
iii) forming a layer of the fenretinide mixture of step ii); and,
iv) drying the layer of step iii).

30. The method of claim 29, wherein the at least one solubilizer agent is selected from the group consisting of sodium deoxycholate, a polyoxyl-ethylene-sorbitan higher fatty acid ester, a polyoxyethylene(20) oleyl ether, and combinations thereof.

* * * * *

UNITED STATES PATENT AND TRADEMARK OFFICE
CERTIFICATE OF CORRECTION

| | | |
|---|---|---|
| PATENT NO. | : 10,758,619 B2 | Page 1 of 1 |
| APPLICATION NO. | : 13/885436 | |
| DATED | : September 1, 2020 | |
| INVENTOR(S) | : Susan R. Mallery et al. | |

It is certified that error appears in the above-identified patent and that said Letters Patent is hereby corrected as shown below:

In the Specification

Column 1, Lines 16-17, delete "This invention was not made with any Government support and the Government has no rights in this invention." and insert the following:
-- This invention was made with government support under RR025755 and R01 CA227273 awarded by the National Institutes of Health. The government has certain rights in the invention. --

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*